(12) United States Patent
Wisniewski et al.

(10) Patent No.: US 8,420,601 B2
(45) Date of Patent: Apr. 16, 2013

(54) BIOCOMPATIBLE MATERIALS CONTAINING STABLE COMPLEXES OF TSG-6 AND HYALURONAN AND METHOD OF USING SAME

(75) Inventors: Hans-Georg Wisniewski, Riverdale, NY (US); Mary K. Cowman, Mohegan Lake, NY (US); Philip Band, West Orange, NJ (US)

(73) Assignees: New York University, New York, NY (US); Polytechnic Institute of NYU, Brooklyn, NY (US)

( * ) Notice: Subject to any disclaimer, the term of this patent is extended or adjusted under 35 U.S.C. 154(b) by 0 days.

(21) Appl. No.: 13/299,999

(22) Filed: Nov. 18, 2011

(65) Prior Publication Data

US 2012/0064150 A1   Mar. 15, 2012

Related U.S. Application Data

(62) Division of application No. 12/372,598, filed on Feb. 17, 2009, now Pat. No. 8,093, 365.

(60) Provisional application No. 61/033,204, filed on Mar. 3, 2008.

(51) Int. Cl.
| | |
|---|---|
| *A61K 38/16* | (2006.01) |
| *A61K 31/726* | (2006.01) |
| *A61K 31/728* | (2006.01) |
| *C07K 14/435* | (2006.01) |
| *C07K 17/02* | (2006.01) |

(52) U.S. Cl.
USPC ............ 514/17.1; 514/21.2; 514/54; 530/350

(58) Field of Classification Search ........................ None
See application file for complete search history.

(56) References Cited

U.S. PATENT DOCUMENTS

2007/0071740 A1 * 3/2007 Tseng et al. ................. 424/94.1

FOREIGN PATENT DOCUMENTS

WO     2006/102768 A1    10/2006

OTHER PUBLICATIONS

Fries et al., Acta Biochimica Polonica, 2003, vol. 50(3), pp. 735-742.*
He et al., Biochemical characterization and function of complexes formed by hyaluronan and the heavy chains of inter-alpha-inhibitor (HC.HA) purified from extracts of human amniotic membrane, The Journal of Biological Chemistry, 284 (30):20136-20146 (2009).
Lesley et al., TSG-6 modulates the interaction between hyaluronan and cell surface CD44, The Journal of Biological Chemistry, 279(24):25745-25754 (2004).
Mukhopadhyay et al., Two distinct populations of tumor necrosis factor-stimulated Gene-6 protein in the extracellular matrix of expanded mouse cumulus cell-oocyte complexes, Archives of Biochemistry and Biophysics, 394 (2):173-181 (2001).
Wisniewski et al., TSG-6 protein binding to glycosaminoglycans, The Journal of Biological Chemistry, 280 (15):14476-14484 (2005).
Allcock and Lampe, Contemporary Polymer Chemistry, 1981, Prentice-Hall, Inc., Englewood Cliffs, New Jersey, pp. 7-8.
Stevens, Polymer Chemistry, An Introduction, second ed., 1990, Oxford University Press, New York, pp. 10-11, 98 and 99.
Sanggaaro et al., TSG-6 trnasfers proteins between glycosaminoglycans via a Ser28-mediated covalent catalytic mechanism, J. Biol. Chem. 283(49):33919-33926 (2008).
Yingsung et al., Molecular heterogeneity of the SHAP-hyaluronan complex, The Journal of Biological Chemistry, 278 (35):32710-32718 (2003).
Fries et al., Inter-α inhibitor, hyaluronan and inflammation, Acta Biochimica Polonica 50(3):735-742 (Abstract) (2003).
Ratner et al., Biomaterials Science: An Introduction to Materials in Medicine, 2nd edition, 2004 Elsevier, New York, pp. 64, 242 and 244.

* cited by examiner

*Primary Examiner* — Xiaozhen Xie
(74) *Attorney, Agent, or Firm* — Browdy and Neimark, PLLC

(57)     ABSTRACT

The present invention provides a biocompatible material in the form of a water insoluble cross-linked gel, which contains a stable complex of TNF-stimulated gene 6 protein (TSG-6) and hyaluronan.

7 Claims, 13 Drawing Sheets

BIOCOMPATIBLE MATERIALS CONTAINING STABLE COMPLEXES OF TSG-6 AND HYALURONAN AND METHOD OF USING SAME

CROSS-REFERENCE TO RELATED APPLICATIONS

The present application is a divisional of application Ser. No. 12/372,598, filed Feb. 17, 2009, now issued as U.S. Pat. No. 8,093,365, which claims the benefit of priority from U.S. provisional application No. 61/033,204, filed Mar. 3, 2008, the entire contents of which are hereby incorporated by reference.

BACKGROUND OF THE INVENTION

1. Field of the Invention

The present invention relates to biocompatible hyaluronan-containing materials and uses thereof.

2. Description of the Related Art

TNF-Stimulated Gene 6 (TSG-6)

TNF-stimulated gene 6 (TSG-6) encodes a glycoprotein of ca. 35 kDa that is commonly referred to as TSG-6 protein (Lee et al., 1990 and 1992; and Wisniewski et al., 2004). Expression and function of TSG-6 have been associated with inflammation and fertility.

TSG-6 protein consists of two domains, the N-terminal link module and the C-terminal CUB domain. The N-terminal domain of TSG-6, a so-called link module (Kohda et al., 1996), identifies TSG-6 as a hyaluronan (HA) binding protein. All known proteins sharing this domain are hyaladherins, i.e., HA-binding proteins (Iozzo et al., 1996; Knudson et al., 1993; and Toole, 1990). Not surprisingly, TSG-6 has been shown to bind to HA in solution (Lee et al., 1992; and Kohda et al., 1992) and to immobilized HA (Kahmann et al., 2000; Mahoney et al., 2001; Parkar et al., 1998; and Wisniewski et al., 2005). TSG-6 is the only known HA-binding protein that contains a CUB domain, which may account for some of its unique properties. The 3D structure of the link module of TSG-6 has been solved and many structural details of its interaction with HA have been investigated (Kohda et al., 1996; Kahmann et al., 2000; and Mahoney et al., 2001). The laboratory of the present inventors have previously reported that TSG-6 formed complexes with HA covalently attached to a solid substrate and that these HA-TSG-6 complexes were resistant to dissociation with guanidine HCl, guanidine HCl containing lauryl sulfobetain, SDS plus 2-mercaptoethanol, and dilute NaOH, consistent with the formation of a covalent bond (Wisniewski et al., 2005). The isolated link module is likewise competent to form these tight complexes, indicating that the CUB domain of TSG-6 is not required for this interaction with HA. The CUB domain, a modular unit that is widely shared by numerous proteins, is thought to be a protein-protein and protein-carbohydrate interaction domain (Bork et al., 1993; and Topfer-Petersen et al., 1998).

TSG-6 is a protein whose expression is induced by the pro-inflammatory cytokines TNF-α, IL-1 and IL-17. TSG-6 protein has shown potent anti-inflammatory and tissue-protective activities in experimental models of acute and chronic inflammation. TSG-6 protein has been particularly impressive in ameliorating experimental arthritis, which has been shown in three different models of experimental arthritis using either recombinant TSG-6 or endogenous expression of TSG-6 in two different models of transgenic mice. In addition, TSG-6-deficient mice developed aggravated arthritis and cartilage destruction.

TSG-6 and the ubiquitous plasma protein inter-α-inhibitor (IαI) form a biochemical pathway to permanently modify hyaluronan (HA), a glycosaminoglycan abundant in many tissues. HA is particularly prominent in joints where it serves both as a major structural component of cartilage and, being present at high concentration in synovial fluid, a viscoelastic lubricant. TSG-6 interacts with IαI in the absence of any other factors and serves as acceptor of one heavy chain of IαI, forming a stable TSG-6-HC complex that serves as a stable intermediate for the transfer of HCs to hyaluronan. The resulting HA-HC complexes are stable and have been found in the synovial fluids of patients with rheumatoid arthritis and osteoarthritis (Kida et al., 1999).

IαI is a protein-polysaccharide complex of unique structure, consisting of three polypeptide chains linked by a glycosaminoglycan (GAG) bridge (Enghild et al., 1991; and Salier et al., 1996). The smallest of the three polypeptides, the serine protease inhibitor bikunin, carries a single chondroitin-4-sulfate chain attached via a classical proteoglycan linkage group, while the two closely homologous heavy chains (HC) 1 and 2 are linked to hydroxyl groups of the chondroitin sulfate via ester bonds formed by their C-terminal aspartic acid residues (Enghild et al., 1989, 1991 and 1993). Purified TSG-6, in the absence of HA or any added factors, interacts with IαI resulting in the transfer of one HC from IαI to TSG-6 (Mukhopadhyay et al., 2004; Sanggaard et al., 2005 and 2006; and Wisniewski et al., 1994).

It is intriguing that the HCs of IαI are also found in stable complexes with HA, and have been named serum-derived HA-associated protein (SHAP) (Huang et al., 1993). As in IαI, the HCs are coupled to HA by an ester bond formed by its C-terminal aspartic acid residue (Zhao et al., 1995). The formation of HA-HC complexes has been described both in the absence (Huang et al., 1993) or in the presence of added TSG-6 (Mukhopadhyay et al., 2004; and Rugg et al., 2005).

The HCs of IαI have also been reported to have anti-inflammatory effects in their own right, suggested to be mediated by inhibition of complement activation by circulating immune complexes. Activation of complement in the vascular compartment has been associated with autoimmune and inflammatory conditions, e.g., systemic lupus erythematosus, resulting in platelet damage and fibrin deposition, both in turn causing perpetuation of inflammation.

TSG-6 has been associated with various forms of arthritis (Bayliss et al., 2001; and Wisniewski et al., 1993) and it has been demonstrated by several investigators to exert anti-inflammatory and chondroprotective effects in murine models of acute inflammation and autoimmune arthritis (Bardos et al., 2001; Getting et al., 2002; Giant et al., 2002; Mindrescu et al., 2000 and 2002; and Wisniewski et al., 1996). TSG-6 and IαI play an essential role in female fertility, and both TSG-6- and IαI-deficient female mice are essentially infertile because their ovaries fail to form the HA-rich protective cumulus surrounding oocytes during ovulation (Fulop et al., 2003; Sato et al., 2001; and Zhuo et al., 2001). The drop of IαI concentrations in human plasma during sepsis and the beneficial effects of exogenous IαI in experimental models of sepsis point to a significant role of IαI in human disease (Baek et al., 2003; Balduyck et al., 2000; Lim et al., 2003; Opal et al., 2007; Wu et al., 2004; and Yang et al., 2002). Thus, IαI is considered a prognostic marker for the outcome of septic shock in humans, with low concentrations of IαI predicting mortality. In experimental sepsis, IαI has been shown to increase survival. Bikunin, the protease inhibitory chain of IαI, is also found as a free polypeptide in urine and is therefore also known as urinary trypsin inhibitor (UTI). Bikunin/UTI has been described as having anti-inflammatory and anti-metastatic effects in a range of experimental systems (Kobayashi et al., 2003 and 2006; and Pugia et al., 2005).

IαI also interacts with pentraxin 3 (PTX3), a pathogen-associated molecular pattern receptor. This connection ties IαI firmly to the innate immune response. PTX3 is essential for efficient innate immunity to *Aspergillus fumigatus* infections in the mouse. PTX3 is an activator of complement, and its function in the innate immune system may be related to this ability. IαI binds to PTX3 and may modulate the activity of PTX3 by its ability to modulate complement activation.

TSG-6, IαI, hyaluronan and PTX3 are collectively responsible for the stability of the expanding cumulus-oocyte complex during ovulation, and are therefore essential for female fertility. These components were also recently reported US2070231401 to occur in extracts of amniotic material with anti-inflammatory properties.

Hyaluronan

Hyaluronan is a carbohydrate polymer (polysaccharide), which is normally found in the matrix surrounding cells in vertebrate animals, and is a major component of the vitreous of the eye and the synovial fluid of the joint. Hyaluronan is synthesized by a cell surface enzyme, and extruded directly into the extracellular matrix. Although some hyaluronan is degraded locally, most is transported through the lymph and degraded in the lymph nodes, with most of the remaining amount being cleared rapidly from the blood and degraded by liver endothelial cells. Tissue hyaluronan has a rapid turnover, with approximately one-third of the total being degraded and replaced each day.

Commercial preparations of hyaluronan are isolated from rooster comb or from the culture medium of certain bacteria that are capable of synthesizing the polysaccharide. Hyaluronan contains two different sugar units, which alternate in the polymer, forming a linear chain. The number of sugar units in a single chain of the natural material can reach at least 40,000, which corresponds to a molecular weight of 8,000,000. Commercial preparations of hyaluronan are usually lower in molecular weight, due to degradation during isolation and purification, and are polydisperse (i.e., contain a range of molecular weights). In referring to the molecular weight, an average molecular weight is cited.

A large number of different biomaterials and therapeutic products containing hyaluronan have been proposed for use, and some have been commercialized. Pure hyaluronan is non-immunogenic and has excellent biocompatibility.

References for recent authoritative reviews of the chemistry, biology, and medical applications of hyaluronan are provided below (Lapčik et al., 1998; Balazs, 2004; Asari, 2004; Miller and Avila, 2004; Shu and Prestwich, 2004; Cowman and Matsuoka, 2005; Morra, 2005; Brekke and Thacker, 2006; Stern et al., 2006; Kogan et al., 2007).

Hyaluronan to be Used in Soluble Unmodified Form

The medical applications of soluble unmodified hyaluronan include uses that depend primarily on the physical properties (viscosity, elasticity, osmotic pressure, etc.), and uses that depend wholly or in part on binding of hyaluronan to cell surface receptors. The molecular weight of the hyaluronan, and the concentration of hyaluronan in solutions, are important considerations in both the physical properties and the cell receptor interactions of hyaluronan.

Physical Properties: Solutions of high molecular weight (ca. 400,000 to 6,000,000) hyaluronan are notable for their high viscosity and elastic character, both of these depending also on the concentration and the frequency of deformation (shear rate). Hyaluronan of lower molecular weight has much lower viscoelasticity. Hyaluronan solutions have a high osmotic pressure and contribute to tissue hydration.

Based primarily on the viscoelastic properties, solutions of high molecular weight hyaluronan have been used extensively as tissue protectants and manipulators (viscous tools) in ophthalmic applications, most notably cataract extraction coupled with intraocular lens implantation. Solutions of high molecular weight hyaluronan are also widely used for pain relief in treatment of osteoarthritis of the knee.

Applications based primarily on the hydration properties include protective eye drops for treatment of dry eye, and skin moisturizers for use in cosmetics.

Applications that depend strongly on both hydration and viscous properties include 1) tissue protectants for use in minimizing tissue abrasion, post-surgical adhesion formation, or loss of natural protectant layers in peritoneal dialysis, and 2) wound protectant and healing aids.

Solutions of high molecular weight hyaluronan at sufficiently high concentration to have significant crowding and spatial overlap of the polymer chains have the property of slowing the diffusion of other co-dissolved molecules. Hyaluronan has been suggested as an adjuvant for slowed diffusion of therapeutic agents (e.g., for use in joints, wounds, ulcers, burns, etc.).

Cell Surface Receptor-Mediated Properties. Cell surface receptor interactions may play a role in several of the above applications. It is known that hyaluronan molecular weight influences the cell surface receptor interactions. High molecular weight hyaluronan, bound to the receptors, is characteristic of the healthy physiological environment. In several pathological conditions, hyaluronan is degraded or synthesized at a lower molecular weight. Hyaluronan with a molecular weight of less than approximately 200,000 binds to cell surface receptors in an altered manner, resulting in signaling that leads to expression of genes for proteins that mediate the inflammatory response. Furthermore, small oligosaccharides (containing less than about 50 sugars in a chain) of hyaluronan have still different cell signaling properties. Oligosaccharides can induce cell death in tumor cells, make tumor cells more sensitive to chemotherapy drugs, induce blood vessel growth, rescue cells from inflammation, and other seemingly conflicting activities. Each of these biological activities appears to depend on a particular chain size. The mechanisms for these effects, and the reasons for the molecular weight dependence, remain to be explained in detail. Products under development include hyaluronan fragments of specific sizes.

Noncovalent Complexes of Unmodified Hyaluronan with Other Agents

A gel-like solution of the $Fe^{3+}$ salt of hyaluronan was developed for use as an antiadhesion material in pelvic surgery, but was withdrawn. A $Cu^{2+}$ salt of hyaluronan was suggested to aid cell adhesion (Barbucci et al., 2000). $Ca^{2+}$ was used to enhance the effect of hyaluronan in slowing the diffusion of the drug doxycycline. A mixture of hyaluronan with $KI_3$ (which may be weakly complexed together) has been proposed for use in wound healing (Frankova et al., 2006).

Complexes of hyaluronan with positively charged drug molecules, stabilized by both electrostatic and hydrophobic interactions, were suggested for use in drug delivery (Santos et al., 2007).

Complexes of the negatively charged hyaluronan with positively charged polymers (chitosan, polylysine, etc.) are generally insoluble or slowly soluble in physiological media. The polyelectrolyte complexes have been prepared as fibers, microspheres, surface coatings, and multilayer composite materials. The layers can also be crosslinked into microshells (Lee et al., 2007a). The intended uses of these materials include anti-coagulant blood vessel wall coatings to combat re-stenosis (Thierry et al., 2003a), cell culture substrates, tissue engineering scaffolds, and controlled drug release agents. Another tissue engineering matrix composed of hyaluronan-chitosan fibers embedded in a more soluble mixture of hyaluronan and chitosan has been proposed. Hyaluronan has also been complexed with polypyrrole to produce an electrically conducting material to stimulate nerve tissue regrowth. In that case, the intended role of the hyaluronan is slow degradation to release bioactive oligosaccharides.

Insoluble or slowly soluble electrospun fibers of hyaluronan, hyaluronan/gelatin mixtures, or hyaluronan crosslinked by poly(ethylene glycol) have been prepared for use in tissue engineering (Um et al., 2004; Li et al., 2006; Ji et al., 2006a, 2006b).

Hyaluronan can be infused into a porous three-dimensional bone graft scaffold composed of polylactic acid, to facilitate cellular infiltration.

Soluble Chemical Derivatives of Hyaluronan

Hyaluronan can be derivatized by a number of procedures, examples of which are described in the publications of Vercruysse and Prestwich, 1998, Prestwich et al., 1998; Luo and Prestwich, 2001, and Shu and Prestwich, 2004.

The protein superoxide dismutase has been chemically attached to hyaluronan for use as an anti-inflammatory agent (Sakurai et al., 1997).

Chemical attachment of small molecule therapeutic agents such as
  doxorubicin or other antiproliferatives (Luo and Prestwich, 1999; Rosato et al., 2006),
  methylprednisolone or other steroid esters (Taglienti et al, 2005),
  diclofenac or other non-steroidal anti-inflammatory agents,
  bupivacaine or other analgesics,
  nitric oxide for the inflammatory phase of wound healing (DiMeo et al, 2006),
  other therapeutic molecules
makes hyaluronan an effective pro-drug, primarily targeting the carried drug to tumors or the liver, because these tissues have high contents of the cell surface receptor for hyaluronan.

High molecular weight hyaluronan has been coupled with diethylenetriamine pentaacetic acid (DTPA) (Gouin and Winnik, 2001), where the DTPA groups are used to bind radionuclides for use in cancer therapy, and the hyaluronan targets the complex to tumor cells. Low molecular weight hyaluronan has been coupled to DTPA to chelate $Gd^{+3}$, and is useful as an imaging contrast agent, targeted to cell surface receptors in tumor tissue. Hyaluronan with attached carborane, targeted to tumor cells, may be employed as an agent in boron neutron capture therapy (DiMeo et al, 2007).

Hyaluronan with covalently attached β-cyclodextrin molecules is able to complex and protect small guest molecules such as ibuprofen (Chariot et al., 2006).

Hyaluronan has been sulfated to form an anticoagulant polymer with reduced platelet attachment (Crescenzi et al, 2002).

Deacetylated hyaluronan, which is a soluble polymer with both cationic (positive) and anionic (negative) groups, bound anionic alginate to form an insoluble polyelectrolyte complex.

Attachment of lipids to hyaluronan (Dan et al., 1998; Schnitzer et al., 2000; Oohira et al., 2000; Ruhela et al., 2006) allows the polysaccharide to be anchored in lipid bilayers, to bind low density lipoproteins, or to affect cell behavior on substrates.

Synthetic polymers and polypeptides can be grafted onto the hyaluronan polymer (or vice versa), providing a variety of elaborate tree-like assemblies, with functionality based on the attached branches. Some of these graft copolymers are suggested for use in DNA delivery.

Hyaluronan derivatized with reactive pendant groups that can become crosslinked following photochemical activation have been prepared for in situ crosslinking. (see chemically crosslinked hyaluronan gels, below).

Insoluble or Slowly Soluble Derivatives of Hyaluronan

Hyaluronan fully esterified by ethyl or benzyl groups is insoluble. This material has proven to be highly biocompatible, and has been manufactured as anti-adhesion fabrics, sponges, membranes, skin grafts, and tissue engineering scaffolds. It is successfully used in general surgical applications, especially abdominal surgery, to minimize post-operative adhesions. It is also used in repair of the tympanic membrane of the ear, and in sinus surgery. The material may also contain fibronectin or other growth factors. Tissue engineering materials may be seeded with cells.

Bioactive materials can also be built on the solid benzyl ester of hyaluronan, coated with two types of multilayers: (poly(dimethyldiallylammonium chloride) and poly(styrene sulfonate), followed by poly-D-lysine and an antibody to TGF-β1 (Pastorino et al., 2006).

Hyaluronan modified with a positively charged carbodiimide, mixed with a similarly modified carboxymethyl cellulose, forms a polyelectrolyte complex, in which the positively charged pendant groups and the negatively charged carboxyl groups form electrostatic interactions. This material is successfully used as an anti-adhesion film for surgical applications. It is also used as a coating on polypropylene mesh for surgical applications (see below, for surface attachment applications).

Physical Gels of Hyaluronan

Hyaluronan can form gels by an unknown mechanism, after heating and cooling procedures (Takahashi et al., 2000; Fujiwara et al., 2000). The inter-chain associations, functionally similar to chemical crosslinks, may be aggregates that would be redissolved only over a long time period.

Hydrophobic alkyl groups can be attached to hyaluronan to form amphiphilic polymers that associate strongly to form reversible physical gels (Pelletier et al., 2000; Dausse et al., 2003; Huin-Amargier at al., 2005; Mlčochova et al., 2006; Mráček et al., 2007).

Attachment of lactic acid oligomers to a mixed salt (Na+, cetyltrimethylammonium) form of hyaluronan leads to gel formation (Pravata et al., 2008).

Host-guest interactions lead to formation of a gel when hyaluronan having bound β-cyclodextrin is mixed with hyaluronan having a bound acylurea. The pendant groups complex together, linking the polymer chains noncovalently (Šoltés and Mendichi, 2003; Šoltés at al., 2004).

Chemically Crosslinked Hyaluronan Gels

Crosslinked gels of hyaluronan have found numerous applications. The gels may be used in the form of sieved particles, spherical microparticles, membranous films, or sponges. In some cases, the gel is employed as a long residence form of the polymer. Thus it is used in preparations for treatment of joint pain and cartilage defects (Balazs et al., 1993; Barbucci et al., 2002a; Balazs, 2004; Asari, 2004; Miller and Avila, 2004), where the turnover of soluble hyaluronan is rapid. Similarly, antiadhesion or wound dressing films formed from crosslinked material remain in place longer, with lifetimes controlled to match the physiological need, such as medium-term prevention of post-surgical adhesions in abdominal or nasal surgery. It can also serve a long term space-filling function in tissue augmentation, for use in vocal fold tissue, urinary sphincter, or facial wrinkles or scars. In other cases, the main function of the gel is to serve as a reservoir of slowly released hyaluronan fragments having angiogenic or chondrogenic effects. Because hyaluronan degradation is aided by reactive oxygen species generated in inflammation, the gels are plausibly termed inflammation-responsive materials.

The hyaluronan crosslinks in the gels can be created using a wide variety of chemical agents such as bisepoxides, divinylsulfone, glutaraldehyde (Crescenzi et al, 2003), carbodiimides, alkyl diamines (Barbucci et al., 2000b, 2000c, 2006), thiols, cystamine (Lee et al., 2007a), photosensitive groups, etc. as reactive species, or via the elegant Ugi and Passerini multicomponent condensations (de Nooy et al, 2000). Alternatively, the hyaluronan may be treated in a manner that results in ester formation between carboxyl groups and alcohol groups on separate hyaluronan chains. The hyaluronan component may be in its native form, or subjected to modifications such as esterification, sulfation (Barbucci et al., 2000b, 2006), oxidation of hydroxymethyl groups with subsequent esterification, attachment of functional amines (Crescenzi et al 2003), or N-deacetylation followed by modifications of the amino group such as sulfation (Crescenzi et al, 2002a). The gel porosity can be altered by treatment with bubbled $CO_2$ (Barbucci and Leone, 2004; Leone et al., 2004).

The porous hyaluronan gels can be loaded with metal ions (Giavaresi et al., 2005), drugs (Barbucci et al., 2005a), proteins, or other therapeutic agents for slow release, resulting from inhibition of the diffusion of the added species. Tissue engineering matrices of hyaluronan gel may be seeded with cells, or crosslinked using the facile click-chemistry in the presence of cells (Crescenzi et al, 2007).

Residual activated but incompletely reacted groups can be used to covalently attach drugs or other agents, making the hyaluronan gel a drug carrier. In these cases, the drug release must follow degradation of the hyaluronan or cleavage of the attachment.

Crosslinked matrices of hyaluronan with collagen protein are proposed for tissue engineering (Crescenzi et al 2002b).

In some cases, the mode of hyaluronan gel interaction with added species can be either simple mixture or a covalent attachment. Hyaluronan gels have been proposed to carry cell-adhesive peptides or proteins such as antibodies, growth factors, or thrombin. They may carry enzyme inhibitors such as phospholipase A2 inhibitor or anti-inflammatory vitamin E succinate. They may be used to provide slow release of siRNA to interfere with the synthesis of selected proteins.

Hyaluronan Attached to Surfaces

Hyaluronan-coated articles have been created to improve biocompatibility, especially for surfaces in contact with blood, and to provide specific desirable attributes such as lubricity, reduced nonspecific protein adsorption, and reduced tissue and bacterial cell adhesion (Kito and Matsuda, 1996; Hoekstra, 1999; Barbucci et al. 2003a; Morra, 2005; Taglienti et al, 2006). Specific adhesion of cells expressing hyaluronan receptors can also be achieved, and adhesion of other cell types can be mediated by attachment of cell adhesion-mediating peptides or proteins. The hyaluronan may be physically coated (adsorbed) on the underlying material, or, much more commonly, may be chemically crosslinked to it. The chemical crosslinks may be electrostatic or covalent in nature.

Physical Attachment of Hyaluronan to Surfaces

Hyaluronan has a weak tendency to physically adsorb onto surfaces. Plastic (mostly modified polystyrene) tissue culture and microtiter plates can adsorb hyaluronan from aqueous solutions (especially, 0.1 M sodium bicarbonate) with sufficient stability that the attachments can be exploited in assays for specific binding proteins or cells expressing the CD44 or RHAMM receptors (Delpech et al., 1985; Goetinck et al., 1987; Barton et al., 1996; Catterall et al., 1997; Lokeshwar and Selzer, 2000; Lesley et al., 2002). An important aspect of these weak attachments is the availability of the hyaluronan for specific binding interactions with other species. A drawback of adsorption as an approach to immobilization is the lack of long term stability. Some increase in stability can be obtained if the hyaluronan is dried on the surface (Park and Tsuchiya, 2002). The same effect of drying was observed for hyaluronan adsorbed to silica that had been pretreated with oxygen plasma to add —OH groups (Khademhosseini et al., 2004; Suh et al., 2005; Fukuda et al., 2006). In the latter reports, the molecular weight of the hyaluronan was found to be an important consideration, possibly because high molecular weight chains should have an increased tendency to form interacting networks on the surface during the drying process (Cowman and Matsuoka, 2005). Adsorption of hyaluronan to surfaces can also be exploited to form patterned surfaces, using microcontact printing or molding approaches (Khademhosseini et al., 2004; Fukuda et al., 2006). Adsorption to silica and poly(hydroxyethyl methacrylate) was acceptable, but was poor to polystyrene unless the surface was pre-treated with oxygen plasma (Suh et al., 2004). Patterned hyaluronan on silica resists protein or cell adhesion, whereas bare silica sections will bind fibronectin and cells. Subsequent coating of the hyaluronan sections with polylysine or collagen can be employed to form adhesive surfaces for a second cell type, thus allowing patterned co-cultures to be created (Khademhosseini et al., 2004; Fukuda et al., 2006).

Hyaluronan can be adsorbed on a polyurethane surface that has been previously coated with a gelatin layer. Photo-crosslinking of the hyaluronan layer stabilizes it for use as an anti-thrombotic coating for the luminal surface of a narrow vascular graft (Kito and Matsuda, 1996).

Hyaluronan can be entrapped at a polyethylene surface in a microcomposite structure for use in joint replacement implants. The material is formed by allowing a silyl derivative of hyaluronan to penetrate a porous polyethylene preform, crosslinking it in place, hydrolyzing the silyl groups, adding a surface coat of hyaluronan, crosslinking that layer, and finally compressing the material to collapse the porous structure into a hyaluronan-coated solid with excellent wear properties (Zhang et al., 2006, 2007).

Covalent Attachment of Hyaluronan to Metallic Surfaces

Stable immobilization of hyaluronan on surfaces is achieved by covalent attachment of the polysaccharide, either directly to the surface, or via attachment to a bridging adhesive polymer layer.

Metal substrates (stainless steel, nickel titanium, titanium) are of interest, with respect to medical uses as stents, guide wires, dental and orthopedic implants, sensors, or other devices. The strategy for attachment of hyaluronan is to generate functional groups on the metal surface, and then employ appropriate chemistry to link the hyaluronan molecules.

Functional group generation on metal surfaces can be achieved by methods such as 1) formation of an oxide layer on the metal surface, then reaction with a functional silane derivative (U.S. Pat. No. 5,356,433; U.S. Pat. No. 5,336,518; Pitt et al., 2003); 2) plasma treatment in the presence of air, argon, acetaldehyde, allylamine, hexafluorobutylmethacrylate, etc., to generate groups such as aldehydes and amines on the metal surface (U.S. Pat. No. 5,356,433; U.S. Pat. No. 5,336,518; Thierry et al., 2004; Morra et al., 2006); 3) dip coating with an adhesive acrylic polymer bearing isocyanate groups (U.S. Pat. No. 5,037,677); 4) dip coating with polyethyleneimine having free amine groups (Thierry et al., 2003b); 5) dip coating with dopamine to form an adhesive polymer layer having quinone-like properties (Lee et al., 2007b).

The covalent attachment of hyaluronan to these modified surfaces can be achieved by approaches such as 1) reaction with surface amine groups via carbodiimide activation of hyaluronan carboxyl groups (Larsson, 1987; U.S. Pat. No. 5,356,433; U.S. Pat. No. 5,336,518; Thierry et al., 2004; Morra et al., 2006); 2) reaction of surface amines with the reducing end aldehyde function of short hyaluronan chains to form a Schiff base which is subsequently reduced (U.S. Pat. Nos. 4,613,665 and 4,810,784); 3) reaction of surface aldehyde groups with an adipic dihydrazide derivative of hyaluronan (Pitt et al., 2003); 4) urethane link formation between surface isocyanate groups and hydroxyl groups of hyaluronan (U.S. Pat. No. 5,037,677); 5) attachment of surface quinone-like groups of polydopamine with thiol or amine derivatives of hyaluronan (Lee et al., 2007a).

The hyaluronan-derivatized metal surfaces can differ in the degree to which the hyaluronan can bind proteins, cells, etc. The surfaces are generally intended to be resistant to nonspecific adsorption of proteins or cells. There is special interest in surfaces that do not bind fibrinogen or platelets. Cells expressing CD44 can adhere to some surfaces. There is currently insufficient knowledge about the best approaches to control the frequency of hyaluronan attachments to the surface, and thus control the degree to which the surface-bound hyaluronan is available to show specific binding interactions with proteins or cells.

One special metallic surface that is easily and specifically reacted for attachment of hyaluronan is gold. Gold nanoparticles were reacted with hyaluronan bearing thiol groups, previously attached via carbodiimide activation of carboxyl groups and coupling to cystamine, followed by reduction of the pendant disulfide to a thiol (Lee et al., 2006). Many small nanoparticles could be linked to a single long polymer of hyaluronan, resulting in a necklace of gold nanoparticles.

Covalent Attachment of Hyaluronan to Polymeric Surfaces

Attachment of hyaluronan to polymeric substrates has also been widely investigated for use in implants, catheters, etc. Among the polymeric substrates investigated for hyaluronan attachment are polystyrene, poly(methyl methacrylate), silicone rubber, poly(tetrafluoroethylene) [Teflon], poly(ethylene terephthalate), polyurethane, poly(vinyl alcohol), polyethylene, and polypropylene. There are patents dating from the mid 80's on hyaluronan-modified polymers (e.g., Balazs, Leschiner, and coworkers patents 1984, 1985; Beavers and Halpern patents 1987, 1989, 1991; Larm patents 1986, 1989). There are a number of strategies used to form stable covalent attachments of hyaluronan to surfaces.

The polymer surface may be treated with a plasma to provide appropriate functional groups such as amines. For example, commercially available aminated polystyrene materials may be reacted with carbodiimide activated hyaluronan (Frost and Stern, 1997) or reacted first with an azide-bearing group then photocrosslinked to hyaluronan (Joester et al., 2006). Ammonia plasma treatment can be used to aminate the surface prior to photo-immobilization of an azidophenyl hyaluronan derivative (Barbucci et al., 2005b). Ammonia plasma treatment followed by reaction with succinic anhydride produces surface carboxyl groups that can be reacted with an adipic hydrazide derivative of hyaluronan (Mason et al., 2000). The surface can be activated by air plasma treatment, reaction with polyethyleneimine, and subsequently reacted with carbodiimide-activated hyaluronan (Morra and Cassinelli, 1999; Cassinelli et al., 2000). The substrate may be activated by plasma polymerization of acetaldehyde, then Schiff base formation with poly(allylamine), followed by reaction with carbodiimide-activated hyaluronan (Thierry et al., 2004).

Poly(ethylene terephthalate) can be oxidized in base at high temperature to form carboxyl groups, then coated with a cationic polymer prior to hyaluronan (Liu et al., 2006).

Hyaluronan can be photochemically immobilized on silicone rubber, after initial immobilization of a polyacrylamide layer, then a hyaluronan layer, both linked covalently using the 4-benzoyl benzoic acid derivatives (DeFife et al., 1999).

Hyaluronan can also be covalently attached to more adhesive polymer layers that are strongly attached to the substrate. Coating PMMA with an acrylic polymer bearing isocyanates can be used to attach hyaluronan via urethane linkages to its hydroxyl groups (Lowry and Beavers, 1994; U.S. Pat. Nos. 4,663,233; 4,801,475; and 5,037,677). Dopamine coating on polymeric surfaces leads to a polymeric coating containing quinone-like groups to which thiol or amine-derivatized hyaluronan can attach (Lee et al., 2007b).

As for the attachment of hyaluronan to metallic surfaces, the frequency of attachment points of the hyaluronan molecule to polymeric surfaces can affect its ability to interact with proteins or cells. When attachment points are closely spaced, the hyaluronan can be resistant to degradation by hyaluronidase, and thus show long term stability (Lowry and Beavers, 1994). In most published studies, hyaluronan-coated polymer materials are reported to be anti-adhesive to most proteins and cells, but show specific adhesion of CD44+ cells.

Covalent Attachment of Hyaluronan, to Silica Surfaces

Hyaluronan can be covalently attached to glass (silica). Applications of the coated silica are primarily in cell culture. Many silica surfaces modified with hyaluronan are notable for inhibiting cell adhesion.

Most of the silica-based surfaces are derivatized via silane chemistry. If the silica is reacted with an aminosilane which becomes covalently attached as a monolayer presenting amino groups, then hyaluronan that has an azidophenyl group can be photo-immobilized and even micropatterned on the surface using a photolithographic mask procedure (Barbucci et al., 2003; Chiumiento et al., 2007). A surface bearing aminosilanes can also be reacted with carboxyl groups of hyaluronan via carbodiimide coupling (Albersdörfer and Sackmann, 1999; Ibrahim et al., 2007; Joddar et al., 2007). Fluoroalkylsilanes on silica can be photo-crosslinked with hyaluronan bearing azidoaryl groups (Wang et al., 2006). Chlorotrimethylsilane on silica provides a hydrophobic surface that can adhere to polylactic-co-glycolic acid), allowing subsequent coating with polyethyleneimine and finally attachment of hyaluronan by carbodiimide chemistry (Croll et al., 2006). It is also possible to make a silane-bearing derivative of hyaluronan, which can directly react with the bare silica surface (Pasqui et al., 2007). This latter method may be preferred because fewer of the hyaluronan carboxyl groups are derivatized, and therefore remain able to participate in hyaluronan interactions with other species such as proteins. Hyaluronan attached to silica by these procedures does not promote cell adhesion (Barbucci et al. 2003b; 2005b; Pasqui et al., 2007; Chiumiento et al., 2007).

An alternative approach to silica surface modification is the use of an ethylene plasma to create a hydrophobic surface, oxidation of that layer in an air plasma, followed by coating with polyethyleneimine. The amine groups can then be reacted with hyaluronan carboxyl groups via carbodiimide chemistry (Morra et al., 2003).

Covalent Attachment of Hyaluronan to Quantum Dots

Quantum dots of CdSe/ZnS, with attached ligands containing terminal carboxyl groups, have been derivatized by carbodiimide-mediated reaction with amine groups on an adipic acid dihydrazide derivative of hyaluronan (Kim et al., 2008).

Electrostatic Attachment of Hyaluronan to Surfaces

Electrostatic immobilization of hyaluronan has also been widely investigated. A metal or silica surface may be precoated with cationic polymers such as polyethyleneimine, chitosan, or polylysine prior to electrostatic attachment of hyaluronan (Morra et al., 2003; Burke and Barrett, 2003; Thierry et al. 2003b; Hahn and Hoffman, 2005; Tezcaner et al., 2006). Gold-coated silica substrate can be reacted with carboxylated alkylthiols to form an anionic monolayer, coated with cationic polyethyleneimine, and then electrostatically linked to hyaluronan (Kujawa et al., 2005). Nanospheres of poly-ε-caprolactone can be formed in the presence of a cationic surfactant such as benzalkonium chloride, and then coated with an electrostatically bound hyaluronan layer (Barbault-Foucher et al., 2002).

Several research groups have worked extensively on the formation of coatings that are formed by laying down alternating electrostatically-bound layers of hyaluronan and a cationic polymer. The coating is sometimes called a polyelectrolyte multilayer. The technique is frequently referred to as layer-by-layer assembly. The layers are not perfectly smooth, as the polymers have a tendency to form islands of adsorbed material, and thus there can be extensive interpenetration of the anionic and cationic polymer layers. The coatings can be used to carry bioactive agents (see below).

One research group has extensively investigated polyelectrolyte multilayers composed of hyaluronan and either polylysine or chitosan, usually deposited directly on glass or quartz substrates (Picart et al., 2001, 2002, 2005; Richert et al., 2004a, 2004b, 2004c, 2006; Collin et al., 2004; Zhang et al., 2005; Etienne et al., 2005; Schneider et al., 2006, 2007a, 2007b; Francius et al., 2006; Tezcaner et al., 2006). Using a robotic coating device, the assemblies could be built with many (ca. 20-100) layers. In some studies, the coatings were crosslinked after deposition. The stiffness parameters of the coatings were investigated by nanoindentation of a colloidal probe tip in an atomic force microscope, or by piezo-rheometer. It was observed that crosslinking increased stiffness and simultaneously increased cell adhesion. The crosslinked films were also resistant to enzymatic degradation. The crosslinked films were proposed to be useful in delivery of drugs such as paclitaxel or diclofenac (see below). Most recently, assemblies of hyaluronan with collagen protein, and hyaluronan with an aminated derivative of hyaluronan were prepared and characterized.

Another research group has extensively studied polyelectrolyte multilayers formed with hyaluronan and chitosan (Thierry et al., 2003a, 2003b, 2004, 2005; Kujawa et al., 2005, 2007). The coatings were immobilized on several different substrates, including polyethyleneimine on metal; polyethyleneimine on a carboxyalkylthiol-derivatized gold on silica; quartz; and artery walls.

Additional groups have provided other very interesting and creative studies of polyelectrolyte multilayers containing hyaluronan. Liu et al. (2006) prepared a hyaluronan-chitosan multilayer film for use in coating poly(ethylene terephthalate) in a microfluidic device. Veerabadran et al. (2007) built a hyaluronan-polylysine multilayer coating that was able to encapsulate and protect stem cells. Lee at al. (2007b) devised a spherical microshell composed of a crosslinked hyaluronan-polylysine multilayer, formed initially around a disulfide-crosslinked hyaluronan hydrogel microsphere that was liquified by reduction and allowed to diffuse out. The redox properties of polyelectrolyte multilayers composed of hyaluronan and the globular protein myoglobin have been studied as models for novel coatings for biosensors, bioreactors, and other biomedical devices (Liu and Hu, 2006; Lu and Hu, 2007).

Hyaluronan Attached to Supported Lipid Bilayers or Liposomes

Supported lipid bilayers can be used to immobilize hyaluronan. Sengupta et al. (2003) used a supported bilayer, deposited on glass, and formed with a small fraction of lipid containing a nickel-chelating head group. Using histidine-tagged p32 protein that binds hyaluronan, the polysaccharide was then bound noncovalently to the surface. Benz et al. (2004) used a lipid bilayer on mica to attach hyaluronan in several ways. A lipid carrying a biotin group allowed a layer of streptavidin to be bound to the bilayer, and then biotin-labeled hyaluronan could be noncovalently bound to the surface. They also bound hyaluronan covalently to an amine-bearing lipid, using carbodiimide activation of hyaluronan carboxyl groups. The bound hyaluronan layer could be subsequently crosslinked to form a stable coating. Richter et al. (2007) used the biotin-streptavidin-biotin technique to attach hyaluronan to a lipid bilayer, but using hyaluronan end-labeled with biotin gave a better result than the approach of Benz et al. (2004).

Margalit and coworkers pioneered the use of liposomes with bound hyaluronan. Attachment of hyaluronan via carbodiimide activation of carboxyl groups and reaction with amine-bearing lipids resulted in stable hyaluronan-coated lipid vesicles (U.S. Pat. No. 5,401,511; Yerushalmi et al., 1994; Yerushalmi and Margalit, 1998; Peer and Margalit, 2000). The interior of the lipid vesicles could be loaded with growth factors for use in wound healing, or any of a number of drugs. The hyaluronan coat provided adhesion to certain types of cells expressing CD44 receptors, for extended residence time at the wound site. The hyaluronan coat also provided protection of the liposome during lyophilization and reconstitution procedures that allow long term storage of liposome-based therapeutics (Peer et al., 2003). Szoka and coworkers (Eliaz and Szoka, 2001; Eliaz et al., 2004a, 2004b) produced liposomes with hyaluronan oligosaccharides bound to amine-bearing lipids via reductive amination. These liposomes could carry the chemotherapeutic agent doxorubicin, and target it to tumor cells overexpressing the CD44 receptor. The hyaluronan-coated liposomes provided higher potency in tumor cell cytotoxicity, and lower toxicity to other cell types. Peer and Margalit (2004a, 2004b) further established the utility of high molecular weight hyaluronan as a targeting agent for liposomes carrying anti-tumor agents (doxorubicin, mitomycin C). Another use of hyaluronan-coated liposomes, proposed by Margalit and coworkers (Fischer et al., 2005), was as a carrier of an enzyme to protect against nerve toxin organophosphates. It should be noted that the hyaluronan coating in all of these liposome studies was not involved in binding or sequestering the bioactive agents, which were encapsulated within the liposomes.

Surface-Immobilized Hyaluronan as a Carrier of Bioactive Agents

Layer-by-layer assemblies of hyaluronan and chitosan or hyaluronan and polylysine have been suggested as carriers of bioactive agents such as arginine (Thierry et al., 2003a), sodium nitroprusside (Thierry et al., 2003b), paclitaxel (Schneider et al., 2007b) and sodium diclofenac (Schneider et al., 2007b). The enzyme trypsin, when immobilized on a chitosan layer of a hyaluronan-chitosan multilayer film, was more active in protein digestion than free trypsin (Liu et al., 2006). Basic fibroblast growth factor (bFGF), adsorbed onto a polylysine layer of a hyaluronan-polylysine film, was more effective than free bFGF in aiding adhesion and maintaining differentiation of photoreceptor cells (Tezcaner et al., 2006). Covalent attachment of gelatin to a hyaluronan-chitosan film was used to aid fibroblast adhesion (Croll et al., 2006).

Chemically modified hyaluronan can also be incorporated into a surface coating. DTPA-modified hyaluronan in a coating has been suggested as a carrier of radionuclides to inhibit cell proliferation on stents (Thierry et al., 2004). Hyaluronan can be derivatized with the RGD peptide that mediates cell adhesion, to facilitate integration of an implanted material with surrounding tissue, esp. bone (Pitt et al., 2003). Hyaluronan chemically derivatized with the drug paclitaxel was used with chitosan to form a multilayer (Thierry et al., 2005). Sulfated hyaluronan, with nearly 90% of the hydroxyl groups sulfated, has also been extensively studied in attachment to surfaces. The sulfated hyaluronan is so significantly modified that its properties are not similar to hyaluronan, but it has excellent anticoagulant activity. It has a variable affinity for cell adhesion, generally being more adhesive than hyaluronan. In complexation with $Cu+2$ ions, it is angiogenic. Barbucci has published a number of reports concerning sulfated hyaluronan on surfaces. (Chen et al., 1997; Magnani et al., 2000, 2004; Barbucci et al., 2000c, 2002b, 2002c, 2003b, 2005c, 2005d; Hamilton et al., 2005; Chiumiento et al., 2007)

Hyaluronan attached to silica has been reported to have altered protein or cell surface interactions relative to free hyaluronan. The altered interactions can be due to the chemical changes in the polymer caused by the procedures used to attach hyaluronan to a surface (e.g., effective loss of carboxyl groups). An example is the binding with apparent conformation change of the protein fibronectin on a surface containing photoimmobilized hyaluronan, where the hyaluronan has lost carboxyl function and has an extreme degree of attachment frequency (Barbucci et al., 2005c). Similarly, fibrinogen adsorbed onto a photoimmobilized hyaluronan surface cannot bind platelets, but fibrinogen can do so if independently covalently attached to the surface (Chiumiento et al., 2007). Serum proteins can adsorb to a surface having photoimmobilized hyaluronan, and some bind strongly enough that a combination of detergent, urea and dithioerythritol is required to release them (Magnani et al., 2004).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is directed to a biocompatible material in the form of a solid, a water insoluble cross-linked gel (polymer) or a liposome, which contains a stable complex of TNF-stimulated gene 6 protein (hereinafter referred to as "TSG-6") and hyaluronan (HA). The present invention includes a stable soluble complex of TSG-6 and HA released from the biocompatible material.

The present invention also represents an improvement over existing hyaluronan biocompatible products that are in solid, gel or liposome form as it combines the anti-inflammatory properties of the TSG-6-HA complex with the anti-adhesive properties of the existing HA biocompatible products.

The present invention further provides an improved method for using a HA-containing biocompatible material to treat in a patient in need thereof a disease, disorder or condition for which the biocompatible material is effective, where the improvement is that HA is stably complexed with TSG-6.

A still further aspect of the present invention is directed to a method for locally inhibiting inflammation by locally introducing the biocompatible material of the present invention into a patient in need thereof.

BRIEF DESCRIPTION OF THE DRAWINGS

FIG. 1A: 2 nM TSG-6 or 2 nM purified IαI were incubated alone or together for 2 hours at 37° C. in Cov-HA or Cov-NH. FIG. 1B: Increasing concentrations of TSG-6 protein were incubated with human plasma diluted 1:1000 in TTBS for 2 hours at 37° C. in Cov-HA. FIG. 1C: 50 nM TSG-6 was incubated with various dilutions of human plasma in TTBS for 2 hours at 37° C. in Cov-HA or Cov-NH. FIG. 1D: Human plasma, diluted 1:10 to 1:1000, was incubated in the presence or absence of 5 nM TSG-6 for 2 h at 37° C. Each data point represents the mean of 6 wells±SE.

FIG. 2A: 50 nM TSG-6 and human plasma diluted 1:1000 was incubated for 2 hours at 37° C. in Cov-HA. Selected wells were then treated with either 6 M guanidine HCL, 6 M guanidine HCl containing 8% LSB, or with 2×SDS-PAGE sample buffer for 15 min. FIG. 2B: Selected wells were then treated with either 6 M guanidine HCl containing 8% LSB (15 min at ambient temperature), 50 mM NaOH (1 h at ambient temperature), or 10 u/ml S. hyalurolyticus HAse (1 h at 37° C. Each data point represents the mean of 6 wells±SE.

FIG. 3A: 5 nM TSG-6 and human plasma diluted 1:1000 in PBS were incubated together in Cov-HA for 2 hours at 37° C. FIG. 3B: 5 nM TSG-6 in PBS was incubated in Cov-HA for 2 hours at 37° C. After washing with TTBS, human plasma diluted 1:1000 in PBS was added to the same wells and incubated for 2 hours at 37° C. Both bound TSG-6 and bound HCs were determined. Each data point represents the mean of 6 wells±SE.

FIG. 4A: 2 nM TSG-6 and 2 nM purified IαI were co-incubated in the absence or presence of 10 mM EDTA. FIG. 4B: 10 nM of TSG-6 in PBS was incubated in the absence or presence of 10 mM EDTA. After washing with TTBS, human plasma diluted 1:1000 in PBS was incubated in the same wells in the absence or presence of 10 mM EDTA. Each data point represents the mean of 6 wells±SE.

FIG. 5A: TTBS, or 10 nM TSG-6 in TTBS was incubated in Cov-HA for 2 h at 37αC. After washing with TTBS, either TTBS or human plasma diluted 1:1000 in TTBS was incubated in the same wells for 2 h at 37° C. Alternatively, 10 nM TSG-6 and plasma diluted 1:1000 in TTBS were co-incubated for 2 h at 37° C. (TSG-6+plasma). FIG. 5B: PBS, or nM TSG-6 in PBS was incubated in Cov-HA for 2 h at 37° C. After washing with TTBS, human plasma diluted 1:1000 in either PBS, 20 mM Tris pH 7.5, 150 mM NaCl, or 20 mM Tris pH 7.5, 500 mM NaCl, or 20 mM Tris pH 7.5, 150 mM NaCl, 0.1% Tween-20, or 20 mM Tris pH 7.5, 500 mM NaCl, 0.1% Tween-20, was incubated in the same wells for 2 h at 37° C. Each data point represents the mean of 6 wells±SE.

DETAILED DESCRIPTION OF THE INVENTION

Figure 1A:
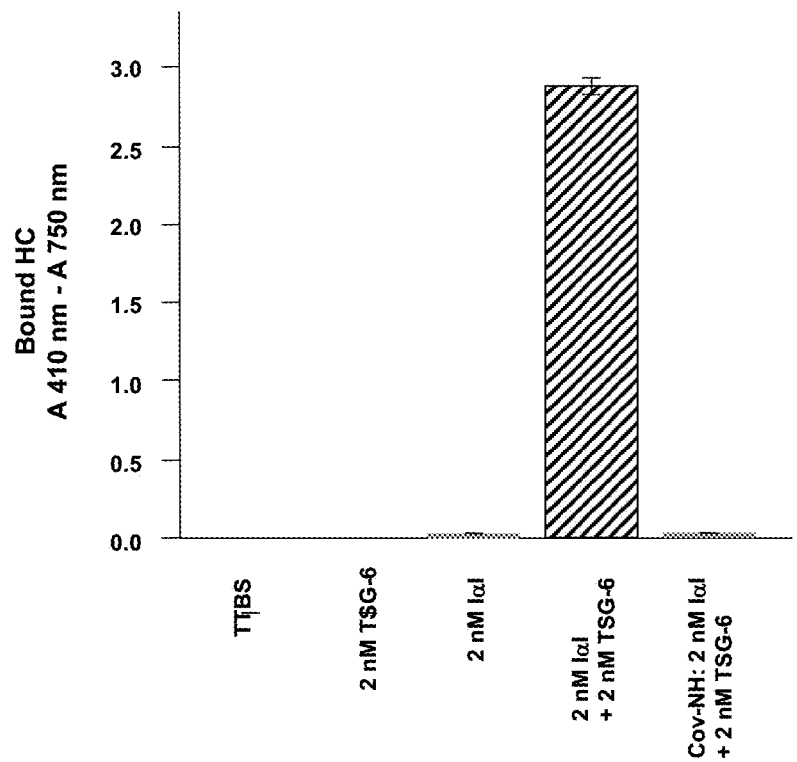
FIGS. 1A-1D are graphs showing TSG-6-dependent binding of IαI HCs to Cov-HA.

Inter-α-inhibitor (IαI), TSG-6 and hyaluronan (HA) participate in a series of complex interactions that are functionally important in inflammation and fertility. Here, the present inventors show in the Example hereinbelow that stable hyaluronan-TSG-6 complexes are able to mediate the subsequent transfer of inter-α-inhibitor heavy chains to surface-bound hyaluronan as well as to free hyaluronan in solution, suggesting that these complexes can simultaneously interact with a second hyaluronan chain. Using a quantitative binding assay to characterize heavy-chain transfer to hyaluronan by free TSG-6 or by preformed hyaluronan-TSG-6 complexes, the present inventors demonstrated that TSG-6 and heavy chains can bind to surface-bound hyaluronan either simultaneously or in a two-step reaction. Interestingly, heavy chain transfer by preformed hyaluronan-TSG-6 complexes and by free TSG-6 are characterized by different ionic strength requirements. The present inventors also provide direct evidence in the Example hereinbelow that, when sufficient hyaluronan is present, the interaction of limited amounts of TSG-6 with inter-α-inhibitor results in the generation of free bikunin, a serine protease inhibitor known to have anti-inflammatory and anti-metastatic activities. Simultaneously, this reaction results in the decrease of inter-α-inhibitor and in the generation of covalent hyaluronan-heavy chain complexes. A decrease of inter-α-inhibitor concentrations in plasma has been observed in sepsis, while the generation of covalent hyaluronan-heavy chain complexes is known to occur in rheumatoid arthritis, two conditions associated with the expression of TSG-6.

Based on the findings of the present inventors, the present invention is directed to a biocompatible material which is in the form of a solid, a cross-linked gel or liposomes and contains a stable complex of TNF-stimulated gene 6 (TSG-6) and hyaluronan (HA).

The term "biocompatible" means that the material is compatible or acceptable for administration or implantation into the body or is in a form that is pharmaceutically acceptable.

The term "hyaluronan" as used herein further encompasses salts and free acids of hyaluronan as well as hyaluronan that has been cross-linked or chemically altered, yet retain its function. These modifications include, but are not limited to, esterification, sulfation, polysulfation, and methylation. Hyaluronan salts include, but are not limited to, sodium hyaluronate, potassium hyaluronate, magnesium hyaluronate, and calcium hyaluronate.

The term "stable" used herein as it relates to a complex of TSG-6 and HA is defined by the resistance of the TSG-6-HA complex to treatment with detergents, dissociating and reducing agents. Specifically, "stable" TSG-6-HA complexes are resistant to treatment with 6M guanidine HCl containing 80 lauryl sulfobetain (3-(Dodecyldimethylammonio)propanesulfonate, Zwittergent®). This treatment is known to break most noncovalent bonds between protein and HA (Mason et al., 1982; Tsiganos et al., 1986) and has been used to test the stability of covalent protein-HA complexes (Yoneda et al., 1990). A TSG-6-HA complex that is referred to as "stable" is also resistant to boiling in reducing SDS-PAGE sample buffer (0.25 M Tris pH 6.8, 2% sodium dodecylsulfate, 5% 2-mercaptoethanol, 10% glycerol).

The TSG-6-HA complex, when bound to a solid surface or contained within a water-insoluble cross-linked gel or contained on or within a liposome is able to transfer the heavy chains of inter-α-inhibitor (IαI), a ubiquitous plasma protein, to surface-bound HA or free hyaluronan (in solution). When used in the biocompatible material of the present invention, TSG-6 protein's biological activities can be applied and maintained locally at a site in the patient, either on the surface of an in-dwelling/implanted device or associated with a biocompatible material, preferably a biodegradable biocompatible material. Because the medical applications of soluble TSG-6 are limited by its short residence time in tissue as a consequence of its elimination with tissue fluid or its local metabolism, the present invention extends the therapeutic utility of TSG-6 by prolonging its ability to locally modify hyaluronan through transfer of IαI heavy chains, thereby focusing the effect of TSG-6 in a defined temporal and spatial manner. The interaction of TSG-6 with IαI at the local site in a patient where the biocompatible material is introduced, particularly in the presence of HA, results in the local release of bikunin, a serine protease inhibitor with anti-inflammatory activities and properties.

When the biocompatible material is present on the surface of a solid medical device that is implantable or in-dwelling (e.g., stents, artificial joints, etc.) in a patient or is transiently introduced into a patient during the course of a medical procedure (e.g., catheters, guidewires, etc.), the complex of TSG-6 and HA preferably forms a coating on such a solid medical device. In addition to coating such a solid medical device with the biocompatible (e.g., nano- and microparticles disclosed in WO 03/015755 and US2004/0241248, etc.) material in the form of a solid, a cross-linked gel or a liposome, the present invention also encompasses a biocompatible material which initially starts out as a solid dry powder of cross-linked HA or of cross-linked mixed polymer of HA and at least one other polymer (i.e., by itself as a solid dry powder or coating the surface of a solid implantable medical device), which when hydrated with a solution containing TSG-6, forms a cross-linked HA or cross-linked HA-containing gel in which the TSG-6-HA complex is a stable TSG-6-HA complex.

Also encompassed by the present invention is a biocompatible material in which the stable complex of TSG-6 and HA is capable of being released from the material in soluble form. This soluble form of the complex of TSG-6 and HA is stable because it was originally formed on a solid, a water insoluble cross-linked gel or a water insoluble liposome, in contrast to complexes of TSG-6 and HA formed in solution.

The stable TSG-6-HA complex may also be used in the present biocompatible material as an injectable gel, wound dressing, nano- or microparticles or liposomes administered by surface application, injection (i.e., parenteral, intra-articular, etc) or implantation. There are many existing hyaluronan-based biocompatible materials that are well-known in the art, such as the representative HA-containing materials disclosed in the above "Description of the Related Art" section, but these materials have limited anti-inflammatory activity. By coupling TSG-6 to such material in the form of a stable complex of TSG-6 and HA, while maintaining the ability of TSG-6 to interact with IαI and transfer the heavy chains of IαI to surface bound HA and to free HA in solution, biocompatible materials are generated that combine anti-adhesive and anti-inflammatory properties. Thus, the addition of TSG-6 in a complex with HA in existing HA-based biocompatible materials is a distinct improvement to the art. Accordingly, the present invention also provides an improved method for using existing HA-based biocompatible material, in the form of a hyaluronan attached to a solid or a liposome, or cross-linked in a cross-linked HA or HA-containing gel, to treat a disease, disorder or condition of which the biocompatible material is effective. The improvement lies in the feature of HA in the existing biocompatible material being stably complexed with TSG-6.

The biocompatible material of the present invention is suitable for use to inhibit or treat various inflammatory pathologies, including but not limited to intra-articular treatment of arthritic disease, inhibiting adhesion formation between internal wound surfaces after surgery, minimizing pathological changes between tissue surfaces and in-dwelling devices, such as catheters, stents, etc., and providing an anti-inflammatory effect in combination with the wound-healing promoting effects of HA.

The present invention further provides a method for locally inhibiting inflammation (at a local site) in a patient. This method involves introducing the biocompatible material locally into a patient in need thereof, i.e., by implanting or locally administering (i.e., injecting nano- or microparticles, cross-linked HA-containing gels or liposomes) to a local site in the patient.

The patient is preferably a human patient but may include other mammals such as dogs, cats, and horses. It is intended and preferred that the TSG-6 protein is native to the mammal (naturally occurring in the mammalian species) which is to be treated with the TSG-6-HA complex-containing biocompatible material. Besides the human TSG-6 sequence (SEQ ID NO:1) and allelic variants that have 99% nucleotide sequence identity (GenBank accession nos. AJ421518.1 and AJ419936.1) to SEQ ID NO:1, the TSG-6 sequence has been characterized in dog (SEQ ID NO:2; GenBank accession no. XM533354.2), horse (SEQ ID NO:3; GenBank accession no. NM 001081906.1), orangutan (GenBank accession no. AC188102.1), mouse (GenBank XM001473344.1), rat (GenBank accession no. AF159103.1) and opossum (GenBank accession no. XM001365235.1) among a number of others. TSG-6 protein from different mammalian species have high sequence homology/identity with each other (i.e., from 82% sequence identity at the nucleotide level between human and rat to 90% with human and horse; and greater than 90% amino acid sequence identity between human TSG-6 and mouse, rabbit and rat TSG-6). This is not surprising since the activity of TSG-6 protein does not appear to be species-specific but is able to exert its activity across species. Consequently, while the TSG-6 is preferably native to the mammalian species which is to be treated by the biocompatible material containing a stable complex of TSG-6 and HA, it may be a non-native TSG-6 protein from a different mammalian species or it may suitably be a variant of the native TSG-6 in which one or more, preferably no more than five, amino acid residues are substituted by residues that appear in TSG-6 from other species at nonconserved residue positions.

Having now generally described the invention, the same will be more readily understood through reference to the following examples which are provided by way of illustration and are not intended to be limiting of the present invention.

Example 1

The goal of the study in this Example was to evaluate the role of free TSG-6 and of surface-bound HA-TSG-6 complexes in the transfer of HCs from IαI in plasma to HA, using a quantitative assay system. The simultaneous binding of TSG-6 and HCs to surface-bound HA and the transfer of HCs to surface-bound or free HA in a two-step reaction by preformed HA-TSG-6 complexes were investigated. Distinct sets of products were found to be formed after binding of TSG-6 and HC transfer to HA in solution or to solid-phase HA. The scale of HC transfer from IαI in plasma to HA in the presence of added TSG-6 suggests that TSG-6-mediated HC transfer is the major mechanism for the generation of HA-HC complexes and, simultaneously, may significantly contribute to the decrease of IαI in plasma and to the generation of free bikunin, a serine protease inhibitor with anti-inflammatory properties.

The abbreviations used herein are: Cov-HA, Covalink-HA; Cov-NH, Covalink-NH; EDC, N-ethyl-N'-(3-dimethylaminopropyl) carbodiimide; FBS, fetal bovine serum; GAG, glycosaminoglycan; HA, hyaluronan; HABP-bio, biotinylated HA binding protein; IαI, inter-α-inhibitor; LSB, lauryl sulfobetain; SE, standard error; pNPP, p-nitrophenyl phosphate; sulfo-NHS, N-hydroxysulfosuccinimide; TBS, Tris-buffered saline; TSG-6, TNF-stimulated gene 6 protein; TTBS, TBS containing 0.1% TWEEN-20.

Materials and Methods

Reagents. Covalink-NH plates were purchased from Nunc, sulfo-NHS from Pierce, and EDC was purchased from Sigma. HA from rooster comb was purchased from Sigma and bacterial HA was obtained from Lifecore Biomedical, both of which were used for coupling to Cov-NH. Equivalent results were obtained with Cov-HA prepared with rooster comb HA and bacterial HA. EAH-Sepharose was purchased from GE Healthcare, Piscataway, N.J. Hyaluronidase from *Streptomyces hyalurolyticus* and biotinylated hyaluronan binding protein (HARP-bio) were purchased from Associates of Cape Cod, Falmouth, Mass. Select HA™ 30 kDa was purchased from Hyalose L.L.C. (Oklahoma City, Okla.). Human plasma was obtained from the blood bank of the NYU Medical Center. Rabbit anti-IαI was from Dako and is HC specific, i.e., it recognizes free HCs but it does not recognize bikunin (data not shown). The rabbit anti-TSG-6 antibody was raised against native recombinant TSG-6 and has been described earlier (Mindrescu et al., 2005). The rabbit anti-bikunin antibody was generated and provided by Jan Enghild and Christian Sanggaard, University of Aarhus, Denmark.

Biotinylated goat anti-rabbit Ig was from Dako (Glostrup, Denmark) and streptavidin-alkaline phosphatase conjugate was from Invitrogen (Carlsbad, Calif.). The alkaline phosphatase substrate was p-nitrophenyl phosphate (Sigma, St. Louis, Mo.) for solution assays and BCIP/NBT from Bio-Rad for immunoblots. PDVF membrane for immunoblotting (Immobilon P) was from Millipore (Billerica, Mass.).

TSG-6 protein. TSG-6 protein was expressed in BTI-TN-5B1-4 insect cells after infection with recombinant nuclear polyhedrosis virus (baculovirus) and purified as described (Wisniewski et al., 1994 and 2005).

Purified IαI. IαI was purified from human plasma as described previously (Wisniewski et al., 1996).

Coupling of HA to Covalink-NH plates and BAH-Sepharose.

HA was coupled to Covalink-NH plates as described (Wisniewski et al., 2005; and Frost et al., 1997). In brief, HA solution containing sulfo-NHS was added to the wells of Cov-NH plates. After addition of EDC, the plates were incubated for 2 h at room temperature and overnight at 4° C. Thereafter, the plates were washed extensively with 2 M NaCl and blocked with 0.2% casein in TTBS.

Coupling of HA to EAH-Sepharose was carried out similarly to the coupling of HA to Cov-NH. HA at 0.55 mg/ml in a 22.2% (v/v) suspension of EAH-Sepharose was incubated with 0.89 mM sulfo-NHS and 0.36 mM EDC in H2O for 2 h at room temperature and overnight at 4° C. under constant movement. Thereafter, the HA-sepharose was washed with an at least 10-fold volume of 2 M NaCl.

TSG-6 binding assay and HC transfer assay using HA immobilized to Covalink. The assay for TSG-6 binding to HA was carried out as described (Wisniewski et al., 2005). To determine HC transfer, TSG-6 at the indicated concentration was mixed with human plasma at the indicated dilution, usually 1:1000, in TTBS (TTBS: 20 mM Tris pH 7.5, 500 mM NaCl, 0.1% TWEEN-20) and co-incubated in wells of Cov-HA plates for 2 h at 37° C. (100 µl/well). After washing 3 times with 200 µl. of TTBS, the wells were incubated with a 1:2000 dilution (in TTBS) of a rabbit anti-IαI antiserum that is HC specific, i.e., it does not detect bikunin, for 1 h at 37° C., followed by incubation with biotinylated goat anti-rabbit Ig (1:1000 in TTBS, 1 h at 37° C.). After incubation with a streptavidin-alkaline phosphatase conjugate (1:1000 in TTBS, 1 h at 37° C.) and with p-nitrophenyl phosphate (2 mg/ml in 50 mM Tris pH 9.5, 2 mM $MgCl_2$, 1 h at 37° C.), the amount of dephosphorylated substrate was determined by measuring the absorbance at 410 nm, using 800 nm as a reference wave length.

HC transfer to HA-sepharose. 100 µl of HA-sepharose (sediment) was incubated with 200 µl of 400 nM TSG-6 in TTBS for 2 h at 37° C. After extensive washing with TTBS (three times 400 µl) the HA-sepharose was incubated with a 1:100 dilution of human plasma in PBS (2 h at 37° C.). After extensive washing, as above, the HA-sepharose was treated with 100 µl of 10 u/ml *Streptomyces* hyaluronidase (in PBS, 2 h at 50° C.). 100 µl of 2×SDS-PAGE sample buffer was added to the HA-sepharose and, after vortexing, the liquid phase was recovered by centrifugation in a Spin-X column (Corning Inc., Corning, N.Y.). The recovered filtrate was analyzed by immunoblotting for the presence of TSG-6, HCs, TSG-6-HC complexes etc. using HC- and TSG-6-specific antibodies. Controls were treated either only with TSG-6, or only with plasma, or without TSG-6 and plasma. In order to discern between HC transfer by free TSG-6 vs. HA-TSG-6 complexes, the incubation with plasma was also carried out in TTBS instead of PBS, for reasons more fully described under the Results section below.

HC transfer by solid-phase HA-TSG-6 complexes to HA in solution. TSG-6 was bound to HA-sepharose as described above. 100 µl of HA-sepharose (sediment) was incubated with 200 µl of 100 nM TSG-6 in TTBS for 2 h at 37° C. After extensive washing with TTBS (three times 400 µl) the HA-sepharose was incubated with 100 µl of a 1:600 dilution of human plasma in PBS containing 100 µg/ml Select HATM of 30 kDa (2 h at 37° C.). 100 µl of 2×SDS-PAGE sample buffer was added to the HA-sepharose and, after vortexing, the liquid phase was recovered by centrifugation in a Spin-X tube (Costar). The recovered filtrate was analyzed by immunoblotting for the presence of HA-HC complexes using HC-specific antibodies and a HA-specific HABP probe. Controls were treated either only with TSG-6, or only with plasma, or without TSG-6 and plasma. In order to discern between HC transfer by free TSG-6 vs. HA-TSG-6 complexes, the incubation with plasma was also carried out in TTBS instead of PBS.

Formation of HA-HC complexes in solution. 20 nM TSG-6, 100 µg/ml Select HA, and human plasma diluted 1:600 were co-incubated for 2 h at 37° C. in PBS and the reaction products were analyzed by immunoblotting for the presence of TSG-6, Id', HCs, TSG-6-HC complexes, HA-HC complexes, and free bikunin using HC-, TSG-6-, or bikunin-specific antibodies or the HA-specific HABP probe. Controls contained either one or two of the three components (TSG-6, plasma, HA).

Results

TSG-6 Mediates Transfer of HCs from IαI to Immobilized HA

IαI has been reported to be physically associated with HA in synovial fluids of patients with rheumatoid arthritis, but not in synovial fluids of normal human subjects, and the formation of HA-HC complexes has been described after co-incubation of HA with normal bovine or human serum (Huang et al., 1993; Becker et al., 1971; Hamerman et al., 1966; and Sandson et al., 1965). On the other hand, TSG-6 forms stable complexes with HCs of IαI and can transfer them to HA (Mukhopadhyay et al., 2004; Rugg et al., 2005; and Jessen et al., 2004). It is currently not clear if TSG-6 is essential for HC transfer to HA to occur or if there are alternative pathways independent of TSG-6. In order to investigate this question, HA coupled covalently to the surface of Covalink-NH plates (Cov-HA) was used. Cov-HA was previously used to study the binding of TSG-6 to HA (Wisniewski et al., 2005).

The transfer of HCs to Cov-HA was analyzed after incubation of IαI in Cov-HA either in the absence or in the presence of recombinant TSG-6 in Cov-HA, followed by stringent washing, and detection by a rabbit anti-HC antibody that reacts with IαI and HCs, but does not detect bikunin. As shown in FIG. 1A, there was virtually no binding of purified human IαI, or its HCs, to immobilized HA in the absence of TSG-6. HC binding to HA was readily detectable if purified TSG-6 is added to purified IαI. The quantitative assay does not distinguish between bound HCs or complete IαI, and this issue is further addressed below.

Figure 1B:
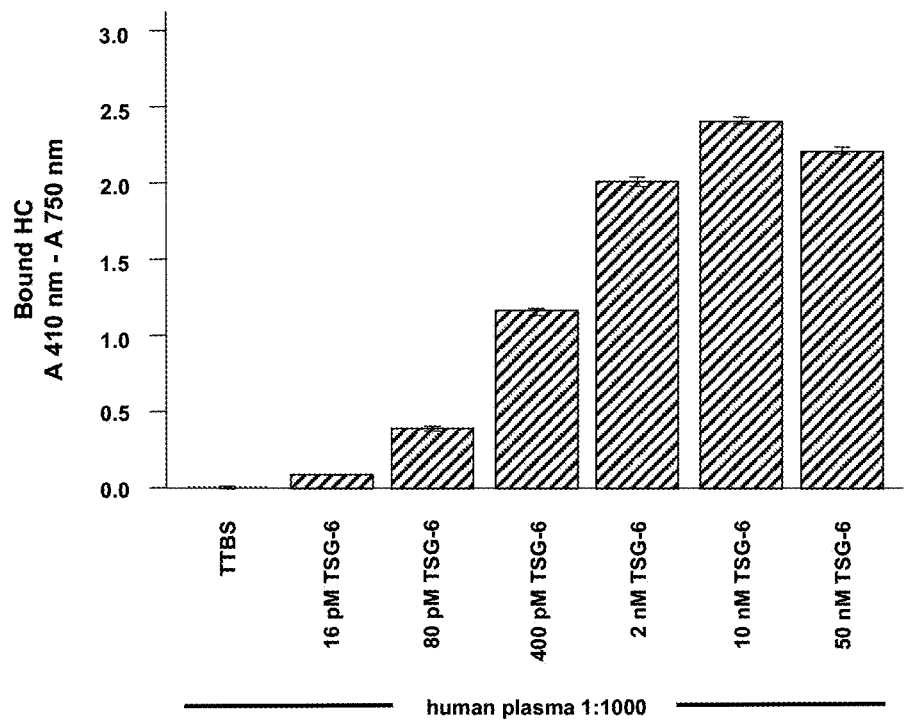
Figure 1C:
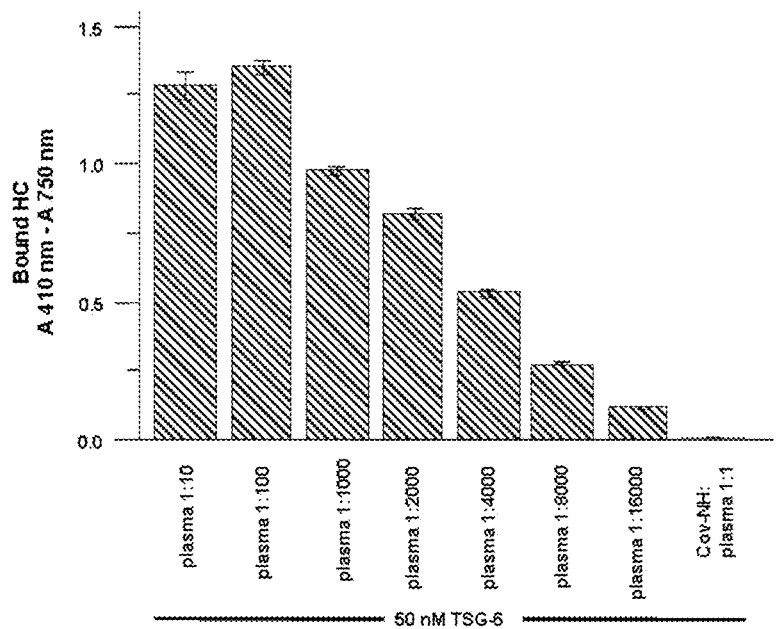
Figure 1D:
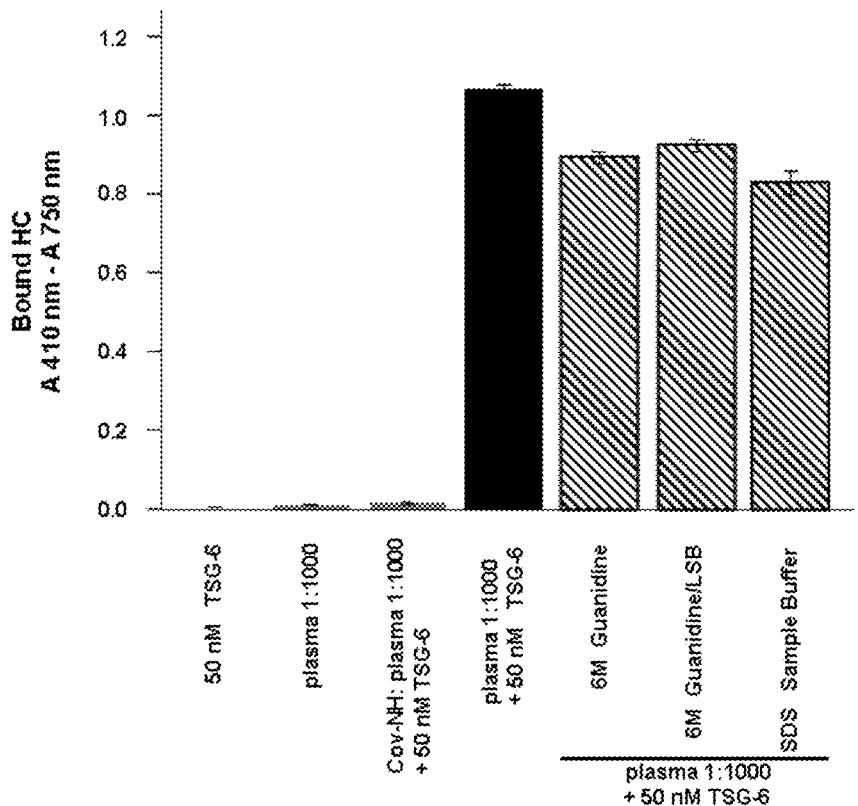
Figure 10:
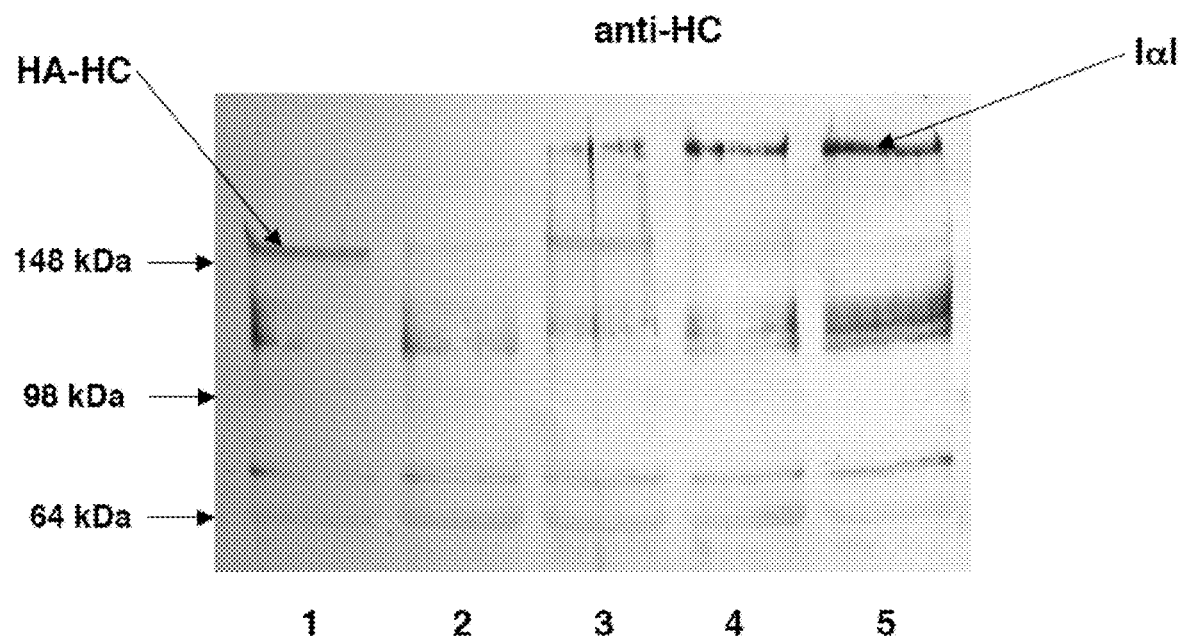
FIG. 10 is a gel showing HC transfer from IαI to HA in solution by pre-formed HA Sponge B-TSG-6 complexes. 30 nM TSG-6 in TTBS (20 mM Tris pH 7.5, 500 mM NaCl, 0.1% Tween-20) was incubated with 50 µl of HA Sponge B (gel sediment) in a total volume of 100 µl (adjusted with TTBS) at 37° C. for 2 h to form HA Sponge B-TSG-6 complexes (lanes 1, 2). Controls did not contain TSG-6 (lanes 3, 4). After extensive washing with TTBS, the supernatants were carefully and completely removed. Thereafter, 200 µl of 100 µg/ml of SelectHA™ 30 kDa in PBS containing 5 mM $MgCl_2$ and human plasma at a final dilution of 1:500 was added to the gel sediment and incubated 37° C. for 2 h to transfer HCs to the HA (lanes 1, 3). Alternatively, diluted plasma was added without HA as a control (lanes 2, 4). Thereafter, the supernatants were collected and analyzed by immunoblotting using an anti-HC antibody for the presence of HCs and HC-containing complexes. Note the consumption of IαI in the presence of TSG-6 (lanes 1, 2). The HC-specific antibody recognizes a weak band of similar size as HA-HC in the absence of either HA (lane 2), TSG-6 (lane 3), or both (lane 4), which could be bikunin-HC, a common degradation product of IαI. Lane 5 shows human plasma diluted 1:500.

In order to investigate whether the lack of HC transfer from purified IαI to Cov-HA is an artifact resulting from partial denaturation of this complex protein during its purification, the transfer of HCs from IαI in plasma to immobilized HA was examined. FIG. 1B shows that the transfer of HCs from IαI in diluted human plasma to Cov-HA is also completely dependent on the presence of added TSG-6 protein. As little as 16 µM TSG-6 is sufficient to mediate detectable transfer of HCs from IαI in human plasma to Cov-HA (FIG. 1B). The average concentration of IαI in human plasma is about 700 mg/l (Baek et al., 2003). The laboratory of the present inventors tested how the plasma concentration affects the binding of IαI to HA (FIG. 10). With respect to HC transfer to Cov-HA in the presence of TSG-6, the IαI concentration in human plasma is saturating, and a 1:100 dilution of human plasma did not result in any decrease of HC transfer. Even at a 1:4000 dilution of plasma the transfer of HCs to HA was only decreased by about 50%, and HC transfer was still detectable at a plasma dilution of 1:16000. This means that concentrations of unpurified IαI of as little as 200 pM are sufficient for detectable HC transfer to HA. Interestingly, some HC transfer to Cov-HA could be detected in the absence of exogenous TSG-6 at high plasma concentrations (FIG. 1D). However, a plasma dilution of 1:1000 completely abolished any detectable transfer, while TSG-6-dependent HC transfer at this plasma dilution was not affected (FIG. 1D), making it unlikely that the IαI concentration is the factor limiting the HC transfer in the absence of exogenous TSG-6.

Stability of the Bond Between HCs and Immobilized HA

Figure 2A:
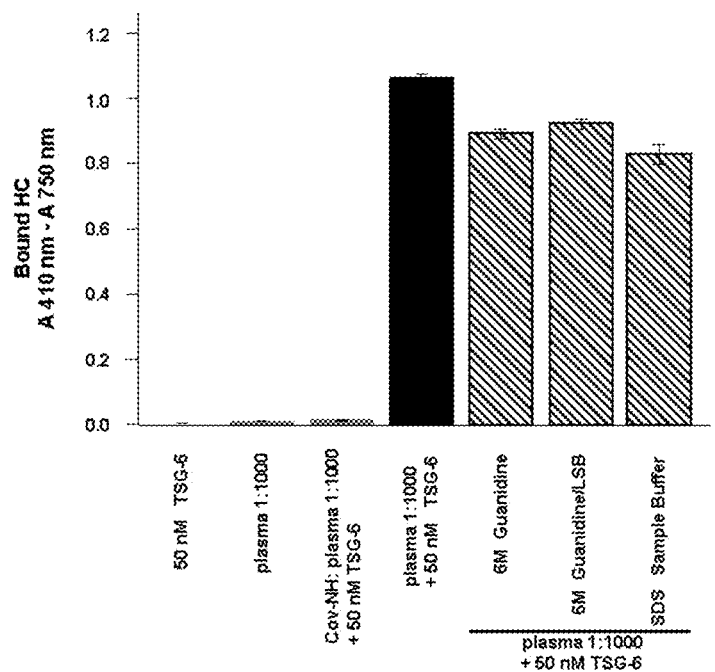
FIGS. 2A and 2B are graphs showing the stability of the bond between HCs and HA.
Figure 2B:
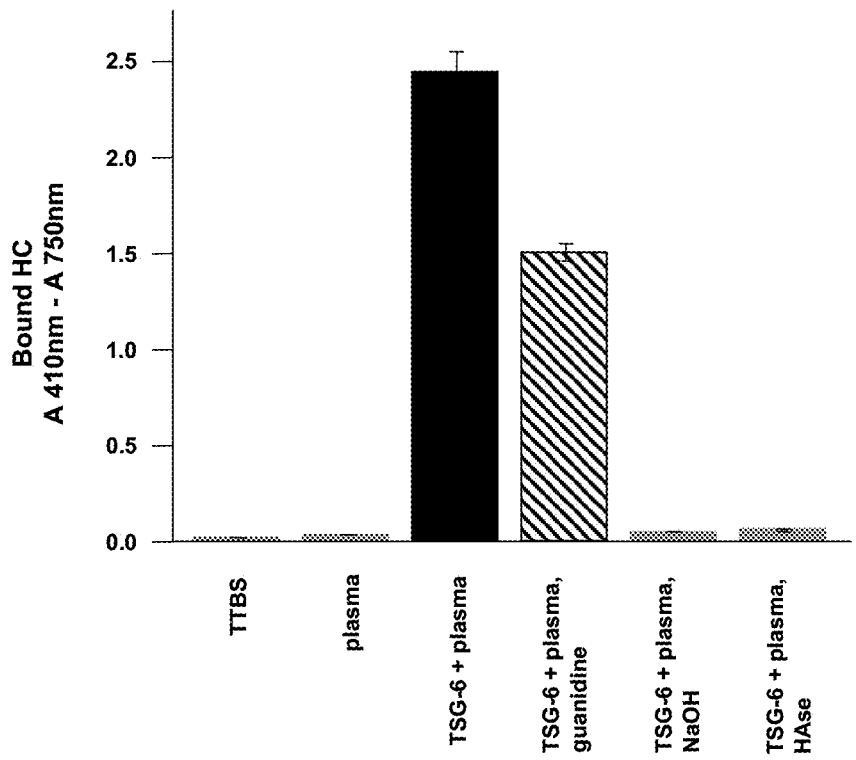

The present inventors reported earlier that TSG-6 forms a remarkably stable bond to immobilized HA in a strictly temperature-dependent fashion. Using the same assay system, IαI HCs found to be transferred to immobilized HA in the presence of 50 nM TSG-6 are also almost completely resistant to treatment with 6 M guanidine HCl, 6 M guanidine HCl containing 8% LSB, or SDS-PAGE sample buffer containing 2-mercaptoethanol (FIG. 2A). However, they were sensitive to treatment with hyaluronidase from *Streptomyces hyalurolyticus* and, in contrast to HA-TSG-6 complexes, they were also sensitive to treatment with diluted alkali, in agreement with the presence of an ester bond between HA and HC in HA-HC complexes (Zhao et al., 1995) (FIG. 2B). This provides evidence that the HC transfer observed on Cov-HA yields products indistinguishable from the ones observed with HA in solution.

Simultaneous vs. Sequential TSG-6 Binding and HC Transfer to Cov-HA

Figure 3A:
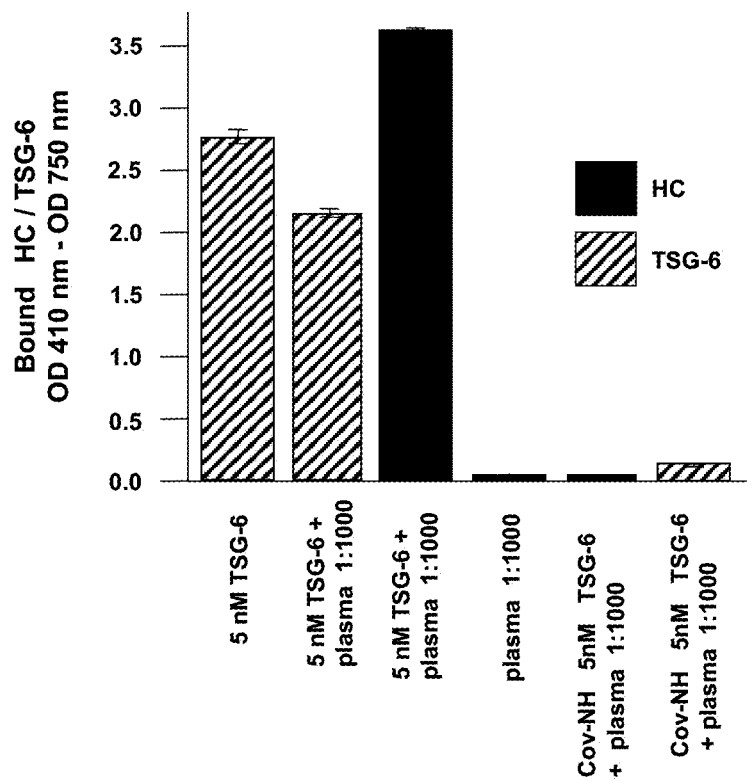
FIGS. 3A and 3B are graphs showing simultaneous and sequential binding of TSG-6 and HCs to HA.

Because TSG-6 itself binds to Cov-HA under the conditions used to evaluate HC transfer to Cov-HA, as shown previously (Wisniewski et al., 2005), the present inventors investigated if both TSG-6 binding and HC transfer to Cov- HA can occur simultaneously. After co-incubation of TSG-6 and diluted plasma in Cov-HA, providing conditions for simultaneous binding of TSG-6 and HC transfer, both TSG-6 and IαI HCs could be detected attached to the surface-bound HA (FIG. 3A).

Figure 3B:
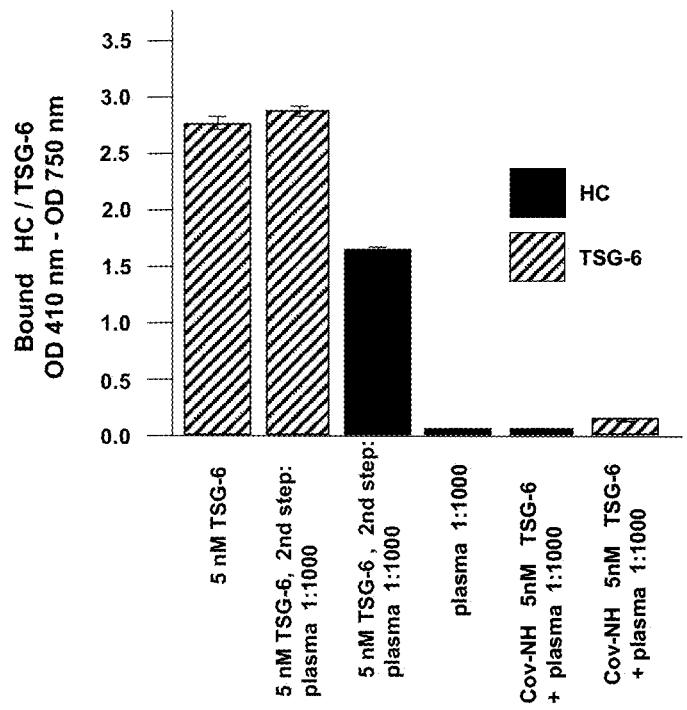

Because TSG-6 binding to Cov-HA resulted in the formation of stable complexes (Wisniewski et al., 1994), the present inventors also investigated if preformed HA-TSG-6 complexes are able to mediate the transfer of HCs from IαI to Cov-HA in a two-step reaction. FIG. 3B shows that TSG-6, after binding to Cov-HA under conditions that result in the formation of stable HA-TSG-6 complexes, is able to mediate the subsequent transfer of HCs to the Cov-HA substrate after all soluble TSG-6 has been removed by extensive washing. This Cov-HA binding assay cannot distinguish between HCs bound directly to HA, i.e., HA-HC complexes, and HCs bound to TSG-6, i.e., HA-TSG-6-HC complexes. This question will be addressed separately using a different experimental approach (see below).

Transfer of IαI HCs to Immobilized HA is Strictly Dependent on Metal Ions

Figure 4A:
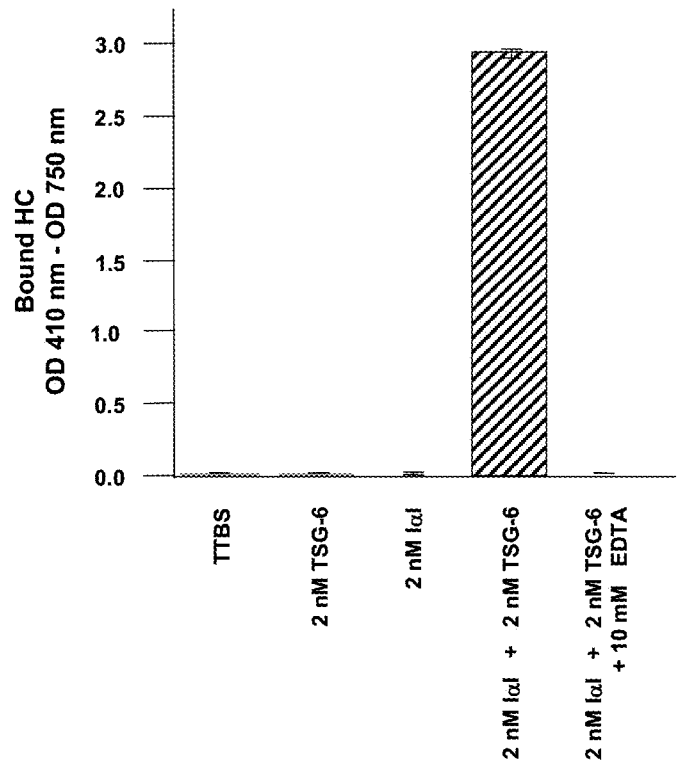
FIGS. 4A and 4B are graphs showing the effect of EDTA on the HC transfer.
Figure 4B:
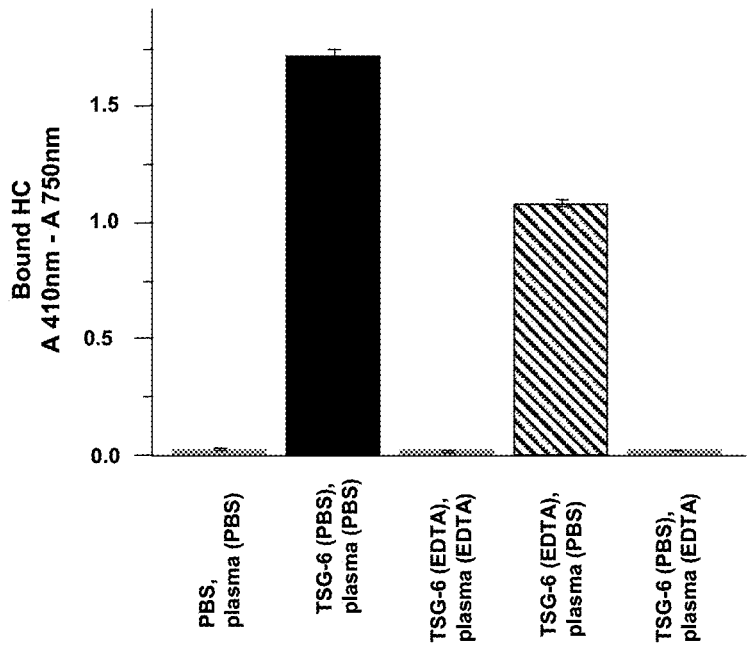

It was established earlier that the transfer of HCs to HA is dependent on the presence of divalent metal ions and could be prevented by the addition of EDTA (Rugg et al., 2005; Jessen et al., 2004; and Odum et al., 2002). FIG. 4A confirms that the TSG-6 dependent transfer of HCs to Cov-HA is completely prevented by the presence of 10 mM EDTA, a treatment that does not prevent the binding of TSG-6 to immobilized HA (Wisniewski et al., 2005). The role of metal ions on the individual steps of the 2-step reaction described above, i.e., the transfer of HCs to Cov-HA by pre-formed Cov-HA-TSG-6 complexes, was also determined. While the presence of EDTA during the binding of TSG-6 to Cov-HA has a modest effect on the transfer of HCs in the following step, the presence of EDTA during the second step, the interaction of pre-formed HA-TSG-6 complexes with IαI, completely prevented any HC transfer (FIG. 4B). The partial inhibitory effect of EDTA during the binding of TSG-6 to Cov-HA on the subsequent transfer of HCs is in good agreement with a similar effect of EDTA on the binding of TSG-6 to Cov-HA itself (Wisniewski et al., 2005).

Figure 5A:
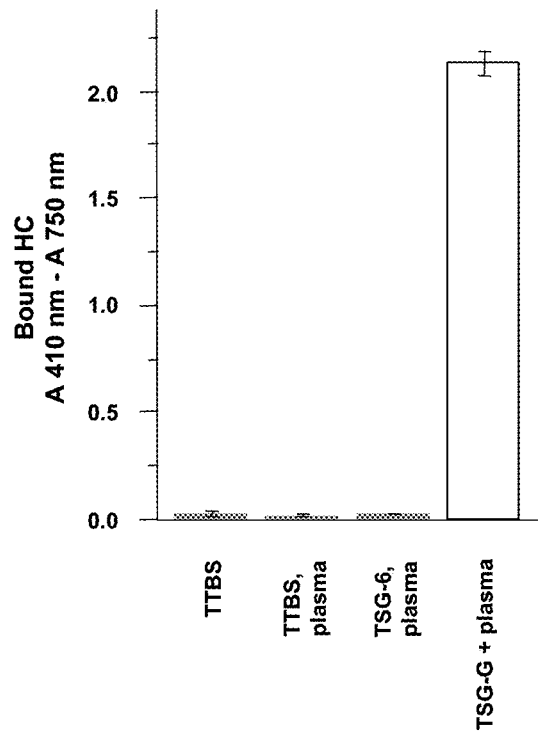
FIGS. 5A and 5B are graphs showing the effect of the ionic strength on the HC transfer to Cov-HA.
Figure 5B:
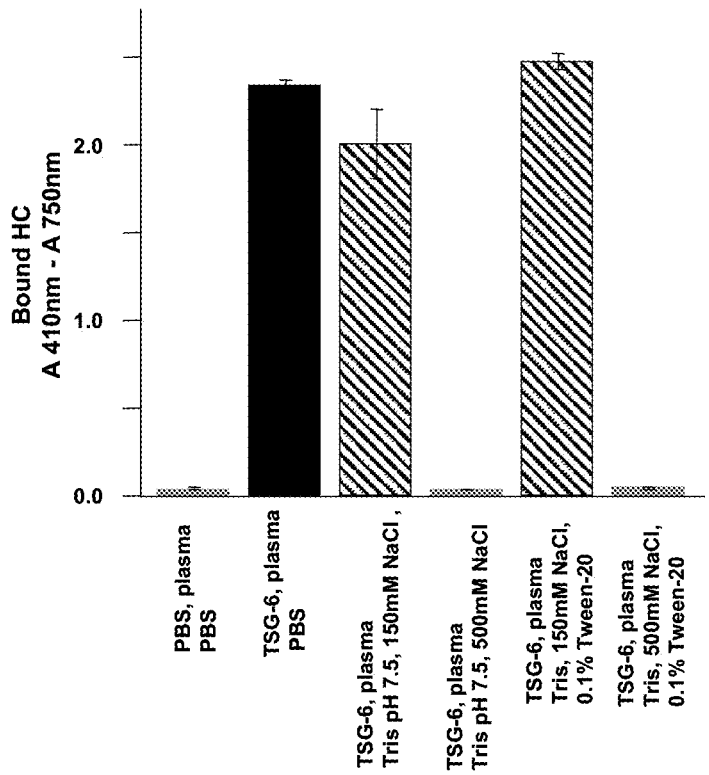

Differential Ionic Strength Requirements for the Transfer of HCs by Free TSG-6 or Pre-Formed HA-TSG-6 Complexes While the binding of TSG-6 to Cov-HA and the simultaneous transfer of HCs can be carried out in TTBS, i.e., in the presence of Tris buffer, 500 mM NaCl and 0.1% TWEEN-20, (FIGS. 1A-D, 5A), the sequential transfer of HCs by preformed HA-TSG-6 complexes required PBS and was completely suppressed in TTBS (FIG. 5A). In order to determine if the failure of sequential HC transfer was the result of the difference in ionic strength or the result of the presence of the non-ionic detergent, TWEEN-20, in TTBS, or the different ions in the two buffer systems, the second step of the sequential HC transfer, i.e., the transfer of HCs by preformed HA-TSG-6 complexes, was carried out in either PBS, Tris buffer pH 7.5 containing 150 mM NaCl, Tris buffer pH 7.5 containing 500 mM NaCl, Tris buffer pH 7.5 containing 150 mM NaCl and 0.1% TWEEN-20, or Tris buffer pH 7.5 containing 500 mM NaCl and 0.1% TWEEN-20 (TTBS). As can be seen in FIG. 5B, the second step of the sequential HC transfer is completely inhibited in the presence of 500 mM NaCl, but not by the presence of TWEEN-20, or by the different buffers used. This differential ionic strength requirement for the simultaneous and the two-step, or sequential transfer of HCs can therefore be used to differentiate between the two binding mechanisms, i.e., two-step transfer of HCs by HA-TSG-6 complexes is completely inhibited in 500 mM NaCl.

HC Transfer by Pre-Formed HA-TSG-6 Complexes Bound to Sepharose Results in HA-HC Complexes Pre-formed HA-TSG-6 complexes interact with IαI, resulting in the transfer of HCs to the HA substrate. Presumably, the first step of this transfer is the formation of a HA-TSG-6-HC complex, in analogy to the formation of TSG-6-HC complexes in the absence of HA. These HA-TSG-6-HC complexes may transfer HC in an additional step to HA, resulting in HA-HC complexes as final products, in analogy to HA-HC complexes formed with HA free in solution. Alternatively, HA-TSG-6-HC complexes could be the final product. These alternatives raise an important question because they would result in structurally different modifications of surface-bound HA vs. HA free in solution.

Figure 6:
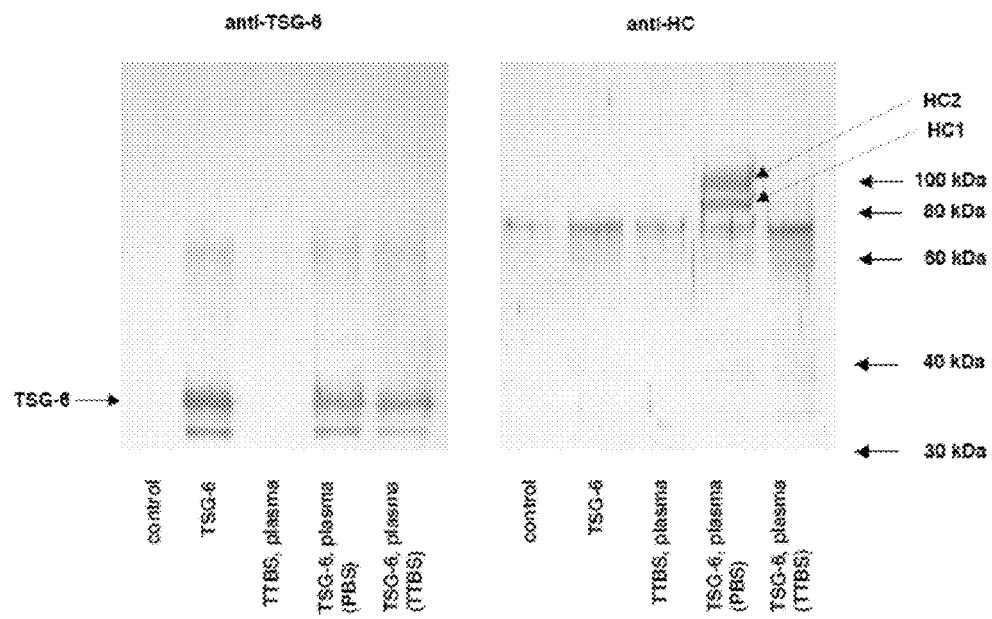
FIG. 6 is a gel showing the transfer of HCs by HA-TSG-6 complexes. 100 nM TSG-6 was incubated with 100 µl HA-Sepharose for 2 h at 37° C. After washing with TTBS, the HA-Sepharose was incubated with human plasma diluted 1:600 in either PBS or TTBS. Controls were incubated either with TTBS, TSG-6, or plasma only. All samples were treated with 10 u/ml HAse from *Streptococcus hyalurolyticus*. Released material was analyzed by immunoblotting using either rabbit anti-TSG-6 or rabbit anti-HC, as indicated.

In order to determine whether HC transfer by preformed HA-TSG-6 complexes results in a final HA-HC complex, or alternatively in a HA-TSG-6-HC complex, TSG-6 bound to HA-sepharose under conditions resulting in the formation of stable HA-TSG-6 complexes were employed (Wisniewski et al., 2005). After stringent washing to remove all free TSG-6 protein, the HA-TSG-6 complexes were incubated with plasma, as a source of IαI, washed again, and then treated with hyaluronidase from S. hyalurolyticus to release HA fragments and attached proteins from the sepharose. The recovered products were then analyzed by immunoblotting for the presence of either free HCs or TSG-6-HC complexes. In order to exclude the possibility that the HC transfer is due to the presence of residual free TSG-6, instead of HA-TSG-6 complexes, the incubation with diluted plasma was carried out either in TTBS or in PBS, as described above. FIG. 6 demonstrates that hyaluronidase treatment releases TSG-6 (left panel) and HCs (right panel), whereas no TSG-6-HC complexes could be detected. When the reaction between pre-formed HA-TSG-6 and plasma was carried out in TTBS, no HCs were transferred to the HA-sepharose (right panel), and the hyaluronidase treatment releases only the bound TSG-6 (left panel). This suggests that preformed HA-TSG-6 complexes were responsible for the observed transfer reaction, and that all of the HCs "captured" from IαI were directly transferred to HA. The diffuse nature of the HC bands in FIG. 6 (right panel) may be a consequence of residual HA fragments remaining attached to the HCs after hyaluronidase digestion. The finding that no TSG-6-HC complexes were released by the hyaluronidase treatment strongly suggests that HA-TSG-6-HC complexes are not a final product of this reaction.

HC Transfer by Surface-Bound HA-TSG-6 Complexes to HA Chain in Solution

Figure 7:
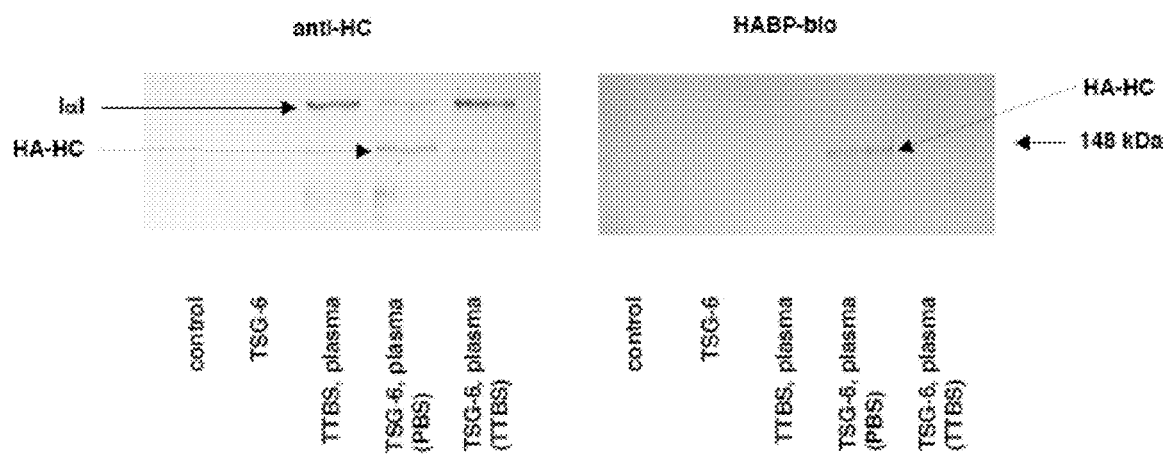
FIG. 7 is a gel showing the transfer of HCs by HA-TSG-6 complexes to a different HA strand. 100 nM TSG-6 was incubated with 100 µl HA-Sepharose for 2 h at 37° C. After washing with TTBS, the HA-Sepharose was incubated with human plasma diluted 1:600 and 100 µg/ml Select HA (molecular weight 30 kDa) in either PBS or TTBS for 2 h at 37° C. Controls were incubated either with TTBS, TSG-6 without plasma, or plasma without TSG-6 with Select HA. Supernatants containing Select HA but not the immobilized HA were analyzed by immunoblotting using either rabbit anti-HC or HABP-bio.

The experimental protocol to determine whether preformed sepharose-HA-TSG-6 complexes are able to transfer HCs from IαI to HA molecules in solution, i.e., to a different HA chain than the one binding TSG-6 on the solid surface, was modified. TSG-6 was incubated with HA-Sepharose in the first step of this protocol, as described above, to form stable sepharose-HA-TSG-6 complexes. In the second step, the HA-TSG-6 complexes were incubated with diluted plasma plus HA in solution (Select HA, 30 kDa), an HA preparation with a narrow molecular mass distribution. After the incubation, the liquid phase of the reaction mixture was analyzed by immunoblotting for the presence of HA-HC complexes. In order to exclude the possibility that the HC transfer is due to the presence of free TSG-6, instead of HA-TSG-6 complexes, the incubation with diluted plasma and Select HA was carried out either in TTBS or in PBS, as described above (FIGS. 5A and 5B). FIG. 7 shows that HA-HC complexes with Select HA are indeed formed in PBS, but not in TTBS, demonstrating that the Sepharose-HA-TSG-6 complex is able to transfer HCs to HA molecules in solution, and suggesting that HA-TSG-6 complexes are responsible for the HC transfer. These data indicate that TSG-6 bound to the immobilized HA is able to transfer HCs to a different HA chain free in solution.

TSG-6-Mediated HC Transfer can Deplete IαI and Generate Free Bikunin

Figure 8A:
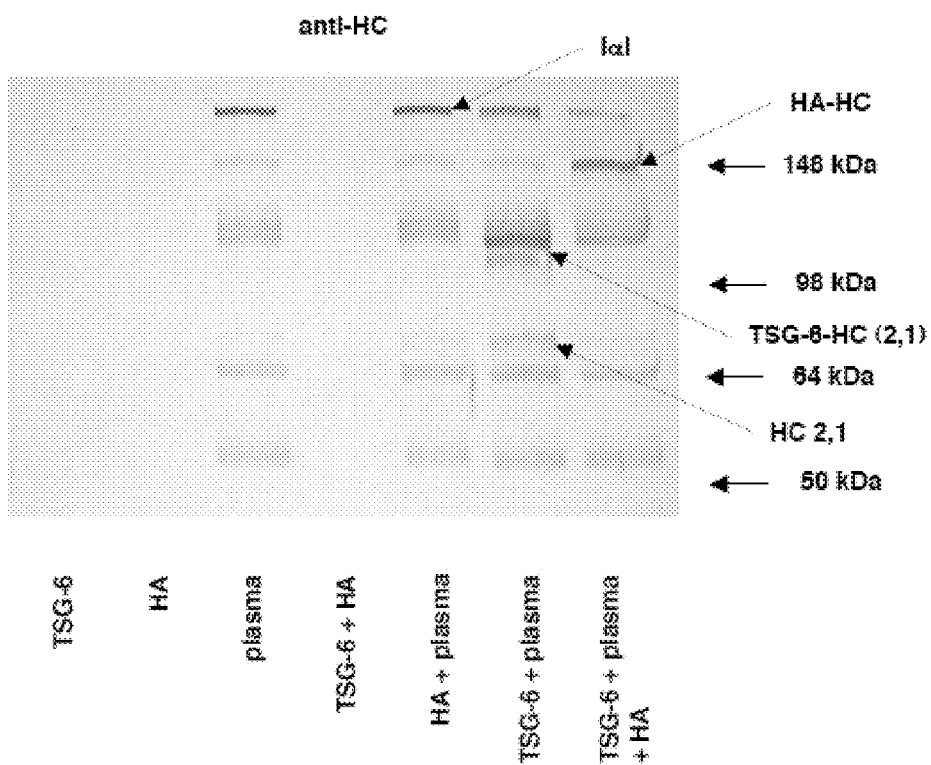
FIGS. 8A-8D are gels showing that HC transfer in solution results in formation of HA-HC complexes, depletion of IαI and TSG-6-HC complexes, and generation of free bikunin. 20 nM TSG-6, human plasma diluted 1:600, and 100 µg/ml Select HA (30 kDa) were co-incubate for 2 h at 37° C. Controls for TSG-6 alone, plasma only, HA alone, TSG-6 plus plasma, TSG-6 and HA, and plasma and HA were also included. The reaction products were analyzed by immunoblotting using anti-HC (FIG. 8A), HABP-bio (FIG. 8B), anti-TSG-6 (FIG. 8C) or anti-bikunin (FIG. 8D).
Figure 8B:
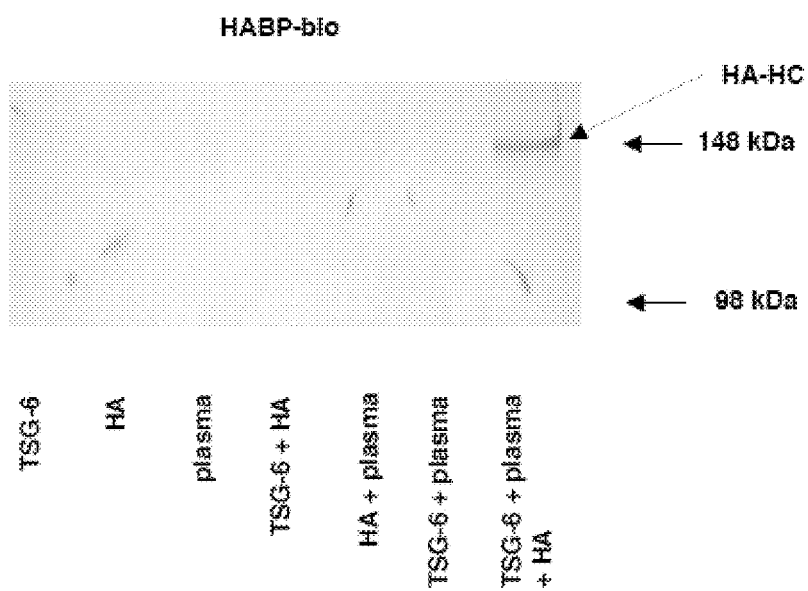
Figure 8C:
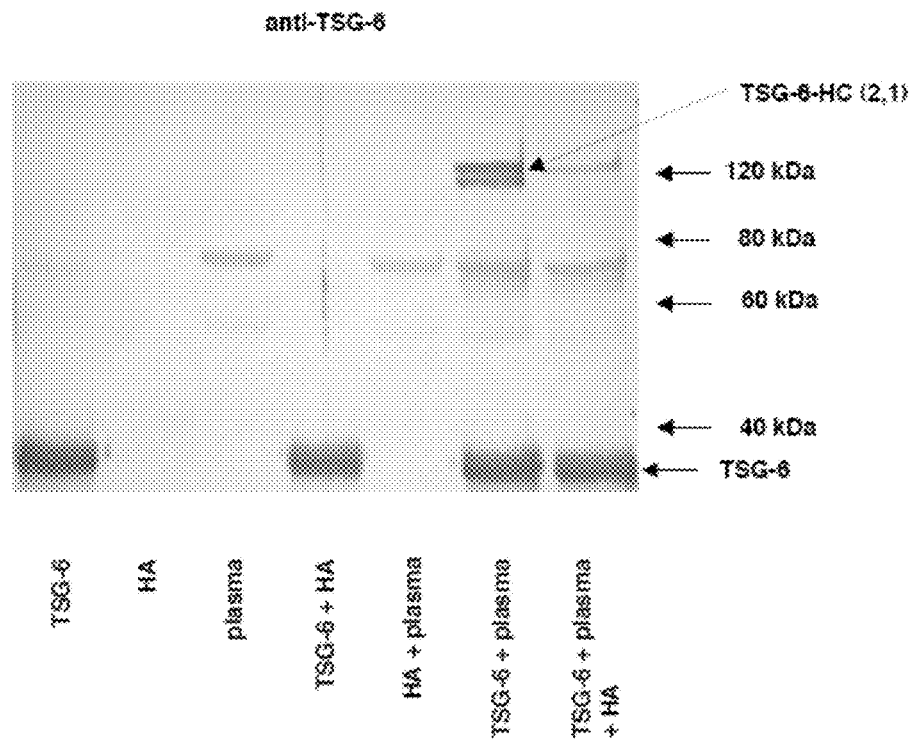

All the previous experiments were carried out using surface-bound HA as at least one of the reactants. When TSG-6 and plasma, as a source of IαI, are co-incubated in the absence of HA, TSG-6-HC complexes are a major species detected (FIGS. 8A and 8C). However, when Select HA is included in the reaction mixture, HA-HC complexes are the major species detected (FIGS. 8A and 8B). HA-HC complexes are detected both by an anti-HC antibody (FIG. 8A) and by the HA-detecting HABP-bio probe (FIG. 8B). The lack of detection of free HA by this probe is due to the failure of free HA to blot to the PVDF membrane—it can be detected by an HABP-bio affinity probe after transfer to positively charged blotting membranes (data not shown).

Figure 8D:
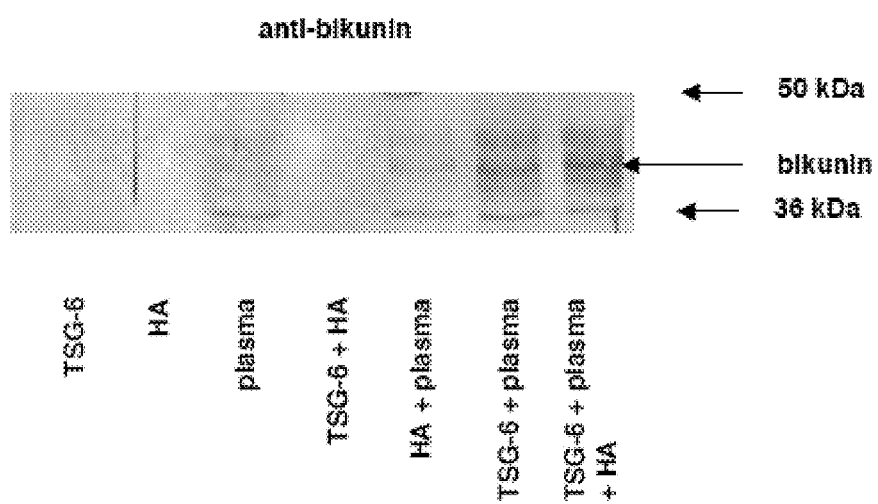

Notably, the presence of both TSG-6 and Select HA in the reaction mixture, resulted in significant depletion of the available IαI (FIG. 8A) and the generation of free bikunin (FIG. 8D). When only TSG-6 was added to plasma, less bikunin was generated and more IαI remained, suggesting that the presence of HA as acceptor for HC transfer contributes to IαI depletion and the generation of free bikunin.

Interestingly, while the interaction of TSG-6 with immobilized HA resulted in the formation of stable HA-TSG-6 complexes (Wisniewski et al., 2005), there is no indication that the interaction of TSG-6 with HA in solution resulted in the generation of stable HA-TSG-6 complexes (FIG. 5C). Because the transfer of HCs to HA in solution was strictly TSG-6-dependent, the interaction of TSG-6 or TSG-6-HC complexes with HA has to be considered a prerequisite to the transfer of HCs to HA. However, this interaction did not, in contrast to the interaction of TSG-6 with surface-bound HA, result in stable binding of TSG-6 to HA.

Discussion

Components of the plasma proteinase inhibitor IαI have been known for many years to associate tightly with HA in the synovial fluid of patients with rheumatoid arthritis. However, while the complex structure of IαI remained unresolved for over two decades, the composition of the complexes, and in particular the presence of the bikunin chain, was not addressed in those early studies (Becker et al., 1971; and Sandson et al., 1965). Later, it became clear that HA in synovial fluid of rheumatoid arthritis patients was associated with HCs only, and not with complete IαI (Huang et al., 1993). Interestingly, HA-HC complexes could be generated by co-incubation of HA with either normal human or bovine serum, leading to the suggestion that the HCs of IαI bind to HA spontaneously (Huang et al., 1993). However, the few reports that addressed the interaction between purified IαI, or its HCs, and HA experimentally, did not provide evidence for the formation of stable HA-HC complexes under physiological conditions, and the only direct interaction between HCs and HA was limited to conditions of low ionic strength, and the stability of the resulting complexes was not investigated (Chen et al., 1994; and Jean et al., 2001). In contrast, the catalytic role of TSG-6 for the transfer of HCs to HA and to HA oligosaccharides and the formation of stable HA-HC complexes in solution has been convincingly demonstrated (Mukhopadhyay et al., 2004; Rugg et al., 2005; and Jessen et al., 2004).

The data presented in this Example show that no HC transfer to HA occurs with purified IαI, or with highly diluted plasma, in the absence of TSG-6, but that added TSG-6 in picomolar concentrations catalyzes HC transfer (FIGS. 1A and 1B). HC transfer in the presence of TSG-6 is detectable with plasma diluted as much as 1:16,000, equivalent to an IαI concentration of about 200 pM. In agreement with published data (Huang et al., 1993), it was found that some HC transfer to HA can take place in plasma in the absence of added TSG-6, although the amount of transferred HCs is small compared to TSG-6-mediated transfer. The present inventors cannot rule out that this modest HC transfer is the result of trace amounts of TSG-6 in normal plasma that are below the detection limit of currently available antibody-based assays. Significant generation of HA-HC complexes in vivo has been associated with rheumatoid arthritis (Becker et al., 1971; Sandson et al., 1965; and Kida et al., 1999). It is therefore significant that TSG-6 was found in synovial fluid of patients with rheumatoid arthritis, osteoarthritis, Sjögren's syndrome, polyarthritic gout, and osteomyelitis (Wisniewski et al., 1993). In addition, immunoblots of these synovial fluids revealed stable complexes of TSG-6 with HCs of IαI (Wisniewski et al., 1994; and Wisniewski et al., 1993). The presence of TSG-6 and of TSG-6-HC intermediates in synovial fluids of patients with various inflammatory joint conditions strongly supports a significant role for TSG-6 in the generation of HA-HC complexes.

The present inventors show in this Example that preformed surface-bound HA-TSG-6 complexes are, like TSG-6 in solution, able to interact with IαI and transfer HCs to HA (FIG. 3B). This alternative pathway of HA-HC complex formation may become significant in instances when the local expression of TSG-6 precedes the influx of IαI from the vascular compartment. The present inventors could also demonstrate that the final product of this alternative reaction is the same as after HC transfer by free TSG-6, i.e., a HC directly cross-linked to HA (FIG. 6). This is consistent with the structure of the HA-HC complexes identified in synovial fluid of patients with rheumatoid arthritis (Zhao et al., 1995).

While HC transfer mediated by TSG-6 in solution readily proceeds in the presence of 500 mM NaCl, HC transfer by HA-TSG-6 complexes bound to a solid phase is completely suppressed (FIG. 5). Although this effect of high ionic strength may not have a physiological parallel, it provides a convenient experimental tool to differentiate between the single phase and the two phase reaction and suggests differences in the mechanism of the HC transfer.

HA-HC complexes formed on the solid substrate were resistant to treatment with dissociating and reducing agents, but sensitive to treatment with mild alkali or HAse (FIGS. 2A and 2B). The alkali sensitivity is consistent with the presence of an ester bond linking HC and HA, in analogy to the bonds that have been determined in HA-HC complexes from rheumatoid synovial fluid, and the ester bonds linking chondroitin sulfate and HCs in IαI (Enghild et al., 1991; and Zhao et al., 1995). The sensitivity of HA-HC complexes to alkali treatment is in marked contrast to HA-TSG-6 complexes formed on the Covalink substrate, that are alkali resistant (Wisniewski et al., 2005).

The question of whether HA-TSG-6 complexes can transfer HCs to a different HA chain was also addressed. The data shown in FIG. 7 show that TSG-6, bound to immobilized HA, was able to transfer HCs to HA in solution. This is mechanistically interesting because it suggests the interaction of a putative intermediary HA-TSG-6-HC complex with a second HA chain.

With respect to the fate of the HCs, transfer by TSG-6 to HA in solution is very similar to transfer to solid-phase HA, e.g., TSG-6-HC complexes are formed as intermediates but, in the presence of sufficient HA, are almost completely depleted in the final transfer of HCs to HA (FIGS. 8A and 8C). However, a notable difference between HC transfer to HA in solution and to surface-bound HA is that there is no evidence for the formation of stable HA-TSG-6 complexes with HA in solution (FIGS. 8B and 8C).

The present inventors have shown earlier that the formation of stable complexes between TSG-6 and surface-bound HA is the result of a two-step reaction with different temperature requirements. At 4° C., TSG-6 binds to Cov-HA but can be easily dissociated, whereas the Cov-HA-TSG-6 complex formed at 37° C. is resistant to dissociative and reducing conditions (Wisniewski et al., 2005). Although this phenomenon is outside the scope of this study, the data suggest that TSG-6 is able to differentiate between HA in solution and surface-bound HA and forms stable complexes only with surface-bound HA. The mobility of HA in tissues varies widely, from free HA in solution in synovial fluid and HA bound to cellular surfaces via HA receptors, forming a pericellular matrix, to HA complexed with proteoglycans and tightly packed into a collagen network in cartilage. Nevertheless, it is currently not clear what the physiological equivalent of surface-bound HA is.

The transfer of HCs from IαI to HA by TSG-6 results in the formation of free bikunin (FIG. 8D). In the presence of TSG-6 and sufficient HA, IαI can be almost completely depleted, and HA-HC complexes and free bikunin are the final products (FIGS. 8A, 8B and 8D). A decrease of IαI in plasma or serum has been observed in association with infectious disease and sepsis and the concentration of IαI in the serum of sepsis patients has been correlated with the outcome of the disease (Baek et al., 2003; Balduyck et al., 2000; Lim et al., 2003; and Opal et al., 2007). In addition, administration of exogenous IαI reduced mortality and maintained hemodynamic stability in experimental models of sepsis (Wu et al., 2004; and Yang et al., 2002). The decrease of IαI concentrations in blood associated with disease is usually considered to be the result of proteolytic degradation by neutrophil elastase or similar enzymes (Balduyck et al., 1993 and 2000; and ZHirose et al., 1998). Data from the present inventors suggest that TSG-6 and HA can also efficiently "degrade" IαI, simultaneously generating HA-HC complexes and free bikunin. The present inventors have reported earlier the presence of TSG-6 in sera of sepsis patients and in sera of volunteers treated with TNF-α suggesting that involvement of TSG-6 in the degradation of IαI is feasible (Wisniewski et al., 1997).

The pathophysiological role of IαI "degradation", in contrast to low IαI levels, is not necessarily a detrimental one. While IαI degradation is associated with bikunin generation, low IαI levels entail depletion of a bikunin precursor. Bikunin, or urinary trypsin inhibitor, has been associated with many beneficial activities, prominently among them anti-inflammatory effects (Pugia et al., 2005). While the serine protease inhibitory activity of bikunin may account for many of these effects, some effects of bikunin may be mediated by a bikunin-specific cellular receptor, which may not interact with the bikunin of IαI due to steric interference from its covalently attached HCs (Pugia et al., 2005). The ability of IαI to improve hemodynamic stability in an experimental model of sepsis is similar to effects attributed to bikunin (Molor-Erdene et al., 2005). Therefore, free bikunin may be the active agent responsible for some of the effects attributed to IαI.

While the modifications of HA and the turnover of IαI caused by the presence of TSG-6 protein are becoming increasingly clear, the physiological activities of the newly generated HA-HC complexes and potential differences between the activities of IαI and bikunin are still not well understood. The elucidation of these activities will finally contribute to the understanding of the mechanism of action of TSG-6, which has been consistently associated with anti-inflammatory and chondroprotective effects in experimental models of acute inflammation and arthritis.

Example 2

Binding of Recombinant TSG-6 to Radiation Crosslinked Hyaluronan and Capacity of the Complex to Transfer Heavy Chains from Inter-α-Inhibitor to Hyaluronan in Solution The goal of this study was to demonstrate that, in addition to hyaluronan (HA) associated with a solid surface, as shown in Example 1, crosslinked HA in the form of a hydrated gel is also able to form stable complexes with TSG-6 protein and that these HA-TSG-6 complexes are able to subsequently interact with the plasma protein inter-α-inhibitor (IαI) and to transfer heavy chains (HC) from IαI to water-soluble HA that is in contact with the crosslinked HA gel. In order to demonstrate this ability of TSG-6 to stably modify a cross-linked HA-based gel, a crosslinked HA gel prepared according to U.S. Pat. No. 6,610,810, hereafter referred to as "HA Sponge B", was used.

Materials and Methods

Reagents. Hyaluronidase from *Streptomyces hyalurolyticus* and biotinylated hyaluronan binding protein (HABP-bio) were purchased from Associates of Cape Cod. SelectHA™ 30 kDa was purchased from Hyalose L.L.C. Human plasma was obtained from the blood bank of the NYU Medical Center. Rabbit anti-human IαI was from Dako. Although this antibody was raised against IαI, it did not detect bikunin in immunoblotting and ELISA and is therefore referred to as HC-specific. The rabbit anti-TSG-6 antibody was raised against native recombinant TSG-6 and has been described (Mindrescu et al., 2005). Biotinylated goat anti-rabbit Ig was from Dako and streptavidin-alkaline phosphatase conjugate was from Invitrogen. The alkaline phosphatase substrate was BCIP/NBT from Bio-Rad for immunoblots. PDVF membrane for immunoblotting was from Millipore (Immobilon P). HA Sponge B gel was obtained from the Matrix Biology Institute (Edgewater, N.J.) as a hydrated gel suspended in $dH_2O$.

TSG-6 protein. TSG-6 protein was expressed in BTI-TN-5B1-4 insect cells after infection with recombinant nuclear polyhedrosis virus (baculovirus) and purified as described (Wisniewski et al., 1994 and 2005).

Binding of TSG-6 to HA Sponge B gel. HA Sponge B gel was stored as a hydrated gel suspended in $dH_2O$. Before a binding experiment, the gel was washed extensively and equilibrated with the buffer to be used in the experiment, either TTBS (20 mM Tris pH 7.5, 500 mM NaCl, 0.1% Tween-20) or PBS containing 5 mM $MgCl_2$. The gel was then incubated with a defined concentration of recombinant TSG-6 at 37° C. for 2 h under constant rotation to facilitate contact of TSG-6 with the gel particles. Finally, the gel was washed extensively with TTBS to remove any free TSG-6.

Transfer of HCs by HA gel-TSG-6 complexes. The washed HA Sponge B gel containing complexes with TSG-6 was incubated with diluted human plasma as a source of IαI at a final dilution of 1:500 (i.e., ca. 6 nM IαI) in the presence of SelectHA™ 30 kDa, the latter to evaluate whether the TSG-6-HA Sponge B complex was able to transfer HCs from IαI to the SelectHA™ 30 kDa in the aqueous phase. The incubation was carried out in PBS containing 5 mM $MgCl_2$. The supernatant containing the SelectHA™ 30 kDa was then collected and analyzed by immunoblotting for the presence of HA-HC complexes. Immunoblotting was carried out using 12% polyacrylamide gels and denaturing conditions (2% SDS, 5% 2-mercapthethanol), and PVDF as blotting membrane.

Results

Figure 9:
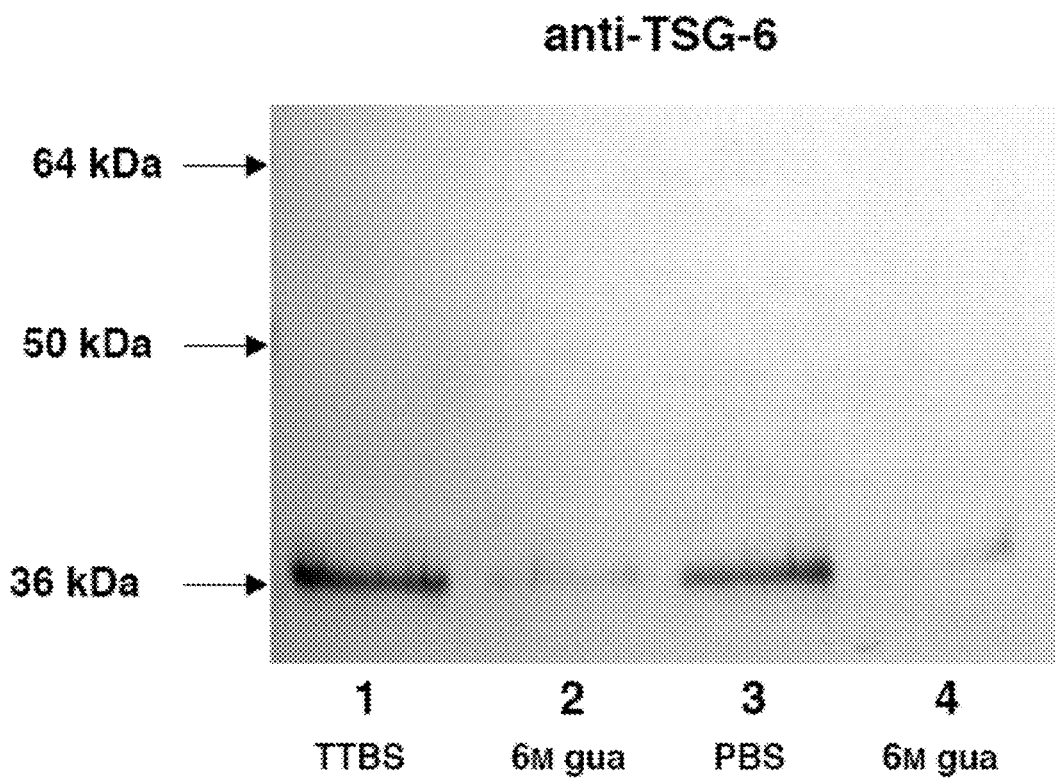
FIG. 9 is a gel showing the formation of a stable (guanidine-resistant) bond between TSG-6 and HA Sponge B gel. 30 nM of TSG-6 in either TTBS (20 mM Tris pH 7.5, 500 mM NaCl, 0.1% Tween-20) (lanes 1, 2) or PBS containing 5 mM $MgCl_2$ (lanes 3, 4), were incubated with 50 µl of HA Sponge B gel in a total volume of 200 µl at 37° C. for 2 h to form HA Sponge B-TSG-6 complexes. Two of the gels (lanes 2, 4) were then treated with 6 M guanidine HCl containing 8% lauryl sulfobetain for 15 min at ambient temperature. This treatment is known to dissociate most proteins not bound covalently to hyaluronan. After extensive washing with TTBS and centrifugation in a Spin-X tube to remove all supernatant, the gel was re-suspended in the Spin-X tube in 50 µl of 10 u/ml of *Streptomyces* hyaluronan lyase in PBS and incubated for 2 h at 37° C. After centrifugation at 20,000 g for 3 min, the filtrate was collected for analysis by immunoblotting using a rabbit anti-TSG-6 antibody.

Formation of stable HA-TSG-6 complexes. After incubation of recombinant TSG-6 with the HA Sponge B gel for 2 h at 37° C. in either TTBS or in PBS containing 5 mM $MgCl_2$, the gel was washed extensively in TTBS, to remove all TSG-6 that was not tightly bound, and either left in TTBS or treated with the denaturing agent 6M guanidine HCl containing 8% of lauryl sulfobetain (LSB). After degradation of the gels using *Streptomyces* hyaluronan lyase, the degraded gel was analyzed by immunoblotting for the presence of TSG-6. FIG. 9 shows that TSG-6 protein was found associated with HA Sponge B gel after incubation and washing in either TTBS (lane 1) or PBS containing 5 mM $MgCl_2$ (lane 3). Although treatment with 6M guanidine HCl containing 8% LSB resulted in a decrease of the amount of TSG-6 associated with the HA gel, TSG-6 forming a guanidine-resistant, i.e., stable, bond could be detected after incubation of TSG-6 with HA Sponge B gel in either TTBS (lane 2) or PBS containing 5 mM $MgCl_2$ (lane 4).

Figure 11:
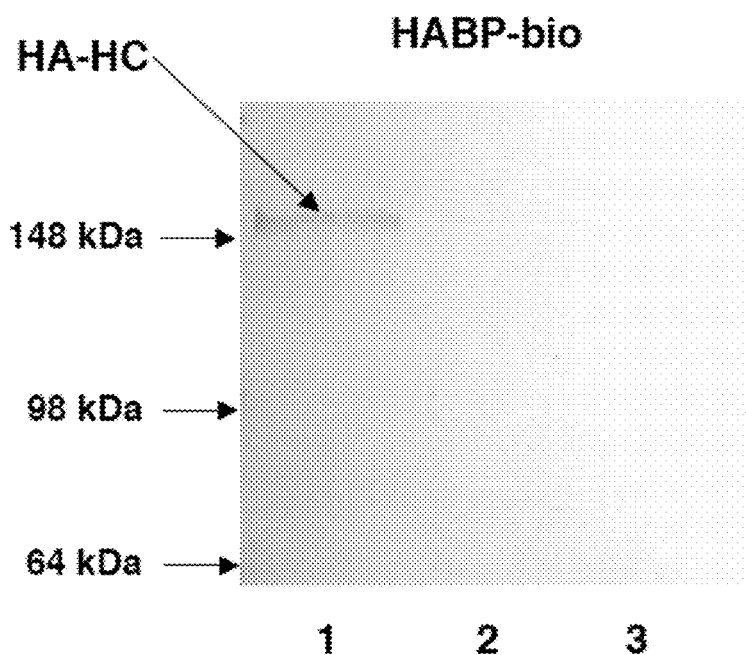
FIG. 11 is a gel showing HC transfer from IαI to HA in solution by pre-formed HA Sponge B-TSG-6 complexes. The same supernatants as in FIG. 10 were re-analyzed by immunoblotting using the HA-specific probe HABP. Note that the HABP probe does not detect the weak band visible in FIG. 10 in controls missing either TSG-6 or HA.

HC transfer by pre-formed HA Sponge B-TSG-6 complexes. FIG. 10 shows the presence of HA-HC complexes, the product of HC transfer from IαI to HA in solution, after the incubation of pre-formed TSG-6-HA Sponge B complexes with SelectHA™ in the presence of diluted human plasma as a source of IαI (lane 1). A weak band of about the same size as the HA-HC complex is also visible in lane 5, which is a plasma control (plasma diluted 1:500). It is possible that this lane represents a bikunin-HC complex, a common degradation product of IαI that has a very similar size as the HA-HC complexes. In order to confirm the nature of the band detected in lane 1 of FIG. 9 as HA-HC complex, the same material was re-analyzed by immunoblotting using the HA-specific probe HABP instead of the HC-specific antibody. FIG. 11 confirms the identity of the band formed in lane 1 as HA-HC complex. The HA-specific HABP probe detected a band of the same size exclusively in lane 1, i.e., the complex was formed exclusively after the presence of both TSG-6 in the first incubation and both plasma and SelectHA™ in the second incubation, but not in the absence of either HA (lane 2) or TSG-6 (lane 3), or both (lane 4).

Discussion

The data presented in FIG. 9 show that recombinant TSG-6 binds readily to HA Sponge B gel and also, to a lesser degree, forms a guanidine-resistant bond with this gel. Treatment with 6 M guanidine HCl containing 8% of lauryl sulfobetain has been shown to dissociate most non-covalent bonds between hyaluronan and associated proteins (Mason et al., 1982; Tsiganos et al., 1986; and Yoneda et al., 1990). It is also shown in this Example that TSG-6 bound to HA Sponge B gel in a first-step binding reaction is able to transfer HCs from IαI to SelectHA™ in a subsequent second step (FIGS. 10 and 11).

Example 3

Binding of Recombinant TSG-6 to Hylan-B and Subsequent Transfer of Heavy Chains from Inter-α-inhibitor to Hyaluronan in Solution by Hylan-B-TSG-6 Complexes The goal of this study was to demonstrate that, in addition to hyaluronan (HA) associated with a solid surface, as shown in Example 1, divinylsulfone crosslinked HA, in the form of a hydrated gel as described in U.S. Pat. No. 4,582,865, is also able to form complexes with TSG-6 protein, and that these HA-TSG-6 complexes can subsequently interact with the plasma protein inter-α-inhibitor (IαI) and transfer heavy chains (HC) from IαI to soluble HA that is in contact with the HA gel. In order to demonstrate this ability of a chemically cross-linked HA-based gel, the HA gel known as Hylan-B was used.

Materials and Methods

Reagents. Hyaluronan lyase from *Streptomyces hyaluroticus* and biotinylated hyaluronan binding protein (HABP-bio) were purchased from Associates of Cape Cod. SelectHA™ 30 kDa was purchased from Hyalose L.L.C. Human plasma was obtained from the blood bank of the NYU Medical Center. Rabbit anti-human IαI was from Dako. Although this antibody was raised against IαI, it did not detect bikunin in immunoblotting and ELISA and is therefore referred to as HC-specific. The rabbit anti-TSG-6 antibody was raised against native recombinant TSG-6 and has been described (Mindrescu et al., 2005). Biotinylated goat anti-rabbit Ig was from Dako and streptavidin-alkaline phosphatase conjugate was from Invitrogen. The alkaline phosphatase substrate was BCIP/NBT from Bio-Rad for immunoblots. PDVF membrane for immunoblotting was from Millipore (Immobilon P). Hylan-B gel was obtained from the Matrix Biology Institute (Edgewater, N.J.) as a hydrated gel suspended in $dH_2O$.

TSG-6 protein. TSG-6 protein was expressed in BTI-TN-5B1-4 insect cells after infection with recombinant nuclear polyhedrosis virus (baculovirus) and purified as described (Wisniewski et al., 1994 and 2005).

Binding of TSG-6 to Hylan-B gel. Hylan-B gel was stored suspended in $dH_2O$. Before the binding experiment, the gel was washed extensively and equilibrated with TTBS (20 mM Tris pH 7.5, 500 mM NaCl, 0.1% Tween-20). The gel was then incubated with 30 nM of recombinant TSG-6 in TTBS at 37° C. for 2 h under constant rotation to facilitate contact of TSG-6 with the gel particles. Finally, the gel was washed extensively with TTBS to remove any free TSG-6. In order to test the stability of the bond between TSG-6 and Hylan-B, one aliquot of gel was then treated with 6M guanidine HCl containing 8% of lauryl sulfobetain (LSB). After incubation for 30 min at ambient temperature, the gel was washed extensively to remove all dissociated TSG-6 and the guanidine/LSB solution, and the remaining supernatant was removed by centrifugation in a Spin-X column at 20,000 g for 3 min. The remaining gel was then subjected to digestion by 50 μl of a 10 u/ml solution of *Streptomyces* hyaluronan lyase for 2 h at 37° C. The digested gel was collected by centrifugation in a Spin-X column at 20,000 g for 3 min and analyzed by immunoblotting using a rabbit anti-TSG-6 antibody.

Transfer of HCs by HA gel-TSG-6 complexes. Hylan-B gel was stored suspended in $dH_2O$. Before the binding experiment, the gel was washed extensively and equilibrated with the buffer used for the subsequent binding of TSG-6 to Hylan B, either TTBS, TBS (20 mM Tris pH 7.5, 500 mM NaCl), PBS 5 mM $MgCl_2$, or PBS containing 5 mM $MgCl_2$ and 0.1% Tween-20). The gel was then incubated with 30 nM of recombinant TSG-6 in the same buffer at 37° C. for 2 h under constant rotation to facilitate contact of TSG-6 with the gel particles. Finally, the gel was washed extensively with TTBS to remove any free TSG-6. The washed hylan B gel containing complexes with TSG-6 was then incubated with diluted human plasma, as a source of IαI, at a final concentration of 1:500 in the presence of SelectHA™ 30 kDa to transfer HCs from IαI to the SelectHA™. The incubation was carried out in PBS containing 5 mM $MgCl_2$ to facilitate HC transfer by HA-TSG-6 complexes in a 2-step reaction (Colon et al., 2009). The supernatant containing the SelectHA™ was then collected and analyzed by immunoblotting for the presence of HA-HC complexes using either a rabbit anti-HC antibody or a HA-specific probe (HABP). Immunoblotting was carried out using 12% polyacrylamide gels and denaturing conditions (2% SDS, 5% 2-mercaptoethanol), and PVDF as blotting membrane.

Results

Figure 12:
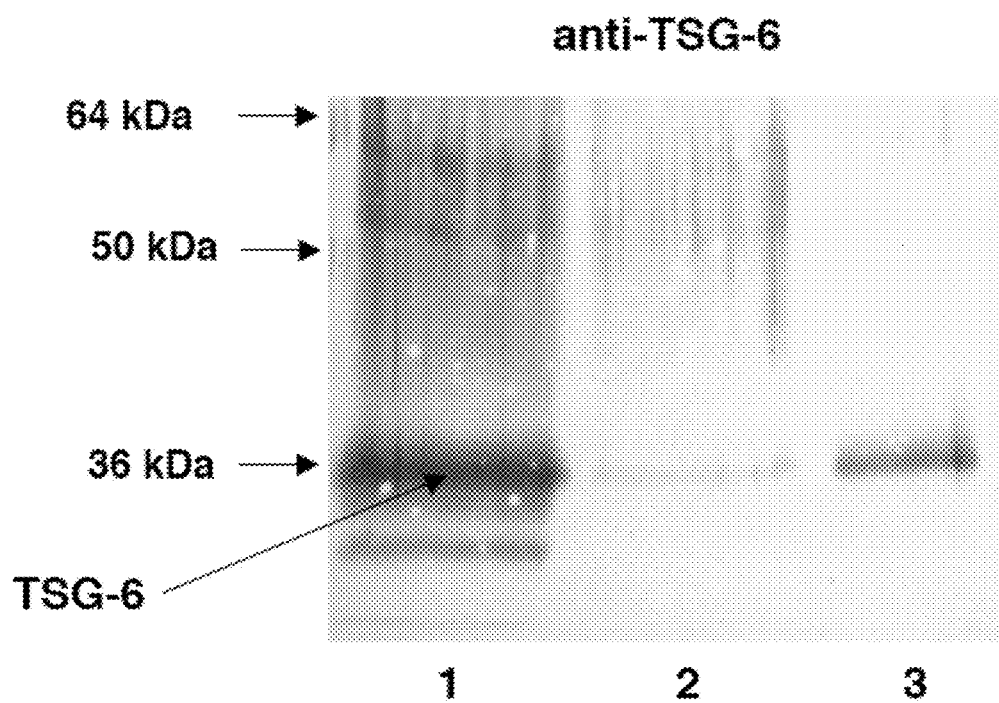
FIG. 12 is a gel showing formation of a stable bond between TSG-6 and Hylan-B HA gel. 30 nM TSG-6 in TTBS (20 mM Tris pH 7.5, 500 mM NaCl, 0.1% Tween-20) was incubated with 50 µl of Hylan-B gel in a total volume of 100 µl at 37° C. for 2 h to form Hylan-B-TSG-6 complexes. The gel of lane 2 was then treated with 6 M guanidine HCl containing 8% lauryl sulfobetain for 30 min at ambient temperature and washed extensively with TTBS. After centrifugation in a Spin-X tube to remove all supernatant, the gel was re-suspended in the Spin-X tube in 50 µl of 10 u/ml of *Streptomyces* hyaluronan lyase in PBS for 2 h at 37° C. Thereafter, after centrifugation at 20,000 g for 3 min, the filtrate was collected and analyzed by immunoblotting using a rabbit anti-TSG-6 antibody. Lane 3 contains recombinant TSG-6 as a control.

Formation of stable Hylan-B-TSG-6 complexes. FIG. 12 shows that TSG-6 protein, after incubation with Hylan-B and extensive washing with TTBS, was found associated with Hylan-B (lane 1). Although treatment with 6M guanidine HCl containing 8% LSB resulted in a significant decrease of the amount of TSG-6 associated with the hylan B gel, TSG-6 forming a guanidine-resistant, i.e., stable bond could be detected after incubation of TSG-6 with Hylan-B (lane 2).

Figure 13:
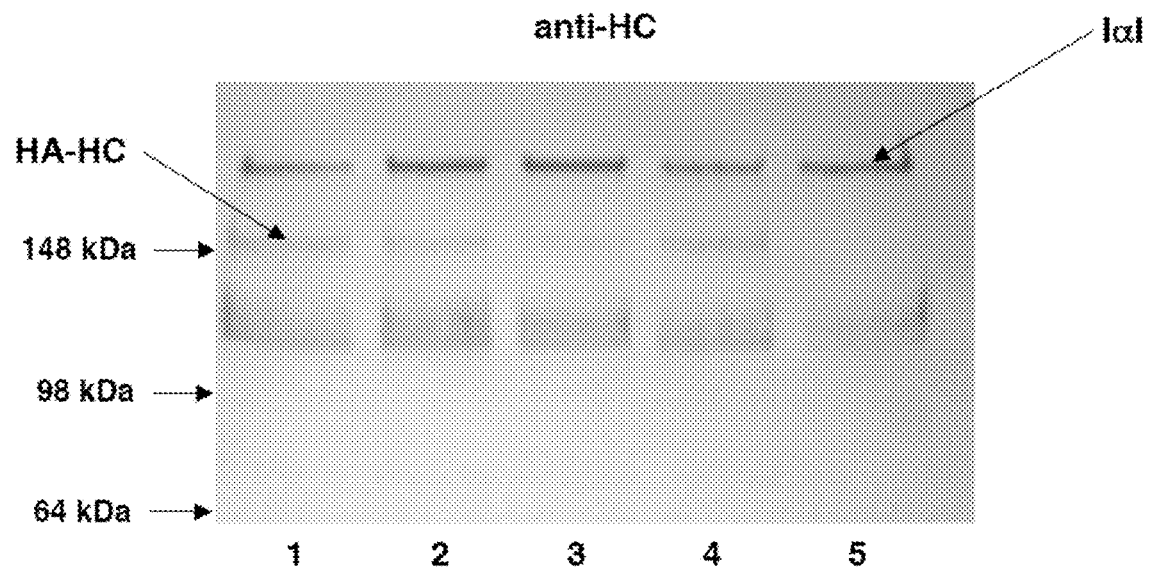
FIG. 13 is a gel showing HC transfer from IαI to HA in solution by pre-formed Hylan-B-TSG-6 complexes. 30 nM TSG-6 in TTBS (20 mM Tris pH 7.5, 500 mM NaCl, 0.1% Tween-20) (lane 1), TBS (20 mM Tris pH 7.5, 500 mM NaCl)(lane 2), PBS 5 mM $MgCl_2$ (lane 3), or PBS containing 5 mM $MgCl_2$ and 0.1% Tween-20 (lane 4) was incubated with 50 µl of Hylan-B (gel sediment) in a total volume 100 µl at 37° C. for 2 h to form Hylan-B-TSG-6 complexes. After extensive washing with TTBS, the supernatants were carefully and completely removed. Thereafter, 200 µl of 100 µg/ml of SelectHA™ 30 kDa in PBS 5 mM $MgCl_2$ containing human plasma at a final dilution of 1:500 was added to the gel sediment and incubated 37° C. for 2 h to transfer HCs to the HA. Thereafter, the supernatants were collected and analyzed by immunoblotting using an anti-HC antibody for the presence of HCs and HC-containing complexes. Lane 5 shows human plasma diluted 1:500. Note the absence of the HA-HC complex in the plasma control (lane 5).
Figure 14:
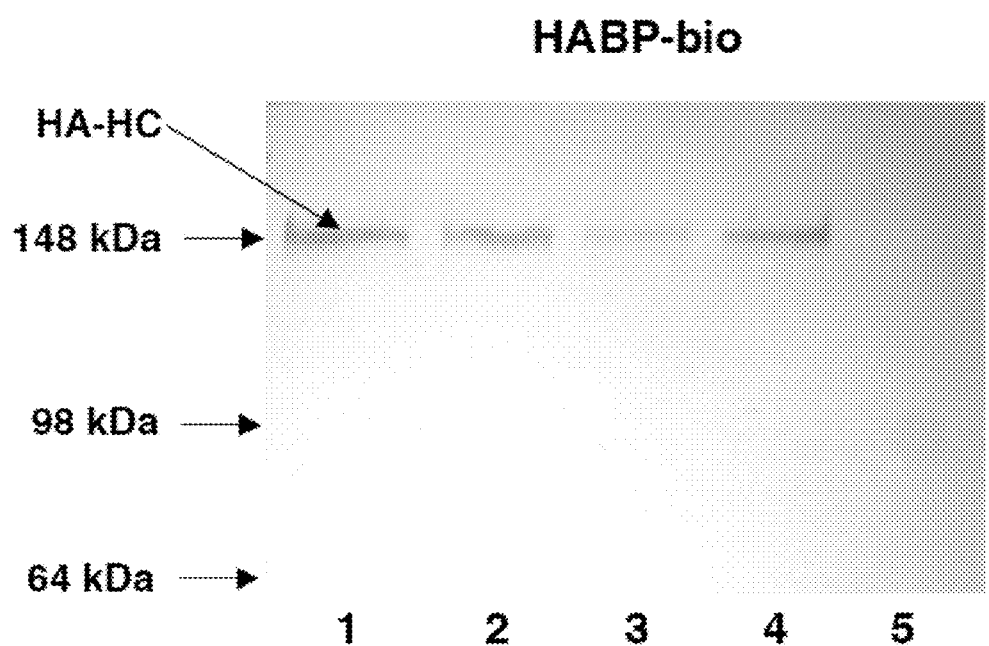
FIG. 14 is a gel showing HC transfer from IαI to HA in solution by pre-formed Hylan-B-TSG-6 complexes. The same supernatants as in FIG. 13 were re-analyzed by immunoblotting using the HA-specific probe HABP. Note the absence of the HA-HC complex in the plasma control (lane 5).
Figure 15:
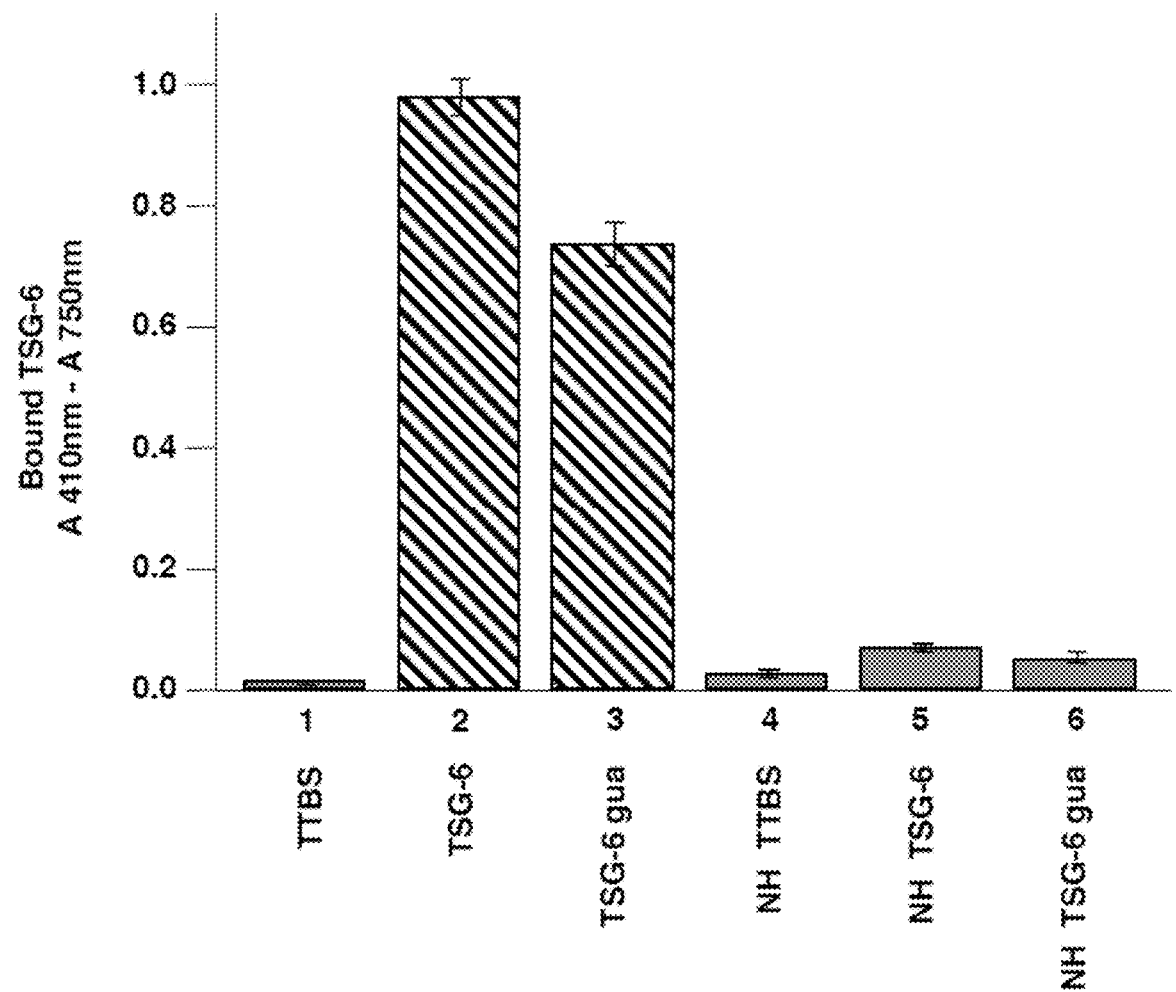
FIG. 15 is a graph showing the stability of the bond between TSG-6 and Cov-HA formed at 4° C. 10 nM purified recombinant TSG-6 in TTBS (20 mM Tris pH 7.5, 500 mM NaCl, 0.1% Tween-20) was incubated for 16 hours at 4° C. in Cov-HA or Cov-NH (as a control), as indicated. TTBS was used instead of TSG-6 as a control (lanes 1, 4). Selected wells (lanes 3, 6) were then treated with 6 M guanidine HCl containing 8% lauryl sulfobetain at ambient temperature for 15 min. Bound TSG-6 protein was then determined with a rabbit anti-TSG-6 antibody. Each data point represents the mean of 6 wells±SE.

HC transfer by pre-formed Hylan-B-TSG-6 complexes. FIG. 13 shows the formation of water soluble HA-HC complexes, the product of HC transfer from IαI to HA in solution, after the incubation of pre-formed Hylan-B-TSG-6 complexes with Select HA in the presence of diluted human plasma as a source of IαI (lanes 1 to 4). TSG-6 binding to Hylan-B, the first step of the reaction, was carried out in either TTBS (lane 1), TBS (lane 2), PBS containing 5 mM $MgCl_2$ (lane 3), or PBS containing 5 mM $MgCl_2$ and 0.1% Tween-20 (lane 4). Binding of TSG-6 in all four of these buffers resulted in subsequent HC transfer from IαI to SelectHA™ that was in contact with the Hylan gel. The HA-HC complex is not detectable in a plasma control (lane 5). In order to confirm the identity of the HA-HC complexes, the same samples were blotted again and analyzed with a HA-specific HABP probe (FIG. 14). As in FIG. 13, the HA-HC complex was detected after binding of TSG-6 to Hylan-B in various buffers and incubation with diluted human plasma and SelectHA™ in a second incubation step (lanes 1 to 4). No complex could be detected in the plasma control (lane 5).

Discussion

The data presented in FIG. 12 show that recombinant TSG-6 binds readily to Hylan-B gel and also, to a lesser degree, forms a guanidine-resistant bond with this gel. Treatment with 6 M guanidine HCl containing 8% of lauryl sulfobetain has been shown to dissociate most non-covalent bonds between hyaluronan and associated proteins (Mason et al., 1982; Tsiganos et al., 1986; and Yoneda et al., 1990). It as also shown in this Example that TSG-6 bound to Hylan-B in a first-step binding reaction is able to transfer HCs from IαI to water-soluble SelectHA™ in a subsequent second step (FIGS. 13 and 14).

Example 4

Binding of Recombinant TSG-6 to Covalink-HA and Formation of a Stable Bond at 4° C.

We have shown earlier that recombinant TSG-6 forms a stable, i.e., guanidine-resistant bond with surface-associated hyaluronan (HA) at 37° C. but not at 4° C. (Wisniewski et al., 2005). The recombinant protein used in the previous study had been purified using ion exchange chromatography and gel filtration (Mindrescu et al., 2000). In this Example, it is demonstrated that recombinant TSG-6 purified by an alternative procedure is able to form a stable bond with surface-associated HA at 4° C.

Materials and Methods

Reagents. Covalink-NH plates were purchased from Nunc, sulfo-NHS from Pierce, and EDC was purchased from Sigma. Bacterial HA used for coupling to Cov-NH was obtained from Lifecore Biomedical. The rabbit anti-TSG-6 antibody was raised against native recombinant TSG-6 and has been described (Mindrescu et al., 2005). Biotinylated goat anti-rabbit Ig was from Wako and streptavidin-alkaline phosphatase conjugate was from Invitrogen. The alkaline phosphatase substrate was p-nitrophenyl phosphate was purchased from Sigma.

TSG-6 protein. TSG-6 protein was expressed in BTI-TN-5B1-4 insect cells after infection with recombinant nuclear polyhedrosis virus (baculovirus) (Wisniewski et al., 1994) and purified as described (Wisniewski et al., 2005). In short, 100 ml of TSG-6-containing culture supernatant was mixed with 10 ml of HA-Sepharose and incubated overnight at 4° C. under constant rotation. The HA-Sepharose was washed 8 times with cold Tris-buffered saline (TTBS: 20 mM Tris pH 7.5, 500 mM NaCl, 0.1% Tween-20) and transferred to a disposable 5 ml column. The column was eluted with 2 column volumes of 3 M guanidine HCl at 4° C. and 1 ml fractions were collected. The fractions were analyzed for the presence of protein by determination of A 280 nm. Fractions containing protein were pooled and dialyzed extensively at 4° C. against PBS.

Coupling of HA to Covalink-NH plates. HA was coupled to Covalink-NH (Cov-NH) plates as described (Wisniewski et al., 2005; and Frost et al., 1997). In brief, HA solution containing sulfo-NHS was added to the wells of Cov-NH plates. After addition of EDC, the plates were incubated for 2 h at room temperature and overnight at 4° C. Thereafter, the plates were washed extensively with 2 M NaCl and blocked with 0.2% casein in TTBS. Covalink plates with surface-coupled HA are referred to as Covalink-HA (Cov-HA).

TSG-6 binding using Covalink-HA. The assay for TSG-6 binding to Cov-HA was carried out as described (Wisniewski et al., 2005). In short, 10 nM of TSG-6 protein in TTBS was incubated in the wells of Cov-HA or Cov-NH plates (as a control) at 4° C. for 16 h. After incubation with TSG-6 protein, Cov-HA or Cov-NH was washed 3 times with TTBS, followed by incubation with a rabbit anti-TSG-6 antiserum (dilution 1:1000 in TTBS), a biotinylated goat anti-rabbit immunoglobulin antibody (dilution 1:1000 in TTBS), a streptavidin-alkaline phosphatase conjugate (dilution 1:1000 in TTBS), and finally p-nitrophenyl phosphate (2 mg/ml in 50 mM Tris, pH 9.5). Between every incubation step with antibodies, etc., the wells were washed three times with 200 μl of TTBS. The amount of dephosphorylated substrate was determined by measuring the absorbance (A) at 410 nm, using the wave length of 750 nm as reference. In order to test the stability of the bond between TSG-6 and surface-coupled HA, selected wells were treated with 6M guanidine HCl containing 8% lauryl sulfobetain (LSB) for 15 min at ambient temperature, a treatment that results in the dissociation of most non-covalent bonds between proteins and HA (Yoneda et al., 1990).

Results

Formation of a stable HA-TSG-6 complexes. Using recombinant TSG-6, purified by affinity chromatography on HA-Sepharose, it was found that incubation at 4° C. for 16 h resulted in binding of TSG-6 to surface-associated HA (Cov-HA) (FIG. 15, lane 2) and in the formation of a stable, i.e., guanidine-resistant bond (FIG. 15, lane 3). Treatment of TSG-6 bound to Cov-HA with 6M guanidine HCl containing 8% LSB resulted in the dissociation of some TSG-6, but 75% of the TSG-6 formed a guanidine-resistant, i.e., stable bond with Cov-HA (lane 3 vs. 2). Lane 5 of FIG. 15 shows that the non-specific, i.e., HA-independent binding of TSG-6 to Cov-NH is negligible.

Discussion

We reported earlier that recombinant TSG-6 purified by a protocol including ion exchange chromatography and gel filtration, but not affinity chromatography on immobilized HA, formed a stable, i.e., guanidine-resistant bond with HA coupled to a solid surface (Wisniewski et al., 2005), and that formation of the stable bond was strictly temperature dependent, i.e., the stable bond was formed at 37° C., but not at 4° C. (Wisniewski et al., 2005). Here, the present inventors are providing evidence that recombinant TSG-6 purified by affinity chromatography on HA-Sepharose (Wisniewski et al., 2005) is able to form such a stable bond at 4° C. The new data presented in this Example suggest that binding of native TSG-6 to HA-Sepharose during its purification by affinity chromatography, or the subsequent elution of this protein from the HA-Sepharose with 3M guanidine HCl, or the combination of both, result in a lasting conformational change enabling TSG-6 to form a stable bond with surface-associated HA at 4° C.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Albersdörfer, A. and Sackmann, E. (1999) "Swelling behavior and viscoelasticity of ultrathin grafted hyaluronic acid films" *Eur. Phys. J. B* 10, 663-672.

Asari, A. (2004) "Medical Application of Hyaluronan", in Chemistry and Biology of Hyaluronan, H. G. Garg and C. A. Hales, eds., Elsevier, Amsterdam, pp. 457-473.

Baek, Y. W., S. Brokat, J. F. Padbury, H. Pinar, D. C. Hixson, and Y. P. Lim. (2003) Inter-alpha inhibitor proteins in infants and decreased levels in neonatal sepsis. *J Pediatr* 143:11-15.

Balazs, E. A., Leschiner, E., Larsen, N. E., and Band, P. (1993) "Applications of Hyaluronan and its Derivatives" In *Biotechnological Polymers* (Ed. Gebelein, C. G.) Technomic Publishing Co, Inc., Lancaster, Basel, 41-65.

Balazs, E. A. (2004) "Viscoelastic Properties of Hyaluronan and its Therapeutic Use", in Chemistry and Biology of Hyaluronan, H. G. Garg and C. A. Hales, eds., Elsevier, Amsterdam, pp. 415-455.

Balduyck, M., F. Piva, C. Mizon, P. Maes, N. Malki, B. Gressier, C. Michalski, and J. Mizon. (1993) Human leucocyte elastase (HLE) preferentially cleaves the heavy chain H2 of inter-alpha-trypsin inhibitor (ITI). *Biol Chem Hoppe Seyler* 374:895-901.

Balduyck, M., D. Albani, M. Jourdain, C. Mizon, A. Tournoys, H. Drobecq, F. Fourrier, and J. Mizon. (2000) Inflammation-induced systemic proteolysis of inter-alpha-inhibitor in plasma from patients with sepsis. *J Lab Clin Med* 135:188-198.

Barbucci, R., Magnani, A., Lamponi, S., Mitola, S., Ziche, M., Morbidelli, L., and Bussolino, F. (2000a) "Cu(II) and Zn(II) complexes with hyaluronic acid and its sulphated derivative. Effect on the motility of vascular endothelial cells", *J. Inorg. Biochem.* 81, 229-237.

Barbucci, R., Rappuoli, R., Borzacchiello, A., and Ambrosio, L. (2000b) "Synthesis, chemical and rheological characterization of new hyaluronic acid-based hydrogels" *J. Biomater. Sci. Polymer Edn* 11, 383-399.

Barbucci, R., Magnani, A., Rappuoli, R., Lamponi, S., and Consumi, M. (2000c) "Immobilisation of sulphated hyaluronan for improved biocompatibility" *J. Inorg. Biochem.* 79, 11.9-125.

Barbault-Foucher, S., Gref, R., Russo, P., Guechot, J., and Bochot, A. (2002) "Design of poly-ϵ-caprolactone nanospheres coated with bioadhesive hyaluronic acid for ocular delivery" *J. Control. Release* 83, 365-375.

Barbucci, R., Lamponi, S., Borzacchiello, A., Ambrosio, L., Fini, M., Torricelli, P., and Giardino, R. (2002a) "Hyaluronic acid hydrogel in the treatment of osteoarthritis" *Biomaterials* 23, 4503-4513.

Barbucci, R., Lamponi, S., Magnani, A., and Pasqui, D. (2002b) "Micropatterned surfaces for the control of endothelial cell behaviour" *Biomolec. Eng.* 19, 161-170.

Barbucci, R., Lamponi, S., and Aloisi, A. M. (2002c) "Platelet adhesion to commercial and modified polymer materials in animals under psychological stress and in a no-stress condition" *Biomaterials* 23, 1967-1973.

Barbucci, R., Pasqui, D., Wirsen, A., Affrossman, S., Curtis, A., and Tetta, C. (2003a) "Micro and nano-structured surfaces" *J. Mater. Sci. Mater. Med.* 14, 721-725.

Barbucci, R., Magnani, A., Lamponi, S., Pasqui, and Bryan, S. (2003b) "The use of hyaluronan and its sulphated derivative patterned with micrometric scale on glass substrate in melanocyte cell behaviour" *Biomaterials* 24, 915-926.

Barbucci, R. and Leone, G. (2004) "Formation of Defined Microporous 3D Structures Starting from Cross-Linked Hydrogels" *J. Biomed. Mater. Res. Part B: Appl. Biomater.* 685, 117-126.

Barbucci, R., Fini, M., Giavaresi, G., Torricelli, P., Giardino, R., Lamponi, S., and Leone, G. (2005a) "Hyaluronic Acid Hydrogel Added with Ibuprofen-Lysine for the Local Treatment of Chondral Lesions in the Knee: In Vitro and In Vivo Investigations" *J. Biomed. Mater. Res. Part B: Appl. Biomater.* 75B, 42-48.

Barbucci, R., Torricelli, P., Fini, M., Pasqui, D., Favia, P., Sardella, E., d'Agostino, R., Giardino, R. (2005b) "Proliferative and re-differentiative effects of photo-immobilized micro-patterned hyaluronan surfaces on chondrocyte cells. *Biomaterials* 26, 7596-7605.

Barbucci, R., Magnani, A., Chiumiento, A., Pasqui, D., Cangioli, I., and Lamponi, S. (2005c) "Fibroblast Cell Behavior on Bound and Adsorbed Fibronectin onto Hyaluronan and Sulfated Hyaluronan Hyaluronan Substrates" *Biomacromolecules* 6, 638-645.

Barbucci, R., Lamponi, S., Magnani, A., Piras, F. M., Rossi, A., and Weber, E. (2005d) "Role of the Hyal-Cu (II) Complex on Bovine Aortic and Lymphatic Endothelial Cells Behavior on Microstructures Surfaces" *Biomacromolecules* 6, 212-219.

Barbucci, R., Leone, G., Chiumiento, A., Di Cocco, M. E., D'Orazio, G., Gianferri, R., and Delfini, M. (2006) "Low- and high-resolution nuclear magnetic resonance (NMR) characterisation of hyaluronan-based native and sulfated hydrogels" *Carb. Res.* 341, 1848-1858.

Bardos, T., R. V. Kamath, K. Mikecz, and T. T. Giant. (2001) Anti-inflammatory and chondroprotective effect of TSG-6 (tumor necrosis factor-alpha-stimulated gene-6) in murine models of experimental arthritis. *Am J Pathol* 159:1711-1721.

Barton, J., Sagers, R. D., and Pitt, W. G. (1996) "Bacterial adhesion to orthopedic implant polymers" *J. Biomed. Mater. Res.* 30, 403-410.

Bayliss, M. T., S. L. Howat, J. Dudhia, J. M. Murphy, F. P. Barry, J. C. Edwards, and A. J. Day. (2001) Up-regulation and differential expression of the hyaluronan-binding protein TSG-6 in cartilage and synovium in rheumatoid arthritis and osteoarthritis. *Osteoarthritis Cartilage* 9:42-48.

Becker, A., and J. Sandson. (1971) The source of the inter-alpha trypsin inhibitor in pathologic hyaluronateprotein. *Arthritis Rheum* 14:764-766.

Benz, M., Chen, N., and Israelachvili, J. (2004) "Lubrication and wear properties of grafted polyelectrolytes, hyaluronan and hylan, measured in the surface forces apparatus" *J. Biomed. Mater. Res.* 71A, 6-15.

Bork, P., and G. Beckmann. (1993) The CUB domain. A widespread module in developmentally regulated proteins. *J Mol Biol* 231:539-545.

Brekke, J. H. and Thacker, K. (2006) "Hyaluronan as a Biomaterial", in An Introduction to Biomaterials, S. A. Guelcher and J. O. Hollinger, eds., CRC Press, Taylor & Francis Group, Boca Raton, Fla., pp. 219-248.

Burke, S. E. and Barrett, C. J. (2003) "pH-Responsive Properties of Multilayered Poly(L-lysine)/Hyaluronic Acid Surfaces" *Biomacromolecules* 4, 1773-1783.

Cassinelli, C., Morra, M., Pavesio, A., and Ranier, D. (2000) "Evaluation of interfacial properties of hyaluronan coated poly(methylmethacrylate) intraocular lenses" *J. Biomater. Sci. Polymer Edn.* 11, 961-977.

Catterall, J. B., Gardner, M. J., Jones, L. M. H., and Turner, G. A. (1997) "Binding of ovarian cancer cells to immobilized hyaluronic acid" *Glycoconj. J.* 14, 867-869.

Charlot, A., Heyraud, A., Guenot, P., Rinaudo, M., and AAuzély-Velty, R. (2006) "Controlled synthesis and inclusion ability of a hyaluronic acid derivative bearing β-cyclodextrin molecules" *Biomacromolecules* 7, 907-913.

Chen, L., S. J. Mao, L. R. McLean, R. W. Powers, and W. J. Larsen. 1994. Proteins of the inter-alpha-trypsin inhibitor family stabilize the cumulus extracellular matrix through their direct binding with hyaluronic acid. *J Biol Chem* 269:28282-28287.

Chen, G., Ito, Y., Imanishi, Y., Magnani, A., Lamponi, S., and Barbucci, R. (1997) "Photoimmobilization of Sulfated Hyaluronic Acid for Antithrombogenicity" *Bioconj. Chem.* 8, 730-734.

Chiumiento, A., Lamponi, S., and Barbucci, R. (2007) "Role of Fibrinogen Conformation in Platelet Activation" *Biomacromolecules* 8, 523-531.

Collin, D., Lavalle, P., Méndez Garza, J., Voegel, J-C., Schaaf, P., and Martinoty, P. (2004) "Mechanical properties of cross-linked hyaluronic acid/poly-(L-lysine) multi-layer films" *Macromolecules* 37, 10195-10198.

Colon, E., A. Shytuhina, M. K. Cowman, P. A. Band, K. W. Sanggaard, J. J. Enghild, and H. G. Wisniewski. 2009. Transfer of Inter-{alpha}-inhibitor Heavy Chains to Hyaluronan by Surface-linked Hyaluronan-TSG-6 Complexes. *J Biol Chem* 284:2320-2331.

Cowman, M. K. and Matsuoka, S. (2005) "Experimental Approaches to Hyaluronan Structure" *Carb. Res.* 340, 791-809.

Crescenzi, V., Francescangeli, A., Renier, D., and Bellini, D. (2002a) "New Cross-Linked and Sulfated Derivatives of Partially Deacetylated Hyaluronan: Synthesis and Preliminary Characterization" *Biopolymers* 64, 86-94.

Crescenzi, V., Francescangeli, A., and Taglienti, A. (2002b) "New Gelatin-Based Hydrogels via Enzymatic Networking" *Biomacromolecules* 3, 1384-1391.

Crescenzi, V., Francescangeli, A., Taglienti, A., Capitani, D., and Mannina, L. (2003) "Synthesis and Partial Characterization of Hydrogels Obtained via Glutaraldehyde Crosslinking of Acetylated Chitosan and of Hyaluronan Derivatives", *Biomacromolecules* 4, 1045-1054.

Crescenzi, V., Cornelia, L., Di Meo, C., Nardecchia, S., Lamanna, R. (2007) "Novel Hydrogels via Click Chemistry: Synthesis and Potential Biomedical Applications" *Biomacromolecules* 8, 1844-1850.

Croll, T. I., O'Connor, A. J., Stevens, G. W., and Cooper-White, J. J. (2006) "A Blank Slate? Layer-by-Layer Deposition of Hyaluronic Acid and Chitosan onto Varous Surfaces" *Biomacromolecules* 7, 1610-1622.

Dan, P., Dagan, A., Krimsky, M., Pruzanski, W., Vadas, P., and Yedgar, S. (1998) "Inhibition of Type I and Type II phospholipase $A_2$ by phosphatidyl-ethanolamine linked to polymeric carriers" *Biochemistry* 37, 6199-6204.

Dausse, Y., Grossin, L., Miralles, G., Pelletier, S., Mainard, D. Hubert, P., Baptiste, D., Gillet, P., Dellacherie, E., Netter, P., and Payan, E. (2003) "Cartilage repair using new polysaccharidic biomaterials: macroscopic, histological and biochemical approaches in a rat model of cartilage defect" *Osteoarthr. Cartilage* 11, 16-28.

de Nooy, A. E. J., Capitani, D., Masci, G., and Crescenzi, V. (2000) "Ionic Polysaccharide Hydrogels via the Passerinin and Ugi Multicomponent Condensations: Synthesis, Behavior and Solid-State NMR Characterization" *Biomacromolecules* 1, 259-267.

DeFife, K. M., Shive, M. S., Hagen, K. M., Clapper, D. L., and Anderson, J. M. (1999) "Effects of photochemically immobilized polymer coatings on protein adsorption, cell adhesion, and the foreign body reaction to silicone rubber" *J. Biomed. Mater. Res.* 44, 298-307.

Delpech, B., Bertrand, P. and Maingonnat, C. (1985) "Immunoassay of the Hyaluronic Acid—Hyaluronectin Interaction: Application to the Detection of Hyaluronic Acid in Serum of Normal Subjects and Cancer Patients" *Anal. Biochem.* 149, 555-565.

Di Meo, C., Capitani, D., Mannina, L., Brancaleoni, E., Galesso, D., De Luca, G., and Crescenzi, V. (2006) "Synthesis and NMR Characterization of New Hyaluronan-Based NO Donors", *Biomacromolecules* 7, 1253-1260.

Di Meo, C., Panza, L., Capitani, D., Mannina, L., Banzato, A., Rondina, M., Renier, D., Rosato, A., and Crescenzi, V. (2007) "Hyaluronan as Carrier of Carboranes for Tumor Targeting in Boron Neutron Capture Therapy" *Biomacromolecules* 8, 552-559.

Eliaz, R. E. and Szoka, F. C. Jr. (2001) "Liposome-encapsulated doxorubicin targeted to CD44: a strategy to kill CD44-overexpressing tumor cells" *Cancer Res.* 61, 2592-2601.

Eliaz, R. E., Nir, S., Marty, C., and Szoka, F. C. Jr. (2004a) "Determination and modeling of kinetics of cancer cell killing by doxorubicin and doxorubicin encapsulated in targted liposomes" *Cancer Res.* 64, 711-718.

Eliaz, R. E., Nir, S., and Szoka, F. C. Jr. (2004b) "Interactions of hyaluronan-targeted liposomes with cultured cells: modeling of binding and endocytosis" *Meth. Enzymol.* 387, 16-33.

Enghild, J. J., I. B. Thogersen, S. V. Pizzo, and G. Salvesen. (1989) Analysis of inter-alpha-trypsin inhibitor and a novel trypsin inhibitor, pre-alpha-trypsin inhibitor, from human plasma. Polypeptide chain stoichiometry and assembly by glycan. *J Biol Chem* 264:15975-15981.

Enghild, J. J., G. Salvesen, S. A. Hefta, I. B. Thogersen, S. Rutherfurd, and S. V. Pizzo. (1991) Chondroitin 4-sulfate covalently cross-links the chains of the human blood protein pre-alpha-inhibitor. *J Biol Chem* 266:747-751.

Enghild, J. J., G. Salvesen, I. B. Thogersen, Z. Valnickova, S. V. Pizzo, and S. A. Hefta. (1993) Presence of the protein-glycosaminoglycan-protein covalent cross-link in the inter-alpha-inhibitor-related proteinase inhibitor heavy chain 2/bikunin. *J Biol Chem* 268:8711-8716.

Etienne, O., Schneider, A., Taddei, C., Richert, L., Schaaf, P., Voegel, J-C., Egles, C., and Picart, C. (2005) "Degradability of polysaccharides multilayer films in the oral environment: an in vitro and in vivo study" *Biomacromolecules* 6, 726-733.

Fischer, S., Arad, A., and Margalit, R. (2005) "Liposome-formulated enzymes for organophosphate scavenging: Butyrylcholinesterase and Demeton-S" *Arch. Biochem. Biophys.* 434, 108-115.

Francius, G., Hemmerle, J., Ohayon, J., Schaaf, P., Voegel, J-C., Picart, C., and Senger, B. (2006) "Effect of Crosslinking on the elasticity of polyelectrolyte multilayer films measured by colloidal probe AFM" *Microsc. Res. Tech.* 69, 84-92.

Frankova, J., Kubala, L., Velebny, V., Ciz, M., Lojek, A. (2006) "The effect of hyaluronan combined with KI$_3$ complex (Hyiodine wound dressing) on keratinocytes and immune cells" *J. Mater. Sci.: Mater. Med.* 17, 891-898.

Frost, G. I., and R. Stern. (1997) A microtiter-based assay for hyaluronidase activity not requiring specialized reagents. *Anal Biochem* 251:263-269.

Fujiwara, J., Yakahashi, M., Hatakeyama, T., and Hatakeyama, H. (2000) "Gelation of hyaluronic acid through annealing" *Polym. Int.* 49, 1604-1608.

Fukuda, J., Khademhosseini, A., Yeh, J., Eng, G., Cheng, J., Farokhzad, O. C., and Langer, R. (2006) "Micropatterned cell co-cultures using layer-by-layer deposition of extracellular matrix components" *Biomaterials* 27, 1479-1486.

Fulop, C., S. Szanto, D. Mukhopadhyay, T. Bardos, R. V. Kamath, M. S. Rugg, A. J. Day, A. Salustri, V. C. Hascall, T. T. Glant, and K. Mikecz. (2003) Impaired cumulus mucification and female sterility in tumor necrosis factor-induced protein-6 deficient mice. *Development* 130:2253-2261.

Getting, S. J., D. J. Mahoney, T. Cao, M. S. Rugg, E. Fries, C. M. Milner, M. Perretti, and A. J. Day. (2002) The link module from human TSG-6 inhibits neutrophil migration in a hyaluronan- and inter-alpha-inhibitor-independent manner. *J Biol Chem* 277:51068-51076.

Giavaresi, G., Torricelli, P., Fornasari, P. M., Giardino, R., Barbucci, R., and Leone, G. (2005) "Blood vessel formation after soft tissue implantation of hyaluronan-based hydrogel supplemented with copper ions" *Biomaterials* 26, 3001-3008.

Giant, T. T., R. V. Kamath, T. Bardos, I. Gal, S. Szanto, Y. M. Murad, J. D. Sandy, J. S. Mort, P. J. Roughley, and K. Mikecz. (2002) Cartilage-specific constitutive expression of TSG-6 protein (product of tumor necrosis factor alpha-stimulated gene 6) provides a chondroprotective, but not antiinflammatory, effect in antigen-induced arthritis. *Arthritis Rheum* 46:2207-2218.

Goetinck, P. F., Stirpe, N. S., Tsonis, P. A., and Carlone, D. (1987) "The Tandemly Repeated Sequences of Cartilage Link Protein Contain the Sites for Interaction with Hyaluronic Acid" *J. Cell Biol.* 105, 2403-2408.

Gouin, S, and Winnik, F. M. (2001) "Quantitative Assays of the Amount of Dietylenetriaminepentaacetic Acid Conjugated to Water-Soluble Polymers Using Isothermal Titration calorimetry and Colorimetry" *Bioconj. J.* 12, 372-377.

Hahn, S. K. and Hoffman, A. S. (2005) Preparation and characterization of biocompatible polyelectrolyte complex multilayer of hyaluronic acid and poly-L-lysine" *Int. J. Biol. Macromol.* 37, 227-231.

Hamerman, D., M. Rojkind, and J. Sandson. 1966. Protein bound to hyaluronate: chemical and immunological studies. *Fed Proc* 25:1040-1045.

Hamilton, D. W., Riehie, M. O., Rappuoli, R., Monaghan, W., Barbucci, R., and Curtis, A. S. G. (2005) "The response of primary articular chondrocytes to micrometric surface topography and sulphated hyaluronic acid-based matrices" *Cell Biol. Int.* 29, 605-615.

Hoekstra, D. (1999) "Hyaluronan-Modified Surfaces for Medical Devices" Medical Device & Diagnostic Industry, February 1999, 48-58.

Huang, L., M. Yoneda, and K. Kimata. (1993) A serum-derived hyaluronan-associated protein (SNAP) is the heavy chain of the inter alpha-trypsin inhibitor. *J Biol Chem* 268:26725-26730.

Huin-Amargier, C., Marchal, P., Payan, E., Netter, P., and Dellacherie, E. (2005) "New physically and chemically crosslinked hyaluronate (HA)-based hydrogels for cartilage repair" *J. Biomed. Mater. Res.* 76A, 416-424.

Ibrahim, S., Joddar, B., Craps, M., Ramamurthi, A. (2007) "A surface-tethered model to assess size-specific effects of hyaluronan (HA) on endothelial cells" *Biomaterials* 28, 825-835.

Iozzo, R. V., and A. D. Murdoch. (1996) Proteoglycans of the extracellular environment: clues from the gene and protein side offer novel perspectives in molecular diversity and function. *Faseb J* 10:598-614.

Jean, L., C. Mizon, W. J. Larsen, J. Mizon, and J. P. Salier. (2001) Unmasking a hyaluronan-binding site of the BX(7)B type in the H3 heavy chain of the inter-alpha-inhibitor family. *Eur J Biochem* 268:544-553.

Jessen, T. E., and L. Odum. (2003) Role of tumour necrosis factor stimulated gene 6 (TSG-6) in the coupling of inter-alpha-trypsin inhibitor to hyaluronan in human follicular fluid. *Reproduction* 125:27-31.

Jessen, T. E., and L. Odum. (2004) TSG-6 and calcium ions are essential for the coupling of inter-alpha-trypsin inhibitor to hyaluronan in human synovial fluid. *Osteoarthritis Cartilage* 12:142-148.

Ji, Y., Ghosh, K., Shu, X. Z., Li, B., Sokolov, J. C., Prestwich, G. D., Clark, R. A. F., and Rafailovich, M. H. (2006a) "Electrospun three-dimensional hyaluronic acid nanofibrous scaffolds" *Biomaterials* 27, 3782-3792.

Ji, Y., Ghosh, K., Li, B., Sokolov, J. C., Clark, R. A. F., and Rafailovich, M. H. (2006b) "Dual-syringe reactive electrospinning of cross-linked hyaluronic acid hydrogel nanofibers for tissue engineering applications" *Macromol. Biosci.* 6, 811-817.

Joddar, B., Ibrahim, S., and Ramamurthi, A. (2007) "Impact of delivery mode of hyaluronan oligomers on elastogenic responses of adult vascular smooth muscle cells" *Biomaterials* 28, 3918-3927.

Joester, D., Klein, E., Geiger, B., and Addadi, L. (2006) "Temperature-Sensitive Micrometer-Thick Layers of Hyaluronan Grafted on Microspheres" *J. Am. Chem. Soc.* 128, 1119-1124.

Kahmann, J. D., R. O'Brien, J. M. Werner, D. Heinegard, J. E. Ladbury, I. D. Campbell, and A. J. Day. (2000) Localization and characterization of the hyaluronan-binding site on the link module from human TSG-6. *Structure* 8:763-774.

Khademhosseini, A., Suh, K. Y., Yang, J. M., Eng, G., Yeh, J., Levenberg, S., and Langer, R. (2004) "Layer-by-layer deposition of hyaluronic acid and poly-L-lysine for patterned cell co-cultures" *Biomaterials* 25, 3583-3592.

Kida, D., M. Yoneda, S. Miyaura, T. Ishimaru, Y. Yoshida, T. Ito, N. Ishiguro, H. Iwata, and K. Kimata. (1999) The SHAP-HA complex in sera from patients with rheumatoid arthritis and osteoarthritis. *J Rheumatol* 26:1230-1238.

Kim, J., Park, K., and Hahn, S. K. (2008) "Effect of hyaluronic acid molecular weight on the morphology of quantum dot-hyaluronic acid conjugates" *Int. J. Biol. Macromol.* 42, 41-45.

Kito, H. and Matsuda, T. (1996) "Biocompatible coatings for luminal and outer surfaces of small-caliber artificial grafts" *J. Biomed. Mater. Res.* 30, 321-330.

Knudson, C. B., and W. Knudson. (1993) Hyaluronan-binding proteins in development, tissue homeostasis, and disease. *Faseb J* 7:1233-1241.

Kobayashi, H., M. Suzuki, Y. Hirashima, and T. Terao. (2003) The protease inhibitor bikunin, a novel anti-metastatic agent. *Biol Chem* 384:749-754.

Kobayashi, H. (2006) Endogenous anti-inflammatory substances, inter-alpha-inhibitor and bikunin. *Biol Chem* 387: 1545-1549.

Kogan, G., Šoltés, L., Stern, R., Gemainer, P. (2007) "Hyaluronic acid: a natural biopolymer with a broad range of biomedical and industrial applications" *Biotechnol. Lett.* 29, 17-25.

Kohda, D., C. J. Morton, A. A. Parkar, H. Hatanaka, F. M. Inagaki, I. D. Campbell, and A. J. Day. (1996) Solution structure of the link module: a hyaluronan-binding domain involved in extracellular matrix stability and cell migration. *Cell* 86:767-775.

Kujawa, P., Moraille, P., Sanchez, J., Badia, A., and Winnik, F. M. (2005) "Effect of Molecular Weight on the Exponential Growth and Morphology of Hyaluronan/Chitosan Multilayers: A Surface Plasmon Resonance Spectroscopy and Atomic Force Microscopy Investigation" *J. Am. Chem. Soc.* 127, 9224-9234.

Kujawa, P. Schmauch, G., Viitala, T., Badia, A., and Winnik, F. M. (2007) "Construction of Viscoelastic Biocompatible Films via the Layer-by-Layer Assembly of Hyaluronan and Phosphorylcholine-Modified Chitosan" *Biomacromolecules* 8, 3169-3176.

Lapčík, L., Jr., Lapčík, L., DeSmedt, S., Demeester, J., and Chabreček, P. (1998) "Hyaluronan: Preparation, structure, properties, and applications" *Chem. Rev.* 98:2663-2684.

Larsson, R. (1987) "Biocompatible Surfaces Prepared by Immobilized Heparin or Hyaluronate", *Acta. Otolaryngologica*, suppl. 442:44-49.

Lee, T. H., G. W. Lee, E. B. Ziff, and J. Vilcek. (1990) Isolation and characterization of eight tumor necrosis factor-induced gene sequences from human fibroblasts. *Mol Cell Biol* 10:1982-1988.

Lee, T. H., H. G. Wisniewski, and J. Vilcek. (1992) A novel secretory tumor necrosis factor-inducible protein (TSG-6) is a member of the family of hyaluronate binding proteins, closely related to the adhesion receptor CD44. *J Cell Biol* 116:545-557.

Lee, H., Choi, S. H., and Park, T. G. (2006) "Direct Visualization of Hyaluronic Acid Polymer Chain by Self-Assembled One-Dimensional Array of Gold Nanoparticles" *Macromolecules* 39, 23-25.

Lee, H., Jeong, Y., and Park, T. G. (2007a) "Shell Cross-Linked Hyaluronic Acid/Polylysine Layer-by-Layer Polyelectrolyte Microcapsules Prepared by Removal of Reducible Hyaluronic Acid Microgel Cores" *Biomacromolecules* 8, 3705-3711.

Lee, H., Dellatore, S. M., Miller, W. M., and Messersmith, P. B. (2007b) "Mussel-Inspired Surface Chemistry for Multifunctional Coatings" *Science* 318, 426-430.

Leone, G., Barbucci, R., Borzacchiello, A., Ambrosio, L., Netti, P. A., and Migliaresi, C. (2004) "Preparation and physico-chemical characterisation of macroporous polysaccharide hydrogels" *J. Mater. Sci.: Mat. Med.* 15, 463-467.

Lesley, J., English, N. M., Gál, I., Mikecz, K., Day, A. J., and Hyman, R. (2002) "Hyaluronan Binding Properties of a CD44 Chimera Containing the Link Module of TSG-6" *J. Biol. Chem.* 277, 26600-26608.

Li, J., He, A., Zheng, J., and Han, C. C. (2006) "Gelatin and gelatin-hyaluronic acid nanofibrous membranes produced by electrospinning of their aqueous solutions" Biomacromolecules 7, 2243-2247.

Lim, Y. P., K. Bendelja, S. M. Opal, E. Siryaporn, D. C. Hixson, and J. E. Palardy. (2003) Correlation between mortality and the levels of inter-alpha inhibitors in the plasma of patients with severe sepsis. *J Infect Dis* 188:919-926.

Liu, H. and Hu, N. (2006) "Interaction between Myoglobin and Hyaluronic Acid in their Layer-by-Layer Assembly: Quartz Crystal Microbalance and Cyclic Voltammetry Studies" *J. Phys. Chem. B* 110, 14494-14502.

Liu, Y., Lu, H., Thong, W., Song, P., Kong, J., Yang, P., Girault, H. H., and Liu, B. (2006) "Multilayer-Assembled Microchip for Enzyme Immobilization as Reactor Toward Low-Level Protein Identification" *Anal. Chem.* 78, 801-808.

Lokeshwar, V. B. and Selzer, M. G. (2000) "Differences in Hyaluronic Acid-mediated Functions and Signaling in Arterial, Microvessel, and Vein-derived Human Endothelial Cells" *J. Biol. Chem.* 275, 27641-27649.

Lowry, K. M. and Beavers, E. M. (1994) "Resistance of hyaluronate coatings to hyaluronidase" *J. Biomed. Mater. Res.* 28, 861-864.

Lu, H. and Hu, N. (2007) "Salt-Induced Swelling and Electrochemical Property Change of Hyaluronic Acid/Myoglobin Multilayer Films" *J. Phys. Chem. B* 111, 1984-1993.

Luo, Y. and Prestwich, G. D. (1999) "Synthesis and selective cytotoxicity of a hyaluronic acid-antitumor bioconjugate" *Bioconjug. Chem.* 10, 755-763.

Luo, Y. and Prestwich, G. D. (2001) "Hyaluronic acid-N-hydroxysuccinimide: a useful intermediate for bioconjugation" *Bioconjug. Chem.* 12, 1085-1088.

Magnani, A., Barbucci, R., Montanaro, L., Arciola, C. R., and Lamponi, S. (2000) "In vitro study of blood-contacting properties and effect on bacterial adhesion of a polymeric surface with immobilized heparin and sulphated hyaluronic acid" *J. Biomater. Sci. Polymer Edn.* 11, 801-815.

Magnani, A., Barbucci, R., Lamponi, S., Chiumento, A., Paffetti, A., Trabalzini, L., Martelli, P., and Santucci, A. (2004) "Two-step elution of human serum proteins from different glass-modified bioactive surfaces: A comparative proteomic analysis of adsorption patterns" *Electrophoresis* 25, 2413-2424.

Mahoney, D. J., C. D. Blundell, and A. J. Day. (2001) Mapping the hyaluronan-binding site on the link module from human tumor necrosis factor-stimulated gene-6 by site-directed mutagenesis. *J Biol. Chem* 276:22764-22771.

Mason, R. M., C. d'Arville, et al. (1982). "Absence of covalently linked core protein from newly synthesized hyaluronate." *Biochem J* 207(3): 445-57.

Mason, M., Vercruysse, K. P., Kirker, K. R., Frisch, R., Marecak, D. M., Prestwich, G. D., and Pitt, W. G. (2000) "Attachment of hyaluronic acid to polypropylene, polystyrene, and polytetrafluoroethylene" *Biomaterials* 21, 31-36.

Miller, R. J. and Avila, L. Z. (2004) "Medicinal Uses of Modified Hyaluronate" in Chemistry and Biology of Hyaluronan, H. G. Garg and C. A. Hales, eds., Elsevier, Amsterdam, pp. 505-528.

Mindrescu, C., G. J. Thorbecke, M. J. Klein, J. Vilcek, and H. G. Wisniewski. (2000) Amelioration of collagen-induced arthritis in DBA/1J mice by recombinant TSG-6, a tumor necrosis factor/interleukin-1-inducible protein. *Arthritis Rheum* 43:2668-2677.

Mindrescu, C., A. A. Dias, R. J. Olszewski, M. J. Klein, L. F. Reis, and H. G. Wisniewski. (2002) Reduced susceptibility to collagen-induced arthritis in DBA/1J mice expressing the TSG-6 transgene. *Arthritis Rheum* 46:2453-2464.

Mindrescu, C., J. Le, H. G. Wisniewski, and J. Vilcek. (2005) Up-regulation of cyclooxygenase-2 expression by TSG-6 protein in macrophage cell line. *Biochem Biophys Res Commun* 330:737-745.

Mlčochova, P., Bystricky, S., Steiner, B., Machová, E., Koóš, M., Velebný, V., and Krčmář, M. (2006) "Synthesis and characterization of new biodegradable hyaluronan alkyl derivatives" *Biopolymers* 82, 74-79.

Molor-Erdene, P., K. Okajima, H. Isobe, M. Uchiba, N. Harada, and H. Okabe. (2005) Urinary trypsin inhibitor reduces LPS-induced hypotension by suppressing tumor necrosis factor-alpha production through inhibition of Egr-1 expression. *Am Physiol Heart Circ Physiol* 288: H1265-1271.

Morra, M. and Cassinelli, C. (1999) "Non-fouling properties of polysaccharide-coated surfaces" *J. Biomater. Sci. Polymer Edn.* 10, 1107-1124.

Morra, M., Cassinelli, C., Pavesio, A., and Renier, D. (2003) *J. Coll. Interface Sci.* 259, 236-243.

Morra, M. (2005) "Engineering of Biomaterials Surfaces by Hyaluronan" *Biomacromolecules* 6, 1205-1223.

Morra, M., Cassinelli, C., Carpi, A., Giardino, R., and Fini, M. (2006) "Effects of molecular weight and surface functionalization on surface composition and cell adhesion to hyaluronan coated titanium" *Biomed. Pharm.* 60, 365-369.

Mráček, A., Benešová, K., Minařík, A., Urban, P., and Lapčík, L. (2007) "The diffusion process of sodium hyaluronate (Na-HA) and Na-HA-n-alkyl derivatives films swelling" *J. Biomed. Mater. Res.* 83A, 184-190.

Mukhopadhyay, D., A. Asari, M. S. Rugg, A. J. Day, and C. Fulop. (2004) Specificity of the tumor necrosis factor-induced protein 6-mediated heavy chain transfer from inter-alpha-trypsin inhibitor to hyaluronan: implications for the assembly of the cumulus extracellular matrix. *J. Bio. Chem.* 279:11119-11128.

Odum, L., C. Y. Andersen, and T. E. Jessen. (2002) Characterization of the coupling activity for the binding of inter-alpha-trypsin inhibitor to hyaluronan in human and bovine follicular fluid. *Reproduction* 124:249-257.

Oohira, A., Kushima, Y., Tokita, Y., Sugiura, N., Sakurai, K., Suzuki, S., and Kimata, K. (2000) "Effects of lipid-derivatized glycosaminoglycans (GAGs), a novel probe for functional analyses of GAGs, on cell-to-substratum adhesion and neurite elongation in primary cultures of fetal rat hippocampal neurons" *Arch. Biochem. Biophys.* 378, 78-83.

Opal, S. M., Y. P. Lim, E. Siryaporn, L. L. Moldawer, J. P. Pribble, J. E. Palardy, and S. Souza. (2007) Longitudinal studies of inter-alpha inhibitor proteins in severely septic patients: a potential clinical marker and mediator of severe sepsis. *Crit Care Med* 35:387-392.

Park, J. U. and Tsuchiya, T. (2002) "Increase in gap-junctional intercellular communications (GJIC) of normal human dermal fibroblasts (NHDF) on surfaces coated with high-molecular-weight hyaluronic acid (HMW HA)" *J. Biomed. Mater. Res.* 60, 541-547.

Parkar, A. A., J. D. Kahmann, S. L. Howat, M. T. Bayliss, and A. J. Day. (1998). TSG-6 interacts with hyaluronan and aggrecan in a pH-dependent manner via a common functional element: implications for its regulation in inflamed cartilage. *FEBS Lett* 428:171-176.

Pasqui, D., Atrei, A., and Barbucci, R. (2007) "A Novel Strategy to Obtain a Hyaluronan Monolayer on Solid Substrates" *Biomacromolecules* 8, 3531-3539.

Pastorino, L., Caneva Soumetz, F., and Ruggiero, C. (2006) "Nanofunctionalisation for the treatment of peripheral nervous system injuries" *IEE Proc.-Nanobiotechnol.* 153, 16-20.

Peer, D. and Margalit, R. (2000) "Physicochemical evaluation of a stability-driven approach to drug entrapment in regular and in surface-modified liposomes" *Arch. Biochem. Biophys.* 383, 185-190.

Peer, D., Florentin, A., and Margalit, R. (2003) "Hyaluronan is a key component in cryoprotection and formulation of targeted unilamellar liposomes" *Biochim. Biophys. Acta* 1612, 76-82.

Peer, D. and Margalit, R. (2004a) "Loading mitomycin C inside long circulating hyaluronan targeted nano-liposomes increases its antitumor activity in three mice tumor models" *Int. J. Cancer* 108, 780-789.

Peer, D. and Margalit, R. (2004b) "Tumor-targeted hyaluronan nanoliposomes increase the antitumor activity of liposomal doxorubicin in syngeneic and human xenograft mouse tumor models" *Neoplasia* 6, 343-353.

Pelletier, S., Hubert, P., Payan, E., Marchal, P., Choplin, L., and Dellacherie, E. (2000) "Amphiphilic derivatives of sodium alginate and hyaluronate for cartilage repair: rheological properties" *J. Biomed. Mater. Res.* 54, 102-108.

Picart, C., Lavalle, P., Hubert, P., Cuisinier, F. J. G., Decher, G., Schaaf, P., and Voegel, J-C. (2001) "Buildup mechanism for poly (L-lysine)/hyaluronic acid films onto a solid surface" *Langmuir* 17, 7414-7424.

Picart, C., Mutterer, J., Richert, L., Luo, Y., Prestwich, G. D., Schaal, P., Voegel, J. C., and Lavalle, P. (2002) "Molecular basis for the explanation of the exponential growth of polyelectrolyte multilayers" *Proc. Natl. Acad. Sci. USA* 99, 12531-12535.

Picart, C., Mutterer, J., Arntz, Y., Voegel, J-C., Schaaf, P., and Senger, B. (2005) "Application of fluorescence recovery after photobleaching to diffusion of a polyelectrolyte in a multilayer film" *Microsc. Res. Techn.* 66, 43-57.

Pitt, W. G., Morris, R. N., Mason, M. L., Hall, M. W., Luo, Y., and Prestwich, G. D. (2003) "Attachment of hyaluronan to metallic surfaces" *J. Biomed. Mater. Res.* 68A, 95-106.

Pravata, L., Braud, C., Boustta, M., El Ghzaoui, A., Tømmeraas, K., Guillaumie, F., Schwach-Abdellaoui, K., and Vert, M. (2008) "New amphiphilic lactic acid oligomer hyaluronan conjugates: synthesis and physicochemical characterization" *Biomacromolecules* 9, 340-348.

Prestwich, G. D., Marecak, D. M., Marecek, J. F., Vercruysse, K. P., and Ziebell, M. R. (1998) "Controlled chemical modification of hyaluronic acid: synthesis, applications, and biodegradation of hydrazide derivatives" *J. Control. Release* 53, 93-103.

Pugia, M. J., and J. A. Lott. (2005) Pathophysiology and diagnostic value of urinary trypsin inhibitors. *Clin Chem Lab Med* 43:1-16.

Richert, L., Boulmedais, F., Lavalle, P., Mutterer, J., Ferreux, E., Decher, G., Schaaf, P., Voegel, J-C., and Picart, C. (2004a) "Improvement of stability and cell adhesion properties of polyelectrolyte multilayer films by chemical cross-linking" *Biomacromolecules* 5, 284-294.

Richert, L., Lavalle, P., Payan, E., Shu, X. Z., Prestwich, G. D., Stoltz, J-F., Schaaf, P., Voegel, J-C., and Picart, C. (2004b) "Layer by layer buildup of polysaccharide films: Physical chemistry and cellular adhesion aspects" *Langmuir* 20, 448-458.

Richert, L., Engler, A. J., Discher, D. E., and Picart, C. (2004c) "Elasticity of native and cross-linked polyelectrolyte multilayer films" *Biomacromolecules* 5, 1908-1916.

Richert, L., Schneider, A., Vautier, D., Vodouhe, C., Jessel, N., Payan, E., Schaaf, P., Voegel, J-C., and Picart, C. (2006) "Imaging cell interactions with native and crosslinked polyelectrolyte multilayers" *Cell Biochem. Biophys.* 44, 273-285.

Richter, R. P., Hock, K. K., Burkhartsmeyer, J., Boehm, H., Bingen, P., Wang, G., Steinmetz, N. F., Evans, D. J., and Spatz, J. P. (2007) "Membrane-grafted hyaluronan films: a well-defined model system of glycoconjugate cell coats" *J. Am. Chem. Soc.* 129, 5306-5307.

Rosato, A., Banzato, A., De Luca, G., Renier, D., Betella, F., Pagano, C., Esposito, G., Zanovello, P., and Bassi, P. (2006) "HYTAD1-p20: a new paclitaxel-hyaluronic acid hydrosoluble bioconjugate for treatment of superficial bladder cancer" *Urol. Oncol.* 24, 207-215.

Rugg, M. S., A. C. Willis, D. Mukhopadhyay, V. C. Hascall, E. Fries, C. Fulop, C. M. Milner, and A. J. Day. (2005) Characterization of complexes formed between TSG-6 and inter-alpha-inhibitor that act as intermediates in the covalent transfer of heavy chains onto hyaluronan. *J Biol Chem* 280:25674-25686.

Ruhela, D., Riviere, K., and Szoka, F. C. Jr. (2006) "Efficient synthesis of an aldehyde functionalized hyaluronic acid and its application in the preparation of hyaluronan-lipid conjugates" *Bioconjugate Chem.* 17, 1360-1363.

Sakurai, K., Miyazaki, K., Kodera, Y., Nishimura, H. Shingu, M., and Inada, Y. (1997) "Anti-inflammatory activity of superoxide dismutase conjugated with sodium hyaluronate" *Glycoconj. J.* 14, 723-728.

Salier, J. P., P. Rouet, G. Raguenez, and M. Daveau. (1996) The inter-alpha-inhibitor family: from structure to regulation. *Biochem J* 315 (Pt 1):1-9.

Sandson, J., D. Hamerman, and G. Schwick. (1965) Altered properties of pathological hyaluronate due to a bound inter-alpha trypsin inhibitor. *Trans Assoc Am Physicians* 78:304-313.

Sanggaard, K. W., H. Karring, Z. Valnickova, I. B. Thogersen, and J. J. Enghild. (2005) The TSG-6 and I alpha I interaction promotes a transesterification cleaving the protein-glycosaminoglycan-protein (PGP) cross-link. *J Biol Chem* 280:11936-11942.

Sanggaard, K. W., C. S. Sonne-Schmidt, C. Jacobsen, I. B. Thogersen, Z. Valnickova, H. G. Wisniewski, and J. J. Enghild. (2006) Evidence for a Two-Step Mechanism Involved in the Formation of Covalent HC.TSG-6 Complexes. *Biochemistry* 45:7661-7668.

Santos, H. A., Manzanares, J. A., Murtomäki, L., and Kontturi, K. (2007) "Thermodynamic analysis of binding between drugs and glycosaminoglycans by isothermal titration calorimetry and fluorescence spectroscopy" *Eur. J. Pharm. Sci.* 32, 105-114.

Sato, H., S. Kajikawa, S. Kuroda, Y. Horisawa, N. Nakamura, N. Kaga, C. Kakinuma, K. Kato, H. Morishita, H. Niwa, and J. Miyazaki. (2001) Impaired fertility in female mice lacking urinary trypsin inhibitor. *Biochem Biophys Res Commun* 281:1154-1160.

Schneider, A., Francius, G., Obeid, R., Schwinte, P., Hemmerlé, J., Frisch, B., Schaaf, P., Voegel, J-C., Senger, B., and Picart, C. (2006) "Polyelectrolyte multilayers with a tunable Young's Modulus: Influence of film stiffness on cell adhesion" *Langmuir* 22, 1193-1200.

Schneider, A., Picart, C., Senger, B., Schaaf, P., Voegel, J-C., and Frisch, B. (2007a) "Layer-by-layer films from hyaluronan and amine-modified hyaluronan" *Langmuir* 23, 2655-2662.

Schneider, A., Vodouhe, C., Richert, L., Francius, G., Le Guen, E., Schaaf, P., Voegel, J-C., Frisch, B., and Picart, C. (2007b) "Multifunctional polyelectrolyte multilayer films: Combining mechanical resistance, biodegradability, and bioactivity" *Biomacromolecules* 8, 139-145.

Schnitzer, E., Dagan, A., Krimsky, M., Lichtenberg, D., Pinchuk, I., Shinar, H., and Yedgar, S. (2000) "Interaction of hyaluronic-linked phosphatidylethanolamine (HyPE) with LDL and its effect on the susceptibility of LDL lipids to oxidation" *Che. Phys. Lipids* 104, 149-160.

Sengupta, K., Schilling, J., Marx, S. Fischer, M., Bacher, A., and Sackmann, E. (2003) "Mimicking tissue surfaces by supported membrane coupled ultrathin layer of hyaluronic acid" *Langmuir* 19, 1775-1781.

Shu, X. Z. and Prestwich, G. D. (2004) "Therapeutic Biomaterials from Chemically Modified Hyaluronan" in *Chemistry and Biology of Hyaluronan*, H. G. Garg and C. A. Hales, eds., Elsevier, Amsterdam, pp. 475-504.

Šoltés, L. and Mendichi, R. (2003) "Molecular characterization of two host-guest associating hyaluronan derivatives" *Biomed. Chromatogr.* 17, 376-384.

Šoltés, L., Mendichi, R., Kogan, G., and Mach, M. (2004) "Associating hyaluronan derivatives: a novel horizon in viscosupplementation of osteoarthritic joints" *Chemistry Biodiversity* 1, 468-472.

Stern, R., Asari, A., Sugahara, K. N. (2006) "Hyaluronan fragments: An information-rich system" *Eur. J. Cell Biol.* 85, 699-715.

Suh, K. Y., Khademhosseini, A., Yang, J. M., Eng, G., and Langer, R. (2004) "Soft Lithographic Patterning of Hyaluronic Acid on Hydrophilic Substrates Using Molding and Printing" *Adv. Mater.* 16, 584-588.

Suh, K. Y., Yang, J. M., Khademhosseini, A., Berry, D., Tran, T-N. T., Park, H., and Langer, R. (2005) "Characterization of Chemisorbed Hyaluronic Acid Directly Immobilized on Solid Substrates" *J. Biomed. Mater. Res. Part B Appl. Biomater.* 72B, 292-298.

Taglienti, A., Valentini, M., Sequi, P., and Crescenzi, V. (2005) "Characterization of Methylprednisolone Esters of Hyaluronan in Aqueous Solution: Conformation and Aggregation Behavior", *Biomacromolecules* 6, 1648-1653.

Taglienti, A., Cellesi, F., Crescenzi, V., Sequi, P., Valentini, M., and Tirelli, N. (2006) "Investigating the Interactions of Hyaluronan Derivatives with Biomolecules. The Use of Diffusional NMR Techniques", *Macromol. Biosci.* 6, 611-622.

Takahashi, M., Hatakeyama, T., and Hatakeyama, H. (2000) "Phenomenological theory describing the behaviour of non-freezing water in structure formation process of polysaccharide aqueous solutions" *Carbohydr. Polym.* 41, 91-95.

Tezcaner, A., Hicks, D., Boulmedais, F., Sahel, J., Schaaf, P., Voegel, J-C., and Lavalle, P. (2006) "Polyelectrolyte Multilayer Films as Substrates for Photoreceptor Cells" *Biomacromolecules* 7, 86-94.

Thierry, B., Winnik, F. M., Merhi, Y., and Tabrizian, M. (2003a) "Nanocoatings onto Arteries via Layer-by-Layer Deposition: Towards the in Vivo Repair of Damaged Blood Vessels" *J. Am. Chem. Soc.* 125, 7494-7495.

Thierry, B., Winnik, F. M., Merhi, Y., Silver, J., and Tabrizian, M. (2003b) "Bioactive Coatings of Endovascular Stents Based on Polyelectrolyte Multilayers" *Biomacromolecules* 4, 1564-1571.

Thierry, B., Winnik, F. M., Merhi, Y., Silver, J., and Tabrizian, M. (2004) "Radionuclides-hyaluronan-conjugate thromboresistant coatings to prevent in-stent restenosis" *Biomaterials* 25, 3895-3905.

Thierry, B., Kujawa, P., Tkaczyk, C., Winnik, F. M., Bilodeau, L., and tabrizian, M. (2005) "Delivery Platform for Hydrophobic Drugs: Prodrug Approach Combined with Self-Assembled Multilayers" *J. Am. Chem. Soc.* 27, 1626-1627.

Toole, B. P. (1990) Hyaluronan and its binding proteins, the hyaladherins. *Curr Opin Cell Biol* 2:839-844.

Topfer-Petersen, E., A. Romero, P. F. Varela, M. Ekhlasi-Hundrieser, Z. Dostalova, L. Sanz, and J. J. Calvete. (1998) Spermadhesins: a new protein family. Facts, hypotheses and perspectives. *Andrologia* 30:217-224.

Tsiganos, C. P., D. H. Vynios, et al. (1986). "Rooster comb hyaluronate-protein, a non-covalently linked complex." *Biochem J* 235(1): 117-23.

Um, I. C., Fang, D., Hsiao, B. S., Okamoto, A., and Chu, B. (2004) "Electro-spinning and electro-blowing of hyaluronic acid" *Biomacromolecules* 5, 1428-1436.

Veerabadran, N. G., Goli, P. L., Stewart-Clark, S. S., Lvov, Y. M., and Mills, D. K. (2007) "Nanoencapsulation of Stem Cells within Polyelectrolyte Multilayer Shells" *Macromol. Biosci.* 7, 877-882.

Vercruysse, K. P. and Prestwich, G. D. (1998) "Hyaluronate derivatives in drug delivery" *Crit. Rev. Ther. Drug Carrier Syst.* 15, 513-555.

Wang, A., Cao, T., Tang, H., Liang, X., Black, C., Salley, S. O., McAllister, J. P., Auner, G. W., and Ng, K. Y. S. (2006) "Immobilization of polysaccharides on a fluorinated silicon surface" *Coll. Surf. B: Biointerfaces* 47, 57-63.

Wisniewski, H. G., J. C. Hua, D. M. Poppers, D. Naime, J. Vilcek, and B. N. Cronstein. (1996) TNF/IL-1-inducible protein TSG-6 potentiates plasmin inhibition by inter-alpha-inhibitor and exerts a strong anti-inflammatory effect in vivo. *J Immunol* 156:1609-1615.

Wisniewski, H. G., R. Maier, M. Lotz, S. Lee, L. Klampfer, T. H. Lee, and J. Vilcek. (1993) TSG-6: a TNF-, IL-1-, and LPS-inducible secreted glycoprotein associated with arthritis. J Immunol 151:6593-6601.

Wisniewski, H. G., W. H. Burgess, J. D. Oppenheim, and J. Vilcek. (1994) TSG-6, an arthritis-associated hyaluronan binding protein, forms a stable complex with the serum protein inter-alpha-inhibitor. *Biochemistry* 33:7423-7429.

Wisniewski, H. G., and J. Vilcek. (1997) TSG-6: an IL-1/TNF-inducible protein with anti-inflammatory activity. *Cytokine Growth Factor Rev* 8:143-156.

Wisniewski, H. G., and J. Vilcek. (2004) Cytokine-induced gene expression at the crossroads of innate immunity, inflammation and fertility: TSG-6 and PTX3/TSG-14. *Cytokine Growth Factor Rev* 15:129-146.

Wisniewski, H. G., E. S. Snitkin, C. Mindrescu, M. H. Sweet, and J. Vilcek. (2005) TSG-6 protein binding to glycosaminoglycans: formation of stable complexes with hyaluronan and binding to chondroitin sulfates. *J Biol Chem* 280: 14476-14484.

Wisniewski, H. G., M. H. Sweet, and R. Stern. (2005) An assay for bacterial and eukaryotic chondroitinases using a chondroitin sulfate-binding protein. *Anal Biochem* 347:42-48.

Wu, R., X. Cui, Y. P. Lim, K. Bendelja, M. Zhou, H. H. Simms, and P. Wang. (2004) Delayed administration of human inter-alpha inhibitor proteins reduces mortality in sepsis. *Crit Care Med* 32:1747-1752.

Yang, S., Y. P. Lim, M. Zhou, P. Salvemini, H. Schwinn, D. Josic, D. J. Koo, I. H. Chaudry, and P. Wang. (2002) Administration of human inter-alpha-inhibitors maintains hemodynamic stability and improves survival during sepsis. *Crit Care Med* 30:617-622.

Yerushalmi, N., Arad, A., and Margalit, R. (1994) "Molecular and cellular studies of hyaluronic acidmodified liposomes as bioadhesive carriers for topical drug delivery in wound healing" *Arch. Biochem. Biophys.* 313, 267-273.

Yerushalmi, N. and Margalit, R. (1998) "Hyaluronic acid-modified bioadhesive liposomes as local drug depots: effects of cellular and fluid dynamics on liposome retention at target sites" *Arch. Biochem. Biophys.* 349, 21-26.

Yoneda, M., S. Suzuki, et al. (1990). "Hyaluronic acid associated with the surfaces of cultured fibroblasts is linked to a serum-derived 85-kDa protein." *J Biol Chem* 265(9): 5247-57.

Zhang, J., Senger, B., Vautier, D., Picart, C., Schaaf, P. Voegel, J.-C., and Lavalle, P. (2005) "Natural polyelectrolyte films based on layer-by-layer deposition of collagen and hyaluronic acid" *Biomaterials* 26, 3353-3361.

Zhang, M., King, R., Hanes, M., and James, S. P. (2006) "A novel ultra high molecular weight polyethylene-hyaluronan microcomposite for use in total joint replacements. I. Synthesis and physical/chemical characterization" *J. Biomed. Mater. Res.* 78A, 86-96.

Zhang, M., Pare, P., King, R., and James, S. P. (2006) "A novel ultra high molecular weight polyethylene-hyaluronan microcomposite for use in total joint replacements. II. Mechanical and tribological property evaluation" *J. Biomed. Mater. Res.* 82A, 18-26.

Zhao, M., M. Yoneda, Y. Ohashi, S. Kurono, H. Iwata, Y. Ohnuki, and K. Kimata. (1995) Evidence for the covalent binding of SHAP, heavy chains of inter-alpha-trypsin inhibitor, to hyaluronan. *J Biol Chem* 270:26657-26663.

Hirose, J., T. Ozawa, T. Miura, M. Isaji, Y. Nagao, K. Yamashiro, A. Nii, K. Kato, and A. Uemura. (1998) Human neutrophil elastase degrades inter-alpha-trypsin inhibitor to liberate urinary trypsin inhibitor related proteins. *Biol Pharm Bull* 21:651-656.

Zhuo, L., M. Yoneda, M. Zhao, W. Yingsung, N. Yoshida, Y. Kitagawa, K. Kawamura, T. Suzuki, and K. Kimata. (2001) Defect in SHAP-hyaluronan complex causes severe female infertility. A study by inactivation of the bikunin gene in mice. *J Biol Chem* 276:7693-7696.

What is claimed is:

1. A method for inhibiting inflammation or for providing a chondroprotective effect, comprising introducing a biocompatible material locally to the site of inflammation in a patient in need thereof, the biocompatible material being in the form of a water insoluble covalently cross-linked gel, wherein
the biocompatible material in the form of a water insoluble covalently cross-linked gel comprises:
hyaluronan (HA), as a water insoluble covalently cross-linked HA gel or mutually cross-linked with at least one other polymer in a water insoluble covalently cross-linked gel; and
TNF-stimulated gene 6 protein (TSG-6) in a stable complex with said HA, wherein said TSG-6 in said stable complex is capable of transferring heavy chains (HCs) of inter-α-inhibitor (IαI) to bound or free HA.

2. The method of claim 1, wherein the biocompatible material is implanted in the patient.

3. The method of claim 1, wherein said HA is the water insoluble covalently cross-linked HA gel to which TSG-6 is complexed.

4. The method of claim 1, wherein the stable complex of TSG-6 and HA is resistant to treatment with 6M guanidine HCl containing 8% lauryl sulfobetain (3-(Dodecyldimethylammonio) propanesulfonate, Zwittergent®) for 30 minutes at ambient temperature or is resistant to boiling in reducing SDS-PAGE sample buffer of 0.25 M Tris pH 6.8, 2% sodium dodecylsulfate, 5% 2-mercapto ethanol, 10% glycerol.

5. The method of claim 1, wherein said HA is mutually cross-linked with at least one other polymer in a water insoluble covalently cross-linked gel.

6. The method of claim 1, wherein
the biocompatible material is biodegradable.

7. The method of claim 1, wherein said stable complex of TSG-6 and HA is capable of being released in a soluble form.

* * * * *

SEQUENCE LISTING

<160> NUMBER OF SEQ ID NOS: 3

<210> SEQ ID NO 1
<211> LENGTH: 277
<212> TYPE: PRT
<213> ORGANISM: Homo sapiens (human)

<400> SEQUENCE: 1

```
Met Ile Ile Leu Ile Tyr Leu Phe Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
            35                  40                  45

Leu Thr Tyr Ala Glu Ala Lys Ala Val Cys Glu Phe Glu Gly Gly His
50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
            115                 120                 125

Asn Pro His Ala Lys Glu Cys Gly Gly Val Phe Thr Asp Pro Lys Arg
            130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
            195                 200                 205

Tyr Cys Gly Asp Glu Leu Pro Asp Asp Ile Ile Ser Thr Gly Asn Val
210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
            275
```

<210> SEQ ID NO 2
<211> LENGTH: 277
<212> TYPE: PRT
<213> ORGANISM: Canis lupus familiaris (dog)

<400> SEQUENCE: 2

Met Ile Ile Phe Ile Ser Leu Phe Val Leu Leu Trp Glu Glu Ala His
1               5                   10                  15

Gly Trp Gly Phe Asn Asn Gly Ile Phe His Asn Ser Ile Trp Leu Glu
            20                  25                  30

Gln Ala Ala Gly Val Tyr His Arg Glu Ala Arg Ser Gly Arg Tyr Arg
        35                  40                  45

Leu Thr Tyr Ala Glu Ala Lys Ala Val Cys Glu Phe Glu Gly Gly Arg
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Val Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Asp Asp Asn Gln Ile
145                 150                 155                 160

Cys Tyr Trp His Ile Arg Val Lys Tyr Gly Gln Arg Val His Leu Ser
                165                 170                 175

Phe Leu Asp Phe Asp Leu Glu Asp Asp Pro Ala Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Glu Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Ile Ala Val Asp Pro Leu Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 3
<211> LENGTH: 277
<212> TYPE: PRT
<213> ORGANISM: Equus caballus (horse)

<400> SEQUENCE: 3

Met Ile Ile Leu Ile Tyr Val Leu Val Leu Leu Trp Glu Glu Ala His
1               5                   10                  15

Gly Trp Gly Phe Lys Asn Gly Ile Phe His Asn Ser Ile Trp Leu Glu
            20                  25                  30

Gln Ala Ala Gly Val Tyr His Arg Glu Ala Arg Ser Gly Lys Tyr Lys
        35                  40                  45

Leu Thr Tyr Ala Glu Ala Lys Ala Val Cys Glu Tyr Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

```
Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Ile Phe Thr Asp Thr Lys Arg
        130                 135                 140

Ile Phe Lys Ser Pro Gly Phe Pro Asn Glu Tyr Asp Asp Asn Gln Val
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Thr Gly Cys Leu Ala Asp Tyr
            180                 185                 190

Val Glu Ile Tyr Asp Ser Tyr Asp Asp Val His Gly Phe Val Gly Arg
            195                 200                 205

Tyr Cys Gly Asp Glu Leu Pro Glu Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240

Gln Ile Lys Tyr Val Ala Val Asp Pro Pro Ser Lys Pro Ser Gln Gly
                245                 250                 255

Lys Asn Thr Ser Thr Thr Ser Thr Gly Asn Lys Ser Phe Leu Ala Pro
                260                 265                 270

Ser Phe Thr His Leu
            275
```